US012186316B2

(12) United States Patent
Wang et al.

(10) Patent No.: US 12,186,316 B2
(45) Date of Patent: Jan. 7, 2025

(54) PHARMACEUTICAL COMPOSITIONS

(71) Applicant: Shenzhen Pharmacin Co., Ltd., Shenzhen (CN)

(72) Inventors: Zeren Wang, Shenzhen (CN); Shun Chen, Shenzhen (CN); Jiqian Peng, Shenzhen (CN); Longwei Sun, Shenzhen (CN); Yanxin Zhao, Shenzhen (CN)

(73) Assignee: Shenzhen Pharmacin Co., Ltd., Shenzhen (CN)

( * ) Notice: Subject to any disclaimer, the term of this patent is extended or adjusted under 35 U.S.C. 154(b) by 0 days.

(21) Appl. No.: 18/609,790

(22) Filed: Mar. 19, 2024

(65) Prior Publication Data

US 2024/0226102 A1  Jul. 11, 2024

Related U.S. Application Data

(60) Division of application No. 18/191,637, filed on Mar. 28, 2023, which is a continuation of application No. PCT/CN2021/121695, filed on Sep. 29, 2021.

(30) Foreign Application Priority Data

Sep. 29, 2020  (WO) ................ PCT/CN2020/118608

(51) Int. Cl.
*A61K 31/506* (2006.01)
*A61K 9/20* (2006.01)
*A61K 9/48* (2006.01)

(52) U.S. Cl.
CPC .......... *A61K 31/506* (2013.01); *A61K 9/2009* (2013.01); *A61K 9/2013* (2013.01); *A61K 9/2027* (2013.01); *A61K 9/2031* (2013.01); *A61K 9/205* (2013.01); *A61K 9/2054* (2013.01); *A61K 9/4825* (2013.01); *A61K 9/4866* (2013.01)

(58) Field of Classification Search
CPC ................ A61K 31/506; A61K 9/2009; A61K 9/2013; A61K 9/2027; A61K 9/2031; A61K 9/205; A61K 9/2054; A61K 9/4825; A61K 9/4866; A61K 9/141; A61K 9/20; A61K 9/48; A61K 9/4858; A61P 35/00
See application file for complete search history.

(56) References Cited

U.S. PATENT DOCUMENTS

| | | |
|---|---|---|
| 7,169,791 B2 | 1/2007 | Breitenstein et al. |
| 8,163,904 B2 | 4/2012 | Manley et al. |
| 8,293,756 B2 | 10/2012 | Bruneau |
| 8,389,537 B2 | 3/2013 | Manley et al. |
| 8,415,363 B2 | 4/2013 | Manley et al. |
| 8,501,760 B2 | 8/2013 | Bruneau |
| 9,023,393 B2 | 5/2015 | Babcock et al. |
| 9,061,029 B2 | 6/2015 | Gallagher et al. |
| 9,456,992 B2 | 10/2016 | Brisander et al. |
| 9,486,410 B2 | 11/2016 | Perlman et al. |
| 9,580,408 B2 | 2/2017 | Peddy et al. |
| 9,682,081 B2 | 6/2017 | Fanda et al. |
| 9,827,230 B2 | 11/2017 | Brisander et al. |
| 9,833,442 B2 | 12/2017 | Brisander et al. |
| 9,833,443 B2 | 12/2017 | Brisander et al. |
| 9,877,923 B2 | 1/2018 | Figueiredo et al. |
| 10,016,423 B2 | 7/2018 | Pompili et al. |
| 10,143,683 B2 | 12/2018 | Brisander et al. |
| 10,314,829 B2 | 6/2019 | Brisander et al. |
| 10,314,830 B2 | 6/2019 | Brisander et al. |
| 10,357,455 B2 | 7/2019 | Perlman et al. |
| 10,383,941 B2 | 8/2019 | Beyerinck et al. |
| 10,772,877 B2 | 9/2020 | Brisander et al. |
| 10,874,671 B2 | 12/2020 | Jain et al. |
| 11,376,243 B2 | 7/2022 | Brisander et al. |
| 11,389,450 B2 | 7/2022 | Wertz et al. |
| 11,559,485 B2 | 1/2023 | Wertz et al. |
| 2003/0185893 A1 | 10/2003 | Beyerinck et al. |
| 2008/0292707 A1 | 11/2008 | Babcock et al. |
| 2009/0203709 A1 | 8/2009 | Steinberg et al. |
| 2014/0378454 A1 | 12/2014 | Brisander et al. |
| 2015/0273070 A1 | 10/2015 | Li et al. |
| 2015/0320749 A1 | 11/2015 | Bhardwaj et al. |
| 2016/0250153 A1 | 9/2016 | Brisander et al. |
| 2017/0143715 A1 | 5/2017 | Brisander et al. |
| 2019/0255029 A1 | 8/2019 | Brisander et al. |

(Continued)

FOREIGN PATENT DOCUMENTS

| | | |
|---|---|---|
| CN | 1675195 A | 9/2005 |
| CN | 1324022 C | 7/2007 |

(Continued)

OTHER PUBLICATIONS

Hoogevest, Eur. J. Lipid. Sci. Technol., 2014, 116, 1088-1107 (Year: 2014).*
Qian, Journal of Pharmaceutical Sciences, vol. 101, No. 2, 2012 (Year: 2012).*
Anane-Adjei, Akosua, et al., Amorphous Solid Dispersions: Utilization and Challenges in Preclinical Drug Development Within AstraZeneca, International Journal of Pharmaceutics 614:1-16 (2022).
Chaudhari, Smruti, et al., Evaluating the Effect of the Porous and Non-porous Colloidal Silicon Dioxide as a Stabilizer on Amorphous Solid Dispersion, Journal of Drug Delivery & Therapeutics 10(5):255-263 (2020).
Heimbach, T. et al., "Physiologically Based Pharmacokinetic Modeling to Supplement Nilotinib Pharmacokinetics and Confirm Dose Selection in Pediatric Patients," J Pharm Sci., 2019;108(6):2191-2198.

(Continued)

*Primary Examiner* — Susanna Moore
*Assistant Examiner* — Luisalberto Gonzalez
(74) *Attorney, Agent, or Firm* — Wilson Sonsini Goodrich & Rosati

(57) ABSTRACT

Provided are pharmaceutical compositions which include a mixture of a lipophilic active pharmaceutical ingredient such as nilotinib, a hydrophilic polymer, one or more surfactants, and optionally an adsorbent. Also described are methods for preparing and using such pharmaceutical compositions. In one aspect, disclosed herein is an amorphous solid dispersion comprising the active pharmaceutical ingredient.

30 Claims, 1 Drawing Sheet

(56) References Cited

U.S. PATENT DOCUMENTS

| | | |
|---|---|---|
| 2020/0222394 A1 | 7/2020 | Jain et al. |
| 2022/0362246 A1 | 11/2022 | Wertz et al. |
| 2022/0378788 A1 | 12/2022 | Wertz et al. |
| 2023/0157948 A1 | 5/2023 | Wertz et al. |
| 2023/0158026 A1 | 5/2023 | Wertz et al. |
| 2023/0172931 A1 | 6/2023 | Wertz et al. |
| 2023/0181585 A1 | 6/2023 | Wertz et al. |

FOREIGN PATENT DOCUMENTS

| | | | |
|---|---|---|---|
| CN | 101185633 A | 5/2008 | |
| CN | 101336890 A | 1/2009 | |
| CN | 101516344 A | 8/2009 | |
| CN | 101185627 B | 4/2011 | |
| CN | 102267981 A | 12/2011 | |
| CN | 102358736 A | 2/2012 | |
| CN | 103608342 A | 2/2014 | |
| CN | 102612368 B | 3/2014 | |
| CN | 103804356 A | 5/2014 | |
| CN | 102836159 B | 12/2014 | |
| CN | 104306350 A | 1/2015 | |
| CN | 104367557 A | 2/2015 | |
| CN | 104274837 B | 1/2017 | |
| CN | 106932522 A | 7/2017 | |
| CN | 107320460 A | 11/2017 | |
| CN | 104812381 B | 1/2018 | |
| CN | 109475553 A | 3/2019 | |
| KR | 20170085629 A | 7/2017 | |
| WO | WO-2004005281 A8 | 5/2004 | |
| WO | WO-2007015871 A1 | 2/2007 | |
| WO | WO-2007015870 A3 | 6/2007 | |
| WO | WO-2008016260 A1 | 2/2008 | |
| WO | WO-2008037716 A3 | 7/2008 | |
| WO | WO-2009100176 A3 | 3/2010 | |
| WO | WO-2011062927 A1 | 5/2011 | |
| WO | WO-2012164578 A1 | 12/2012 | |
| WO | WO-2012174082 A1 | 12/2012 | |
| WO | WO-2013105894 A1 | 7/2013 | |
| WO | WO-2013105895 A1 | 7/2013 | |
| WO | WO-2014043618 A1 | 3/2014 | |
| WO | WO-2014174496 A1 | 10/2014 | |
| WO | WO-2016097011 A1 | 6/2016 | |
| WO | WO-2017064538 A1 | 4/2017 | |
| WO | WO-2017149550 A1 | 9/2017 | |
| WO | WO-2017158625 A1 | 9/2017 | |
| WO | WO-2018076117 A1 | 5/2018 | |
| WO | WO-2020121326 A1 | 6/2020 | |
| WO | WO-2020172120 A1 * | 8/2020 | ......... A61K 31/4985 |
| WO | WO-2020225738 A1 | 11/2020 | |
| WO | WO-2021219808 A1 | 11/2021 | |
| WO | WO-2022049243 A1 | 3/2022 | |

OTHER PUBLICATIONS

Herbrink, M. et al., "Improving the solubility of nilotinib through novel spray-dried solid dispersions," International Journal of Pharmaceutics, 2017;529(1-2):294-302.

International Preliminary Report on Patentability issued in PCT/CN2021/121695, dated Mar. 28, 2023.

International Search Report and Written Opinion issued in PCT/CN2021/121695, mailed Jan. 4, 2022.

Kondra, S.B. et al., "A validated stability-indicative UPLC method for nilotinib hydrochloride for the determination of process-related and degradation impurities," Journal of Chromatographic Science, 2014;52(8):880-885.

Munzenberg, J. et al., Improving the Dissolution of Poorly Soluble APIs with Inorganic Solid Dispersions, Pharmaceutical Technology, vol. 41, 4 (2017).

Pallicer, J. M., "Evaluation of log Po/w values of drugs from some molecular structure calculation software," ADMET and DMPK, 2014;2(2):107-114.

Zhang, Z. et al., Solid dispersion of berberine-phospholipid complex/TPGS 1000/$SiO_2$: preparation, characterization and in vivo studies. International journal of pharmaceutics, vol. 465, 1-2 (2014):306-316.

Van Hoogevest, Peter. et al. The use of phospholipids to make pharmaceutical form line extensions. European journal of lipid science and technology 123(4):2000297, 1-38 (2021).

* cited by examiner

PHARMACEUTICAL COMPOSITIONS

CROSS REFERENCE TO RELATED APPLICATION

This application is a division of U.S. application Ser. No. 18/191,637 filed Mar. 28, 2023, which is a continuation of PCT application No. PCT/CN2021/121695 filed Sep. 29, 2021, which claims the benefit of PCT application No. PCT/CN2020/118608 filed Sep. 29, 2020, each of which is hereby incorporated by reference in its entirety.

BACKGROUND

The chemical name of nilotinib free base is 4-methyl-N-[3-(4-methyl-1H-imidazol-1-yl)-5-(trifluoromethyl)phenyl]-3-{[4-(pyridin-3-yl)pyrimidin-2-yl]amino}benzamide. Nilotinib hydrochloride is approved for the treatment of chronic myelogenous leukemia (CML) under the trade name TASIGNA®. The structure of nilotinib free base is depicted below.

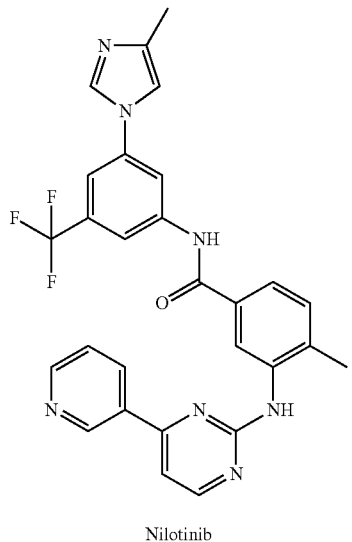 [SMILES: Cc1cn(-c2cc(NC(=O)c3ccc(C)c(Nc4nccc(-c5cccnc5)n4)c3)cc(C(F)(F)F)c2)cn1]

Nilotinib

Nilotinib is a lipophilic compound, with a cLog P=5.8, making the compound practically insoluble in water. TASIGNA® is known to have the potential to result in increased and highly variable exposures when administered with meals. Significant prolongation of the QT interval may occur when nilotinib is inappropriately taken with food and/or strong CYP3A4 inhibitors and/or medicinal products with a known potential to prolong QT. Therefore, coadministration with food must be avoided and concomitant use with strong CYP3A4 inhibitors and/or medicinal products with a known potential to prolong QT should be avoided. Sudden deaths have been reported in 0.3% of patients with CML treated with TASIGNA® in clinical studies of 5,661 patients. The relative early occurrence of some of these deaths related to the initiation of TASIGNA® suggests the possibility that ventricular repolarization abnormalities may have contributed to their occurrence.

There is a need for nilotinib compositions that have improved oral bioavailability, permit administering lower doses, that reduce absorption variations caused by food intake, and that reduce in vivo inter-subject absorption variations. More generally, there is a need for improved formulations of highly lipophilic active pharmaceutical ingredients to provide improved oral bioavailability, permit administering lower doses, that reduce absorption variations caused by food intake, and that reduce in vivo inter-subject absorption variations.

INCORPORATION BY REFERENCE

All publications and patent applications mentioned in this specification are herein incorporated by reference to the same extent as if each individual publication or patent application was specifically and individually indicated to be incorporated by reference.

BRIEF SUMMARY

Disclosed herein is a pharmaceutical composition, wherein the pharmaceutical composition comprises: a) an amorphous solid dispersion that comprises: i. an active pharmaceutical ingredient or a pharmaceutically acceptable salt thereof, wherein the active pharmaceutical ingredient or a pharmaceutically acceptable salt thereof is nilotinib free base or a pharmaceutically acceptable salt thereof; ii. one or more surfactants, wherein the one or more surfactants is are selected from one or more polymeric non-ionic surfactants, and one or more phospholipids, or any combination thereof; iii. a non-ionic hydrophilic polymer; and iv. optionally an adsorbent, and b) a pharmaceutically acceptable carrier or excipient. In some embodiments, the pharmaceutical composition is in a form of a tablet or capsule. In some embodiments, the nilotinib free base or a pharmaceutically acceptable salt thereof is a salt of nilotinib. In some embodiments, the salt of nilotinib is selected from nilotinib hydrochloride, nilotinib sulfate, nilotinib fumarate, nilotinib 2-chloromandelate, nilotinib succinate, nilotinib adipate, nilotinib 1-tartrate, nilotinib glutarate, nilotinib p-toluenesulfonate, nilotinib camphorsulfonate, nilotinib glutamate, nilotinib palmitate, nilotinib quinate, nilotinib citrate, nilotinib maleate, nilotinib acetate, nilotinib 1-malate, nilotinib 1-aspartate, nilotinib formate, nilotinib hydrobromide, nilotinib oxalate, and nilotinib malonate. In some embodiments, the salt of nilotinib is nilotinib hydrochloride. In some embodiments, the nilotinib free base or a pharmaceutically acceptable salt thereof is present in the pharmaceutical composition in an amount of about 10 mg to about 500 mg. In some embodiments, the nilotinib free base or a pharmaceutically acceptable salt thereof is present in the pharmaceutical composition in an amount of about 50 mg to about 125 mg of the free base or in an equivalent amount of the a pharmaceutically nilotinib acceptable salt. In some embodiments, the nilotinib free base or a pharmaceutically acceptable salt thereof is present in the pharmaceutical composition in an amount of about 10% to 30% by weight. In some embodiments, the one or more surfactants are present in the pharmaceutical composition in an amount of about 10 mg to about 500 mg. In some embodiments, the one or more surfactants are present in the pharmaceutical composition in an amount of about 25 mg to about 125 mg. In some embodiments, the one or more surfactants are present in the pharmaceutical composition in an amount of about 10% to 40% by weight. In some embodiments, the one or more surfactant is lecithin. In some embodiments, the one or more surfactant is a block copolymer of polyethylene glycol and polypropylene glycol. In some embodiments, the non-ionic hydrophilic polymer is polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-β-CD), hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof. In some embodiments, the non-ionic hydrophilic polymer is present in the pharmaceutical composition in an amount of about 10 mg to about 500 mg. In some embodiments, the non-ionic hydrophilic polymer is present in the pharmaceutical composition in an amount of about 10 mg to about 200 mg. In some embodiments, the non-ionic hydrophilic polymer is present in the amorphous solid dispersion in an amount of about 1% to about 80% by weight. In some embodiments, the amorphous solid dispersion comprises silicon dioxide powder in an amount of about 10% to about 35% by weight. In some embodiments, the pharmaceutical composition is free of organic acid. In some embodiments, the pharmaceutically acceptable carrier or excipient comprises an external acid. In some embodiments, the external acid is not present in the amorphous solid dispersion. In some embodiments, the external acid is a surface modified acid comprising an acid particle and a neutral salt layer. In some embodiments, the neutral salt layer is formed by a reaction between a pharmaceutically acceptable base and powdered or granulated acid. In some embodiments, the surface modified acid is powdered or granulated. In some embodiments, the external acid is a surface modified organic acid. In some embodiments, the external acid is a surface modified acid selected from tartaric acid, fumaric acid, succinic acid, citric acid, lactic acid, malic acid, maleic acid, benzenesulfonic acid, and p-toluenesulfonic acid. In some embodiments, the external acid is a surface modified acid selected from tartaric acid, fumaric acid, succinic acid, citric acid, lactic acid, malic acid, and maleic acid. In some embodiments, the external acid is a surface modified acid selected from tartaric acid and succinic acid. In some embodiments, the pharmaceutically acceptable base is selected from sodium carbonate, potassium carbonate, sodium acetate, potassium acetate, sodium stearate, potassium stearate, lysine, arginine and histidine. In some embodiments, the pharmaceutically acceptable base is sodium carbonate. In some embodiments, a weight ratio of the pharmaceutically acceptable base to the acid particle is about 2% to about 20%. In some embodiments, the external acid is present in the pharmaceutical composition in an amount of about 50 to about 300 mg. In some embodiments, the external acid is present in the pharmaceutical composition in an amount of about 5% to about 35% by weight. In some embodiments, the pharmaceutical composition comprises: a) an amorphous solid dispersion that comprises: i. nilotinib free base or nilotinib HCl in an amount of about 10 mg to about 200 mg; ii. ii. a one or more surfactants in an amount of about 10 mg to about 500 mg, wherein the one or more surfactants comprises lecithin, or a block copolymer of polyethylene glycol and polypropylene glycol, Tocopherol polyethylene glycol succinate (TPGS, or vitamin E TPGS), or a combination thereof; iii. a non-ionic hydrophilic polymer in an amount of about 10 mg to about 500 mg, wherein the non-ionic hydrophilic polymer comprises polyvinyl alcohol (PVA), polyvinylpyrrolidone (PVP), hydroxypropyl methylcellulose (HPMC), or hydroxypropyl beta cyclodextrin (HP-β-CD); and iv. optionally silicone dioxide in an amount of about 10 mg to 300 mg, and b) a pharmaceutically acceptable carrier or excipient. In some embodiments, the pharmaceutical composition comprises: a) an amorphous solid dispersion that comprises: i. nilotinib free base or nilotinib HCl in an amount of about 50 mg to about 125 mg; ii. one or more surfactant in an amount of about 10 mg to about 500 mg, wherein the one or more surfactants comprise lecithin; iii. a non-ionic hydrophilic polymer in an amount of about 10 mg to about 200 mg, wherein the non-ionic hydrophilic polymer comprises polyvinyl alcohol (PVA), polyvinylpyrrolidone (PVP), hydroxypropyl methylcellulose (HPMC), or hydroxypropyl beta cyclodextrin (HP-β-CD); and iv. optionally silicone dioxide in an amount of about 50 mg to 150 mg, and b) an external acid in an amount of about 50 mg to 300 mg, wherein the external acid is a surface modified acid. In some embodiments, the pharmaceutical composition comprises: a) an amorphous solid dispersion (ASD) that comprises: i. nilotinib free base or nilotinib HCl in an amount of about 5% to about 35% by weight of the ASD; ii. one or more surfactants in an amount of about 5% to about 50% by weight of the ASD, wherein the one or more surfactants comprise one or more phospholipids, one or more non-ionic surfactants, or any combination thereof; iii. a non-ionic hydrophilic polymer in an amount of about 1% to about 80% by weight of the ASD, wherein the non-ionic hydrophilic polymer comprises polyvinyl alcohol (PVA), polyvinylpyrrolidone (PVP), hydroxypropyl methylcellulose (HPMC), or hydroxypropyl beta cyclodextrin (HP-β-CD); and iv. optionally silicone dioxide in an amount of about 10% to 40% by weight of the ASD, and b) a pharmaceutically acceptable carrier or excipient. In some embodiments, the pharmaceutical composition comprises: a) an amorphous solid dispersion (ASD) that comprises: i. nilotinib free base or nilotinib HCl in an amount of about 5% to about 35% by weight of the ASD; ii. one or more surfactants in an amount of about 5% to about 50% by weight of the ASD, wherein the one or more surfactants comprise lecithin, a block copolymer of polyethylene glycol and polypropylene glycol, TPGS, or a combination thereof; iii. a non-ionic hydrophilic polymer in an amount of about 1% to about 80% by weight of the ASD, wherein the non-ionic hydrophilic polymer comprises polyvinyl alcohol (PVA), polyvinylpyrrolidone (PVP), hydroxypropyl methylcellulose (HPMC), or hydroxypropyl beta cyclodextrin (HP-β-CD); and iv. optionally silicone dioxide in an amount of about 10% to 40% by weight of the ASD, and b) a pharmaceutically acceptable carrier or excipient. In some embodiments, the pharmaceutical composition comprises: a) an amorphous solid dispersion that comprises: i. nilotinib free base or nilotinib HCl in an amount of about 15% to about 30% by weight of the ASD; ii. one or more surfactants in an amount of about 10% to about 40% by weight of the ASD, wherein the one or more surfactants comprise lecithin, a block copolymer of polyethylene glycol and polypropylene glycol, TPGS, or a combination thereof; iii. a non-ionic hydrophilic polymer in an amount of about 15% to about 60% by weight of the ASD, wherein the non-ionic hydrophilic polymer comprises polyvinyl alcohol (PVA), polyvinylpyrrolidone (PVP), hydroxypropyl methylcellulose (HPMC), or hydroxypropyl beta cyclodextrin (HP-β-CD); and iv. optionally silicone dioxide in an amount of about 15% to 35% by weight of the ASD, and b) a pharmaceutically acceptable carrier or excipient. In some embodiments, the pharmaceutical composition comprises: a) an amorphous solid dispersion that comprises: i. nilotinib free base or nilotinib HCl in an amount of about 15% to about 30% by weight of the ASD; ii. one or more surfactants in an amount of about 10% to about 40% by weight of the ASD, wherein the one or more surfactants comprise lecithin, a block copolymer of polyethylene glycol and polypropylene glycol, TPGS, or a combination thereof; iii. a non-ionic hydrophilic polymer in an amount of about 15% to about 60% by weight of the ASD, wherein the non-ionic hydrophilic polymer comprises polyvinyl alcohol (PVA), polyvinylpyrrolidone (PVP), hydroxypropyl methylcellulose (HPMC), or hydroxypropyl beta cyclodextrin (HP-β-CD); and iv. optionally silicone dioxide in an amount of about 15% to 35% by weight of the ASD, and an external acid in an amount of about 5% to 35% by weight of the pharmaceutical composition. In some embodiments, the pharmaceutical composition is storage stable for at least 2 weeks at 75° C./75% RH, wherein a storage stable pharmaceutical composition has less than 100 ppm of Impurity A at the end of the storage period. In some embodiments, the pharmaceutical composition is storage stable for at least 6 months at 40° C./75% RH, wherein a storage stable pharmaceutical composition has less than 100 ppm of Impurity A at the end of the storage period. In some embodiments, the pharmaceutical composition is storage stable for at least 2 weeks, 1 month, 2 months, 3 months, 6 months, 12 months, or 24 months at 40° C./75% RH, wherein a storage stable pharmaceutical composition has less than 100 ppm of Impurity A at the end of the storage period. In some embodiments, the pharmaceutical composition exhibits a bioavailability that is at least 2-fold higher than a bioavailability of a corresponding formulation comprising nilotinib free base or a pharmaceutically acceptable salt thereof in a crystalline form, when measured as the total area under the curve (AUC) after oral administration or when measured as Cmax after oral administration. In some embodiments, the pharmaceutical composition exhibits a bioavailability that is at least 2-fold higher than a bioavailability of a reference pharmaceutical composition that comprises nilotinib HCl, when measured as the total area under the curve (AUC) after oral administration or when measured as Cmax after oral administration, wherein the reference pharmaceutical composition does not comprise an amorphous solid dispersion. In some embodiments, the bioavailability is measured in a dog model in a fasted state or in a fed state. In some embodiments, a bioavailability of the pharmaceutical composition does not vary for more than 50% when orally administered in a fed state compared to a bioavailability administered in a fasted state, when measured as the total area under the curve (AUC) after oral administration or when measured as Cmax after oral administration.

Disclosed herein is a pharmaceutical composition, wherein the pharmaceutical composition comprises: a) an amorphous solid dispersion that comprises: i. an active pharmaceutical ingredient or a pharmaceutically acceptable salt thereof, wherein the active pharmaceutical ingredient has a log P in octanol-water equal or greater than 2.0; ii. one or more surfactants, wherein the one or more surfactants areis selected from polymeric non-ionic surfactants, and phospholipids, or a combination thereof; iii. a non-ionic hydrophilic polymer; and iv. optionally adsorbent, b) a pharmaceutically acceptable carrier or excipient. In some embodiments, the pharmaceutical composition is in a form of a tablet or capsule. In some embodiments, the active pharmaceutical ingredient or a pharmaceutically acceptable salt thereof is selected from nilotinib, abiraterone acetate, celecoxib, flurazepam, atorvastatin, indometacin, nortriptyline, loratadine, fluoxetine, diclofenac, clopidogrel, duloxetine, maprotiline, imipramine, amitriptyline, cyproheptadine, sertraline, flufenamic acid, chlorpromazine, miconazole, rimonabant, clofazimine, enzalutamide, lapatinib, pazopanib, erlotinib, dasatinib, gefitinib, sorafenib, axitinib, crizotinib, vemurafenib, telotristat ethyl, ivacaftor, nintedanib, ibrutinib, alectinib, bosutinib, lenvatinib, midostaurin, avapritinib, pexidartinib, alectinib, neratinib, enzalutamide, the corresponding free base thereof and pharmaceutically acceptable salts thereof. In some embodiments, the active pharmaceutical ingredient has a log P in octanol-water equal or greater than 3.0. In some embodiments, the active pharmaceutical ingredient is a compound of Formula (I), or a N-oxide or a pharmaceutically acceptable salt thereof,

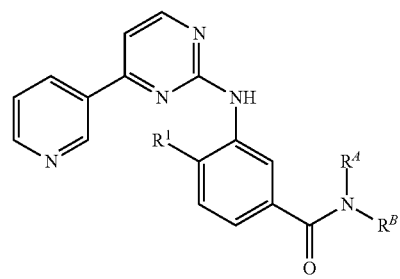

Formula (I)

wherein
$R^1$ is hydrogen, $C_1$-$C_6$ alkyl, or halogen;
$R^A$ is hydrogen, $C_1$-$C_6$ alkyl, $C_{1-6}$ alkoxy-$C_{1-6}$ alkyl, acyloxy-$C_{1-6}$ alkyl, carboxy-$C_{1-6}$ alkyl, $C_{1-6}$ alkoxy-carbonyl-$C_{1-6}$ alkyl, or phenyl-$C_{1-6}$ alkyl,
$R^B$ is hydrogen, $C_1$-$C_6$ alkyl, optionally and independently substituted by one or more $R^{10}$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or poly-substituted, wherein
$R^{10}$ represents hydroxy, $C_1$-$C_6$ alkoxy, acyloxy, carboxy, $C_{1-6}$ alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted; or
$R^A$ and $R^B$ taken together form a $C_4$-$C_6$ alkylene optionally mono- or disubstituted by $C_1$-$C_6$ alkyl, cycloalkyl, heterocyclyl, phenyl, hydroxy, $C_1$-$C_6$ alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by $C_1$-$C_6$ alkyl, phenyl-$C_1$-$C_6$ alkyl, $C_{1-6}$ alkoxycarbonyl-$C_{1-6}$ alkyl, carboxy-$C_{1-6}$ alkyl, carbamoyl-$C_{1-6}$ alkyl, N-mono- or N,N-disubstituted carbamoyl-$C_{1-6}$ alkyl, cycloalkyl, $C_{1-6}$ alkoxycarbonyl, carboxy, phenyl, substituted phenyl, pyridinyl, pyrimidinyl, or pyrazinyl.

In some embodiments, the active pharmaceutical ingredient or a pharmaceutically acceptable salt thereof is present in the pharmaceutical composition of a unit dosage form in an amount of about 10 mg to about 500 mg. In some embodiments, the one or more surfactants are present in the pharmaceutical composition of a unit dosage form in an amount of about 10 mg to about 500 mg. In some embodiments, the one or more surfactants are Poloxamer 188, lecithin, TPGS, or a combination thereof. In some embodiments, wherein the non-ionic hydrophilic polymer is polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-β-CD), hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof. In some embodiments, the non-ionic hydrophilic polymer is present in the pharmaceutical composition in an amount of about 10 mg to about 500 mg. In some embodiments, the composition comprises an adsorbent, wherein the adsorbent is selected from silicon dioxide, active carbon, magnesium aluminum silicate, diatomite, microcrystalline cellulose (MCC), silicified microcrystalline cellulose (SMCC), talc, crosslinked povidone, sodium carboxymethylcellulose, sodium carboxymethyl starch, and also sugars or sugar alcohols such as sorbitol, mannitol, lactose, cyclodextrin, and maltodextrin. In some embodiments, the adsorbent is silicon dioxide. In some embodiments, the adsorbent is present in the amorphous solid dispersion in an amount of about 10% to about 35% by weight. In some embodiments, the pharmaceutically acceptable carrier or excipient comprises an external acid. In some embodiments, the external acid is a surface modified acid comprising an acid particle and a neutral salt layer. In some embodiments, the neutral salt layer is formed by a reaction between a pharmaceutically acceptable base and powdered or granulated acid. In some embodiments, the surface modified acid is powdered or granulated. In some embodiments, the external acid is a surface modified organic acid. In some embodiments, the external acid is a surface modified acid selected from tartaric acid, fumaric acid, succinic acid, citric acid, lactic acid, malic acid, maleic acid, benzenesulfonic acid, and p-toluenesulfonic acid. In some embodiments, the external acid is a surface modified acid selected from tartaric acid and succinic acid. In some embodiments, the pharmaceutically acceptable base is selected from sodium carbonate, potassium carbonate, sodium acetate, potassium acetate, sodium stearate, potassium stearate, lysine, arginine and histidine. In some embodiments, the pharmaceutically acceptable base is sodium carbonate. In some embodiments, a weight percent of external acid is about 2% to about 35%. In some embodiments, the external acid is present in the pharmaceutical composition in an amount of about 50 to about 300 mg. In some embodiments, the pharmaceutical composition exhibits a bioavailability that is at least 2-fold higher than a bioavailability of a corresponding formulation comprising the active pharmaceutical ingredient or a pharmaceutically acceptable salt thereof in a crystalline form, when measured as the total area under the curve (AUC) after oral administration or when measured as Cmax after oral administration. In some embodiments, the pharmaceutical composition exhibits a bioavailability that is at least 2-fold higher than a bioavailability of a reference pharmaceutical composition that comprises the active pharmaceutical ingredient or a pharmaceutically acceptable salt thereof, when measured as the total area under the curve (AUC) after oral administration or when measured as Cmax after oral administration, wherein the reference pharmaceutical composition does not comprise an amorphous solid dispersion. In some embodiments, the bioavailability is measured in a dog model in a fasted state or in a fed state. In some embodiments, a bioavailability of the pharmaceutical composition does not vary for more than 50% when orally administered in a fed state compared to a bioavailability administered in a fasted state, when measured as the total area under the curve (AUC) after oral administration or when measured as Cmax after oral administration. In some embodiments, the amorphous solid dispersion additionally comprises an inorganic acid or organic acid. In some embodiments, acid is selected from the group consisting of tartaric acid, fumaric acid, succinic acid, citric acid, lactic acid, malic acid, methanesulfonic acid, ethanesulfonic acid, isethionic acid, benzenesulfonic acid, p-toluenesulfonic acid, hydrochloric acid, sulfuric acid, and phosphoric acid. In some embodiments, the pharmaceutical composition is storage stable for at least 2 weeks, 1 month, 2 months, 3 months, 6 months, 12 months, or 24 months at 40 C°/75% RH, wherein a storage stable pharmaceutical composition has less than 100 ppm of a degradation product of the active pharmaceutical ingredient.

Disclosed herein is an amorphous solid dispersion, wherein the amorphous solid dispersion comprises: a) a lipophilic active pharmaceutical ingredient or a pharmaceutically acceptable salt thereof, wherein the active pharmaceutical ingredient has a log P in octanol-water equal or greater than 2.0; b) one or more surfactants, wherein the one or more surfactant is selected from polymeric non-ionic surfactants, and phospholipids, TPGS, and any combination thereof; c) a non-ionic hydrophilic polymer; and d) optionally an adsorbent. Disclosed herein is an amorphous solid dispersion, wherein the amorphous solid dispersion comprises: a) a lipophilic active pharmaceutical ingredient or a pharmaceutically acceptable salt thereof, wherein the active pharmaceutical ingredient has a log P in octanol-water equal or greater than 2.0; b) one or more surfactants, wherein the one or more surfactant comprise one or more non-ionic surfactants, one or more phospholipids, or any combination thereof; c) a non-ionic hydrophilic polymer; and d) optionally an adsorbent. In some embodiments, the active pharmaceutical ingredient or a pharmaceutically acceptable salt thereof is selected from nilotinib, abiraterone acetate, celecoxib, flurazepam, atorvastatin, indometacin, nortriptyline, loratadine, fluoxetine, diclofenac, clopidogrel, duloxetine, maprotiline, imipramine, amitriptyline, cyproheptadine, sertraline, flufenamic acid, chlorpromazine, miconazole, rimonabant, clofazimine, enzalutamide, lapatinib, pazopanib, erlotinib, dasatinib, gefitinib, sorafenib, axitinib, crizotinib, vemurafenib, telotristat ethyl, ivacaftor, nintedanib, ibrutinib, alectinib, bosutinib, lenvatinib, midostaurin, avapritinib, pexidartinib, alectinib, neratinib, enzalutamide, the corresponding free base thereof and pharmaceutically acceptable salts thereof. In some embodiments, the active pharmaceutical ingredient is a compound of Formula (I), or a N-oxide or a pharmaceutically acceptable salt thereof,

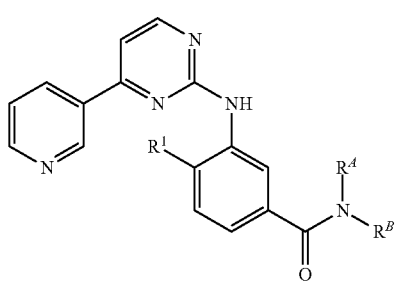

Formula (I)

wherein
- $R^1$ is hydrogen, $C_1$-$C_6$ alkyl, or halogen;
- $R^A$ is hydrogen, $C_1$-$C_6$ alkyl, $C_{1-6}$ alkoxy-$C_{1-6}$ alkyl, acyloxy-$C_{1-6}$ alkyl, carboxy-$C_{1-6}$ alkyl, $C_{1-6}$ alkoxycarbonyl-$C_{1-6}$ alkyl, or phenyl-$C_{1-6}$ alkyl,
- $R^B$ is hydrogen, $C_1$-$C_6$ alkyl, optionally and independently substituted by one or more $R^{10}$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or poly-substituted, wherein
- $R^{10}$ represents hydroxy, $C_1$-$C_6$ alkoxy, acyloxy, carboxy, $C_{1-6}$ alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted; or
- $R^A$ and $R^B$ taken together form a $C_4$-$C_6$ alkylene optionally mono- or disubstituted by $C_1$-$C_6$ alkyl, cycloalkyl, heterocyclyl, phenyl, hydroxy, $C_1$-$C_6$ alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by $C_1$-$C_6$ alkyl, phenyl-$C_1$-$C_6$ alkyl, $C_{1-6}$ alkoxycarbonyl-$C_{1-6}$ alkyl, carboxy-$C_{1-6}$ alkyl, carbamoyl-$C_{1-6}$ alkyl, N-mono- or N,N-disubstituted carbamoyl-$C_{1-6}$ alkyl, cycloalkyl, $C_{1-6}$ alkoxycarbonyl, carboxy, phenyl, substituted phenyl, pyridinyl, pyrimidinyl, or pyrazinyl.

In some embodiments, the active pharmaceutical ingredient or a pharmaceutically acceptable salt thereof is nilotinib or a pharmaceutically acceptable salt thereof. In some embodiments, the active pharmaceutical ingredient or a pharmaceutically acceptable salt thereof is nilotinib hydrochloride. In some embodiments, the active pharmaceutical ingredient or a pharmaceutically acceptable salt thereof is present in the amorphous solid dispersion in an amount of about 5 wt % to about 70 wt % based on solids. In some embodiments, the one or more surfactant is a polymeric non-ionic surfactant. In some embodiments, the polymeric non-ionic surfactant comprises a block copolymer of polyethylene glycol and polypropylene glycol. In some embodiments, the polymeric non-ionic surfactant is Poloxamer 188. In some embodiments, the one or more surfactants comprise one or more phospholipids. In some embodiments, the surfactant comprises lecithin. In some embodiments, the surfactant is present in the amorphous solid dispersion in an amount of about 5 wt % to about 70 wt % based on solids. In some embodiments, a weight ratio of the active pharmaceutical ingredient or a pharmaceutically acceptable salt thereof to the one or more surfactants is from about 10:1 to about 1:10. In some embodiments, the non-ionic hydrophilic polymer comprises polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-β-CD), hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof. In some embodiments, the non-ionic hydrophilic polymer is HPMC, PVP, HP-β-CD, PVA, HPMCAS, or PCL-PVAc-PEG. In some embodiments, the non-ionic hydrophilic polymer is present in the amorphous solid dispersion in an amount of about 5 wt % to about 70 wt % based on solids. In some embodiments, a weight ratio of the active pharmaceutical ingredient or a pharmaceutically acceptable salt thereof to the non-ionic hydrophilic polymer is from about 10:1 to about 1:10. In some embodiments, the adsorbent is selected from silicon dioxide, active carbon, magnesium aluminum silicate, diatomite, microcrystalline cellulose (MCC), silicified microcrystalline cellulose (SMCC), talc, crosslinked povidone, sodium carboxymethylcellulose, sodium carboxymethyl starch, and also sugars or sugar alcohols such as sorbitol, mannitol, lactose, cyclodextrin, and maltodextrin. In some embodiments, the adsorbent is silicon dioxide. In some embodiments, the adsorbent is present in the amorphous solid dispersion in an amount of about 10 to about 35% wt. In some embodiments, the average particle diameter of the amorphous solid dispersion is from 1 μm to 1000 μm. In some embodiments, an average particle size of the amorphous solid dispersion, in terms of particle diameter, is from about 10 μm to about 150 μm. In some embodiments, the amorphous solid dispersion additionally comprises an inorganic acid or organic acid. In some embodiments, the acid is selected from the group consisting of tartaric acid, fumaric acid, succinic acid, citric acid, lactic acid, malic acid, methanesulfonic acid, ethanesulfonic acid, isethionic acid, benzenesulfonic acid, p-toluenesulfonic acid, hydrochloric acid, sulfuric acid, and phosphoric acid. In some embodiments, the amorphous solid dispersion comprises: a) nilotinib free base or nilotinib HCl in an amount of about 5% to about 35% by weight; b) one or more surfactants in an amount of about 5% to about 50% by weight, wherein the one or more surfactants comprise lecithin, one or more non-ionic surfactants, or a combination thereof; c) a non-ionic hydrophilic polymer in an amount of about 1% to about 80% by weight, wherein the non-ionic hydrophilic polymer comprises polyvinyl alcohol (PVA), polyvinylpyrrolidone (PVP), hydroxypropyl methylcellulose (HPMC), or hydroxypropyl beta cyclodextrin (HP-β-

CD); and d) optionally an adsorbant in an amount of about 10% to 40% by weight. In some embodiments, the amorphous solid dispersion comprises: a) nilotinib free base or nilotinib HCl in an amount of about 5% to about 35% by weight; b) one or more surfactants in an amount of about 5% to about 50% by weight, wherein the one or more surfactants comprise lecithin, a block copolymer of polyethylene glycol and polypropylene glycol, TPGS, or a combination thereof; c) a non-ionic hydrophilic polymer in an amount of about 1% to about 80% by weight, wherein the non-ionic hydrophilic polymer comprises polyvinyl alcohol (PVA), polyvinylpyrrolidone (PVP), hydroxypropyl methylcellulose (HPMC), or hydroxypropyl beta cyclodextrin (HP-β-CD); and d) optionally silicone dioxide in an amount of about 10% to 40% by weight. In some embodiments, the pharmaceutical composition comprises: a) nilotinib free base or nilotinib HCl in an amount of about 15% to about 30% by weight; b) one or more surfactants in an amount of about 10% to about 40% by weight, wherein the one or more surfactants comprise lecithin, a block copolymer of polyethylene glycol and polypropylene glycol, TPGS, or a combination thereof; c) anon-ionic hydrophilic polymer in an amount of about 15% to about 60% by weight, wherein the non-ionic hydrophilic polymer comprises polyvinyl alcohol (PVA), polyvinylpyrrolidone (PVP), hydroxypropyl methylcellulose (HPMC), or hydroxypropyl beta cyclodextrin (HP-β-CD); and d) optionally silicone dioxide in an amount of about 15% to 35% by weight. In some embodiments, the pharmaceutical composition comprises: a) nilotinib free base or nilotinib HCl in an amount of about 15% to about 30% by weight; b) one or more surfactants in an amount of about 10% to about 40% by weight, wherein the one or more surfactants comprise lecithin, a block copolymer of polyethylene glycol and polypropylene glycol, TPGS, or a combination thereof; c) a non-ionic hydrophilic polymer in an amount of about 15% to about 60% by weight, wherein the non-ionic hydrophilic polymer comprises polyvinyl alcohol (PVA), polyvinylpyrrolidone (PVP), hydroxypropyl methylcellulose (HPMC), or hydroxypropyl beta cyclodextrin (HP-β-CD); and d) optionally silicone dioxide in an amount of about 15% to 35% by weight.

Disclosed herein is a method for preparing an amorphous solid dispersion, comprising the steps: a) combining (i) an active pharmaceutical ingredient or a pharmaceutically acceptable salt thereof, (ii) one or more surfactants, wherein the one or more surfactants comprise one or more phospholipids, one or more non-ionic surfactants, or any combination thereof, (iii) a non-ionic hydrophilic polymer, (iv) optionally an additive such as an adsorbent, and (v) a solvent, thereby producing a liquid mixture or solution, and b) removing the solvent from said mixture, thereby producing an amorphous solid dispersion. In some embodiments, the solvent is an organic solvent or a mixture of organic solvents. In some embodiments, the one or more surfactants are selected from non-ionic surfactants, TPGS, phospholipids, and any combination thereof. In some embodiments, the solvent is alcohol or contains alcohol. In some embodiments, the combining comprises dissolving the active pharmaceutical ingredient or a pharmaceutically acceptable salt thereof, the one or more surfactants, and the non-ionic hydrophilic polymer in the solvent. In some embodiments, the removing comprises spray-drying or rotor evaporation. In some embodiments, the removing comprises spraying of the solution onto an adsorbent and drying in a fluid bed equipment.

Disclosed herein is a method of treating a disease or condition, comprising administering to a subject in need thereof the pharmaceutical composition or the amorphous solid dispersions disclosed herein.

Disclosed herein is a method of treating cancer, comprising administering to a subject in need thereof the pharmaceutical compositions disclosed herein. In some embodiments, the cancer is a blood cancer. In some embodiments, the blood cancer is chronic myelogenous leukemia (CML). In some embodiments, the cancer is a solid tumor.

Disclosed herein is a method of inhibiting BCR-ABL tyrosine-kinase, comprising administering to a subject in need thereof the pharmaceutical compositions disclosed herein. In some embodiments, the subject is resistant to or intolerant to imatinib. In some embodiments, the method further comprises administering a chemotherapeutic agent. In some embodiments, the method further comprises administering a hematopoietic growth factor such as erythropoietin or G-CSF.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
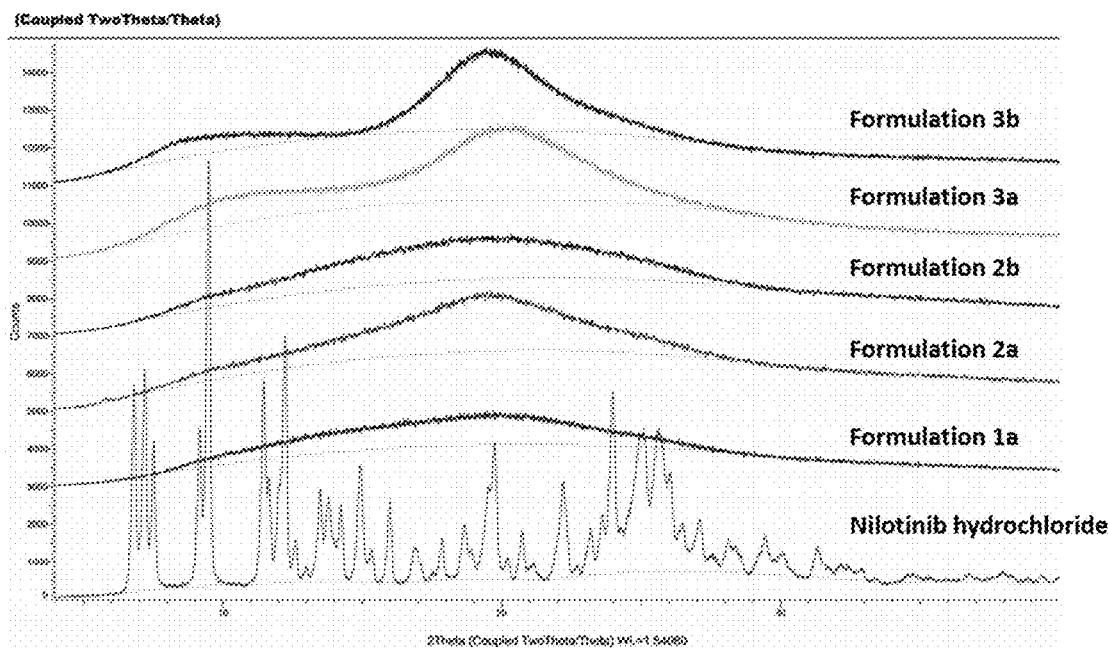
FIG. 1a and FIG. 1b shows X-ray powder diffraction studies for the amorphous solid dispersions of Formulations 1, 2a, 2b, 3a, 3b, 4, 5, 6, 7, 8, 9, and crystalline nilotinib hydrochloride.

The present invention is generally directed to compositions comprising pharmaceutically active agents that are useful as therapeutics that alleviate, abate or eliminate one or more conditions in a subject in need thereof, as further described herein. In particular, described herein are pharmaceutical compositions, their synthesis and use, where the pharmaceutical compositions comprise a lipophilic API, a hydrophilic polymer, and a surfactant in a combination such that the API has improved bioavailability compared to the API alone. In some embodiments, the lipophilic API, hydrophilic polymer, and the surfactant are in an amorphous solid dispersion.

Definitions

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The singular forms "a," "an," and, "the" include plural referents unless the context clearly dictates otherwise. Thus, for example, reference to "the surfactant" includes reference to one or more specific surfactants, reference to "an antioxidant" includes reference to one or more of such additives.

The term "subject" as used herein refers to a mammal (e.g., a human, mouse, rat, guinea pig, dog, cat, horse, cow, pig, or non-human primate, such as a monkey, chimpanzee or baboon).

"AUC" as used herein refers to the area under the plasma drug concentration-versus-time curve extrapolated from zero time to infinity. "$C_{max}$" as used herein refers to the highest drug concentration observed in plasma following an extravascular dose of drug. "$T_{max}$" as used herein refers to the time after administration of a drug when the maximum plasma concentration is reached.

"Effective amount," and "sufficient amount" may be used interchangeably, and refer to an amount of a substance that is sufficient to achieve an intended purpose or objective.

A "therapeutically effective amount" when used in connection with a pharmaceutical composition described herein is an amount of one or more pharmaceutically active agent(s) sufficient to produce a therapeutic result in a subject in need thereof.

"Therapeutically equivalent" when used in connection with a pharmaceutical composition described herein refers to an amount or quantity of a pharmaceutically acceptable salt or ester of a pharmaceutically active agent that is equivalent to the therapeutically effective amount of the free base or alcohol of the pharmaceutically active agent.

Amorphous Solid Dispersion

The present disclosure relates to pharmaceutical compositions and methods of administering thereof, the pharmaceutical compositions comprising an amorphous solid dispersion comprising a lipophilic API, hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, a solid dispersion is a solid state solution wherein an API (or API salt) and hydrophilic polymer act as solute and solvent, respectively. The solid dispersion can form multiple structures depending on the composition and sample processing history. When the API loading is lower than the equilibrium solubility of API in the hydrophilic polymer, the drug is molecularly dispersed within the polymer matrix and forms a thermodynamically stable, homogeneous solution. A homogenous solution is often attainable only at very low API loading and/or high temperature. For higher loadings, the mixture becomes a supersaturated solution and the drug precipitates out. This can result in a dispersion of crystalline API particles in a hydrophilic polymer matrix, in which the drug concentration corresponds to its equilibrium solubility at that temperature. Alternatively, as API crystallization can be a slow process, an intermediate meta-stable structure may form in which amorphous API aggregates are dispersed in a hydrophilic polymer matrix containing the API in a non-crystalline amorphous state. Such amorphous solid dispersions can provide superior dissolution properties, as compared to the crystalline API.

Amorphous solid dispersions described herein may comprise an API, hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants. In some embodiments, the amorphous solid dispersions described here are homogenous amorphous solid dispersions. In some embodiments, the components of the amorphous dispersion are mixed and heated in a solvent, and the solvent is removed to form the amorphous solid dispersion. In some embodiments, the solvent is water. In some embodiments, the solvent is a polar organic solvent. In some embodiments, the solvent is a non-polar organic solvent. In some embodiments, the solvent is selected from water, n-butanol, n-propanol, isopropanol, formic acid, nitromethane, ethanol, methanol, acetic acid, N-methylpyrrolidone, tetrahydrofuran, ethyl acetate, methyl acetate, dimethylformamide, acetonitrile, dimethyl sulfoxide, dichloromethane (DCM), acetone, tetrahydrofuran (THF), and any combination thereof. In some embodiments, the solvent is selected from water, n-butanol, n-propanol, isopropanol, formic acid, nitromethane, ethanol, methanol, acetic acid, and any combination thereof. In some embodiments, the solvent is selected from water, methanol, ethanol and isopropanol. In some embodiments, the solvent is selected from dichloromethane, methanol, THF, and acetone. In some embodiments, the solvent is selected from a mixture of these solvents.

Amorphous solid dispersions described herein may comprise an API, hydrophilic polymer, a surfactant and optionally, an adsorbent. In some embodiments, the components of the amorphous dispersion, such as API, hydrophilic polymer and surfactant are mixed and solubilized in a solvent, with or without heating to form a solution. In some embodiments, the adsorbent is further added into the solution to form a homogeneous suspension and the solvent is removed to form the amorphous solid dispersion. In some embodiments, the solution is sprayed on to the adsorbent and the solvent is removed to form the amorphous solid dispersion. In some embodiments, the adsorbent is selected from silicon dioxide (also termed silica), magnesium aluminometasilicate (Neusilin), microcrystalline cellulose (MCC), silicified microcrystalline cellulose (SMCC), talc, crosslinked povidone, sodium carboxymethylcellulose, sodium carboxymethylstarch, sugars, and sugar alcohols. In some embodiments, sugars and sugar slcohold comprise sorbitol, mannitol, lactose, cyclodextrin, and maltodextrin. In some embodiments, the adsorbent is silicon dioxide.

Active Pharmaceutical Ingredient (API)

Various embodiments described herein are directed to compositions comprising an effective amount of an active pharmaceutical agent (API). "Active pharmaceutical agent," "API," "drug," "pharmaceutically active agent," "bioactive agent," "therapeutic agent," and "active agent" and the like may be used interchangeably and refer to a substance, such as a chemical compound or complex, that has a measurable beneficial physiological effect on the body, such as a therapeutic effect in treatment of a disease or disorder, when administered in an effective amount. Further, when these terms are used, or when a particular active agent is specifically identified by name or category, it is understood that such recitation is intended to include the active agent per se, as well as pharmaceutically acceptable, pharmacologically active derivatives thereof, or compounds significantly related thereto, including without limitation, salts, pharmaceutically acceptable salts, N-oxides, prodrugs, active metabolites, isomers, fragments, analogs, solvates hydrates, radioisotopes, etc.

The partition-coefficient (P) as referenced herein is a ratio of concentrations of a compound between two immiscible solvent phases at equilibrium. Most commonly, one of the solvents is water and the other is hydrophobic, typically 1-octanol. The logarithm of the ratio is log P, as shown below, (conventionally the lipophilic phase is the numerator and hydrophilic phase is the denominator.)

$$\log P_{octanol/water} = \log \left( \frac{[\text{solute}]_{octan}}{[\text{solute}]_{water}} \right)$$

log P is a measure of lipophilicity or hydrophobicity. Hydrophobicity affects drug absorption, bioavailability, hydrophobic drug-receptor interactions, metabolism of molecules, and toxicity. Hydrophilic compounds are soluble in water ("water-loving") and polar solvents. Lipophilic compounds are less soluble in water ("water-fearing" or hydrophobic) and polar solvents, but are more soluble in organic solvents. Thus:

Low hydrophilicity = high lipophilicity = high log $P$ = poor aqueous solubility = poor absorption.

High hydrophilicity = low lipophilicity = low log $P$ = good aqueous solubility = good absorption.

Partition coefficients can be measured experimentally or estimated via calculation. Various methods for calculating (or predicting) log P have been developed, typically by fitting calculated log P values with experimentally measured log P values for training sets of thousands of molecules, mostly drug-like. Log P calculations are considered very robust and accurately process many organic molecules. For example, over 50% of molecules log P is predicted with error of less than 0.25, while over 80% with error of less than 0.5. Less than 3.5% of structures are predicted with an error greater 1.0. To distinguish from a measured log P, a calculated log P is sometimes written as clog P. Unless otherwise indicated, "log P" as used herein refers to an experimental log P value.

In some embodiments, the API is lipophilic. An API is considered lipophilic if its log P or calculated log P is 2.0 or higher. A log P of 2.0 or higher denotes that the solubility of the API is 100-fold or higher in a lipophilic solvent than in water. In some embodiments, the API is insoluble in polar solvents. In some embodiments, the API is insoluble in aqueous media. In some embodiments, the API is insoluble in water.

In some embodiments, the lipophilic API has a log P of at least 2.0, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0. Exemplary small molecule lipophilic API's include, without limitation, those listed in Table 1.

TABLE 1

| Name | Calculated log P | Experimental log P |
|---|---|---|
| Nilotinib | 5.8[4] | Not Available |
| Abiraterone Acetate | 5.1[2] | 5.12[3] |
| Chlordiazepoxide | 3.79[1] | 2.44[1] |
| Naringenin | 2.44[1] | 2.52[1] |
| Clofibric acid | 2.82[1] | 2.57[1] |
| Hesperetin | 2.29[1] | 2.60[1] |
| Cinchonidine | 2.49[1] | 2.6[1] |
| Quinine | 2.99[1] | 2.64[1] |
| Tramadol | 3.10[1] | 2.7[1] |
| Lormetazepam | 2.40[1] | 2.72[1] |
| Trazodone | 3.85[1] | 2.82[1] |
| Diltiazem | 3.65[1]; | 2.84[1] |
| Brompheniramine | 3.30[1]; | 2.88[1] |
| Alprenolol | 2.65[1]; | 2.89[1] |
| Propranolol | 2.75[1]; | 2.98[1] |
| Diazepam | 2.96[1]; | 2.99[1] |
| Apigenin | 2.91[1]; | 3.02[1] |
| Venlafaxine | 3.27[1]; | 3.05[1] |
| Rosiglitazone | 3.02[1]; | 3.1[1] |

TABLE 1-continued

| Name | Calculated log P | Experimental log P |
|---|---|---|
| Pyrilamine | 3.23[1]; | 3.12[1] |
| Quetiapine | 2.99[1]; | 3.13[1] |
| Ketoprofen | 2.76[1]; | 3.14[1] |
| Chlorphenamine | 3.15[1]; | 3.17[1] |
| Fenbufen | 3.14[1]; | 3.2[1] |
| Naproxen | 2.82[1]; | 3.24[1] |
| Warfarin | 2.90[1]; | 3.25[1] |
| Diphenhydramine | 3.45[1]; | 3.27[1] |
| Bupivacaine | 3.69[1]; | 3.41[1] |
| Clotiazepam | 3.03[1]; | 3.49[1] |
| Chrysin | 3.56[1]; | 3.52[1] |
| Valsartan | 3.63[1]; | 3.59[1] |
| Haloperidol | 3.85[1]; | 3.82[1] |
| Flurbiprofen | 3.75[1]; | 3.84[1] |
| Progesterone | 3.78[1]; | 3.87[1] |
| Celecoxib | 4.37[1]; | 3.91[1] |
| Flurazepam | 4.22[1]; | 3.94[1] |
| Glimepiride | 3.96[1]; | 3.97[1] |
| Ibuprofen | 3.68[1]; | 3.97[1] |
| Atorvastatin | 4.46[1]; | 4.08[1] |
| Indometacin | 4.18[1]; | 4.1[1] |
| Nortriptyline | 4.32[1]; | 4.36[1] |
| Loratadine | 5.05[1]; | 4.4[1] |
| Fluoxetine | 4.57[1]; | 4.42[1] |
| Diclofenac | 4.73[1]; | 4.5[1] |
| Clopidogrel | 4.21[1]; | 4.52[1] |
| Duloxetine | 4.26[1]; | 4.54[1] |
| Penbutolol | 3.64[1]; | 4.62[1] |
| Maprotiline | 4.52[1]; | 4.67[1] |
| Imipramine | 5.04[1]; | 4.8[1] |
| Amitriptyline | 4.85[1]; | 4.92[1] |
| Cyproheptadine | 5.30[1]; | 4.92[1] |
| Sertraline | 5.35[1]; | 5.17[1] |
| Flufenamic acid | 5.53[1]; | 5.19[1] |
| Chlorpromazine | 5.30[1]; | 5.27[1] |
| Miconazole | 5.81[1]; | 5.34[1] |
| Rimonabant | 6.47[1]; | 5.57[1] |
| Clofazimine | 7.70[1]; | 6.3[1] |
| Enzalutamide | 3.75[6]; | Not Available |
| lapatinib | 5.18[6]; | 5.4[5] |
| pazopanib | 3.59[6]; | Not Available |
| erlotinib | 3.2[6]; | 2.7[5] |
| dasatinib | 3.82[6]; | 1.8[5] |
| gefitinib | 3.75[6]; | 3.2[5] |
| sorafenib | 4.34[6]; | 3.8[5] |
| axitinib | 4.15[6]; | Not Available |
| crizotinib | 3.57[6]; | 1.83[5] |
| vemurafenib | 4.62[6]; | 5.1[5] |
| telotristat ethyl | 5.54[6]; | Not Available |
| ivacaftor | 5.76[6]; | 3.13[5] |
| nintedanib | 2.79[6]; | 3.0[5] |
| Ibrutinib | 3.63[6]; | 3.97[5] |
| alectinib | 5.59[2]; | Not Available |
| bosutinib | 4.09[6]; | Not Available |
| lenvatinib | 2.52[6]; | 3.30[5] |
| midostaurin | 5.43[6]; | 5.89[5] |
| ribociclib | 2.38[6]; | Not Available |
| avapritinib | 3.26[6]; | Not Available |
| pexidartinib | 4.54[6]; | Not Available |
| neratinib | 4.72[6]; | Not Available |
| enzalutamide | 3.75[6]; | Not Available |
| lurasidone | 5.4[6] | — |
| vilazodone | 3.72[6] | — |
| entrectinib | 4.56[6] | — |

[1] Pallicer, J. M., et al; *Evaluation of log $P_{o/w}$ values of drugs from some molecular structure calculation software*; Admet & DMPK 2(2) (2014) 107-114
[2] Calculation source—ALOGPS listed on www.drugbank.ca
[3] Experimental values listed on drug label
[4] Heimbach, T., et al.; *Physiologically Based Pharmacokinetic Modeling to Supplement Nilotinib Pharmacokinetics and Confirm Dose Selection in Pediatric Patients*; Journal of Pharmaceutical Sciences 108 (2019) 2191-2198
[5] Experimental values listed on www.drugbank.ca
[6] Calculation source—ChemAxon listed on www.drugbank.ca An acid dissociation constant, Ka, (or acidity constant) is a measure of the strength of an acid or base in solution, typically water. It is the equilibrium constant for the chemical dissociation of acids and bases. In aqueous solution, the equilibrium of acid dissociation is written:

$$HA + H_2O \rightleftharpoons A^- + H_3O^+$$

where HA is an acid that dissociates into $A^-$, (the conjugate base of the acid) and a hydrogen ion (which combines with a water molecule to make a hydronium ion, $H_3O^+$). The dissociation constant can also be written with the $H_2O$ removed:

$$HA \rightleftharpoons A \cdot + H^+$$
$$K_a = \frac{[A^-][H^+]}{[HA]}$$

The equilibrium of the dissociation of the conjugate acid of a base is written:

$$BH^+ + H_2O \rightleftharpoons B + H_3O^+$$

where $BH^+$ (the conjugate acid of the base) dissociates into B (the free base), and a hydrogen ion, which combines with a water molecule to form a hydronium ion, $H_3O^+$.
The dissociation constant can also be written with the $H_2O$ removed:

$$BH^+ \rightleftharpoons B + H^+$$
$$K_b = \frac{[B][H^+]}{[BH^+]}$$

$pK_a$, the logarithmic value of $K_a$, is more often used to express acid the strength/weakness of acids or the conjugate acid of bases:

$$pK_a = -\log_{10}(K_a)$$

The more positive the value of $pK_a$, the smaller the extent of dissociation, and the weaker the acid. In general, for acids:

$pK_a = -2$ to $12 \rightarrow$ weak acid (little or only partial dissociation in water)

$pKa < -2 \rightarrow$ strong acid (completly or mostly dissociated in water)

while for bases:

$pK_a < 12 \rightarrow$ weak base (little or only partial dissociation in water)

$pKa \geq 12 \rightarrow$ strong base (completly or mostly dissociated in water)

In some embodiments, the API is a weak base.
In some embodiments, the API comprises a weak base functional group.
In some embodiments, the API has a pKa of equal or greater than 3.0. In some embodiments, the API has a pKa of equal or greater than 3.5. In some embodiments, the API has a pKa of equal or greater than 4.0. In some embodiments, the API has a pKa of equal or greater than 4.5. In some embodiments, the API has a pKa of equal or greater than 5.0.

In some embodiments, the API is present in the form of a free base. In some embodiments, the API is present in the form of a pharmaceutically acceptable salt. As used herein, a pharmaceutically acceptable salt includes, but is not limited to, metal salts, such as sodium salts, potassium salts, and lithium salts; alkaline earth metals, such as calcium salts, magnesium salts, and the like; organic amine salts, such as triethylamine salts, pyridine salts, picoline salts, ethanolamine salts, triethanolamine salts, dicyclohexylamine salts, N,N'-dibenzylethylenediamine salts, and the like; inorganic acid salts such as hydrochloride salts, hydrobromide salts, sulfate salts, phosphate salts, and the like; organic acid salts such as formate salts, acetate salts, trifluoroacetate salts, maleate salts, tartrate salts, and the like; sulfonate salts such as methanesulfonate salts, benzenesulfonate salts, p-toluenesulfonate salts, and the like; and amino acid salts, such as arginate salts, asparginate salts, glutamate salts, and the like. In some embodiments the API is nilotinib or a pharmaceutically acceptable salt or ester thereof. In some embodiments, the API is nilotinib. In some embodiments, the API is a pharmaceutically acceptable salt of nilotinib. In some embodiments, the API is a lipophilic API. In some embodiments, the lipophilic API is one listed in Table 1, or a pharmaceutically acceptable salt thereof. In some embodiments, the lipophilic API, hydrophilic polymer, and the surfactant are formulated as an amorphous solid dispersion. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

Pharmaceutically acceptable salts include bitartrate, bitartrate hydrate, hydrochloride, p-toluenesulfonate, phosphate, sulfate, trifluoroacetate, bitartrate hemipentahydrate, pentafluoropropionate, hydrobromide, mucate, oleate, phosphate dibasic, phosphate monobasic, acetate trihydrate, bis (heptafuorobutyrate), bis(pentaflu oropropionate), bis (pyridine carboxylate), bis(trifluoroacetate), chlorhydrate, and sulfate pentahydrate. Other representative pharmaceutically acceptable salts include, e.g., water-soluble and water-insoluble salts, such as the acetate, amsonate(4,4-diaminostilbene-2,2-disulfonate), benzenesulfonate, benzonate, bicarbonate, bisulfate, bitartrate, borate, butyrate, calcium edetate, camphorsulfonate, camsylate, carbonate, citrate, clavulariate, dihydrochloride, edetate, edisylate, estolate, esylate, fiunarate, fumarate, gluceptate, gluconate, glutamate, glycollylarsanilate, hexafluorophosphate, hexylresorcinate, hydrabamine, hydrobromide, hydrochloride, hydroxynaphthoate, iodide, 26ydroxyapat, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A hydrate is another example of a pharmaceutically acceptable salt. In some embodiments the API is nilotinib or a pharmaceutically acceptable salt thereof. In some embodiments, the API is nilotinib. In some embodiments, the API is a pharmaceutically acceptable salt of nilotinib. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, the API has a low solubility at a pH of about 6-8. In some embodiments, the API has a solubility of less than 10 mg/ml in a solution with a pH of between about 6-8. In some embodiments, the API has a solubility of less than 1.0 mg/ml in a solution with a pH of between about 6-8. In some embodiments, the API has a solubility of less than 0.5 mg/ml in a solution with a pH of between about 6-8. In some embodiments, the API has a solubility of less than 0.1 mg/ml in a solution with a pH of between about 6-8. In some embodiments, the API has a solubility of less than 0.05 mg/ml in a solution with a pH of between about 6-8. In some embodiments, the API has a solubility of less than 0.04 mg/ml in a solution with a pH of between about 6-8. In some embodiments, the API has a solubility of less than 0.03 mg/ml in a solution with a pH of between about 6-8. In some embodiments, the API has a solubility of less than 0.02 mg/ml in a solution with a pH of between about 6-8. In some embodiments, the API has a solubility of less than 0.01 mg/ml in a solution with a pH of between about 6-8. In some embodiments, the API has a solubility of less than 0.001 mg/ml in a solution with a pH of between about 6-8. In some embodiments, the API has a low solubility at a pH of about 4-8. In some embodiments, the API has a solubility of less than 10 mg/ml in a solution with a pH of between about 4-8. In some embodiments, the API has a solubility of less than 1.0 mg/ml in a solution with a pH of between about 4-8. In some embodiments, the API has a solubility of less than 0.5 mg/ml in a solution with a pH of between about 4-8. In some embodiments, the API has a solubility of less than 0.1 mg/ml in a solution with a pH of between about 4-8. In some embodiments, the API has a solubility of less than 0.05 mg/ml in a solution with a pH of between about 4-8. In some embodiments, the API has a solubility of less than 0.04 mg/ml in a solution with a pH of between about 4-8. In some embodiments, the API has a solubility of less than 0.03 mg/ml in a solution with a pH of between about 4-8. In some embodiments, the API has a solubility of less than 0.02 mg/ml in a solution with a pH of between about 4-8. In some embodiments, the API has a solubility of less than 0.01 mg/ml in a solution with a pH of between about 4-8. In some embodiments, the API has a solubility of less than 0.001 mg/ml in a solution with a pH of between about 4-8. In some embodiments, the API has a low solubility at a pH of about 6-10. In some embodiments, the API has a solubility of less than 10 mg/ml in a solution with a pH of between about 6-10. In some embodiments, the API has a solubility of less than 1.0 mg/ml in a solution with a pH of between about 6-10. In some embodiments, the API has a solubility of less than 0.5 mg/ml in a solution with a pH of between about 6-10. In some embodiments, the API has a solubility of less than 0.1 mg/ml in a solution with a pH of between about 6-10. In some embodiments, the API has a solubility of less than 0.05 mg/ml in a solution with a pH of between about 6-10. In some embodiments, the API has a solubility of less than 0.04 mg/ml in a solution with a pH of between about 6-10. In some embodiments, the API has a solubility of less than 0.03 mg/ml in a solution with a pH of between about 6-10. In some embodiments, the API has a solubility of less than 0.02 mg/ml in a solution with a pH of between about 6-10. In some embodiments, the API has a solubility of less than 0.01 mg/ml in a solution with a pH of between about 6-10. In some embodiments, the API has a solubility of less than 0.001 mg/ml in a solution with a pH of between about 6-10. In some embodiments the API is nilotinib or a pharmaceutically acceptable salt thereof. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

Disclosed herein are pharmaceutical compositions comprising an API. In some embodiments, the API is present in the pharmaceutical composition in an amount of at least 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, or 200 mg. In some embodiments, the API is present in the pharmaceutical composition in an amount of about 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, or 200 mg. In some embodiments, the API is present in the pharmaceutical composition in an amount of no more than 1000 mg, 750 mg, 500 mg, 400 mg, 300 mg, 250 mg, 225 mg, 200 mg, 175 mg, 150 mg, 125 mg, 100 mg, 90 mg, 80 mg, 75 mg, 60 mg, 55 mg, or 50 mg. In some embodiments the API is nilotinib or a pharmaceutically acceptable salt thereof. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

Disclosed herein are pharmaceutical compositions comprising an API. In some embodiments, the API is present in the pharmaceutical composition in an amount of 10 mg to 1000 mg. In some embodiments, the API is present in an amount of 20 mg to 500 mg. In some embodiments, the API is present in an amount of 20 mg to 400 mg. In some embodiments, the API is present in an amount of 20 mg to 300 mg. In some embodiments, the API is present in an amount of 25 mg to 250 mg. In some embodiments, the API is present in an amount of 30 mg to 200 mg. In some embodiments, the API is present in an amount of about 50 mg, about 100 mg or about 150 mg. In some embodiments, the API is present in an amount of 50 mg, 100 mg or 150 mg. In some embodiments the API is nilotinib or a pharmaceutically acceptable salt thereof. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments a pharmaceutical composition is provided that comprises an active pharmaceutical ingredient that is present at a dose from about 1.0 mg to about 1000 mg, including but not limited to about 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, a pharmaceutical composition is provided that comprises nilotinib, or a pharmaceutically acceptable salt thereof, that is present at a dose from about 1.0 mg to about 1000 mg, including but not limited to about 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. In some embodiments, an amorphous solid dispersion includes a nilotinib, or a pharmaceutically acceptable salt thereof, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, a pharmaceutical composition is provided that comprises from about 1 mg to about 500 mg of the API. In some embodiments, a pharmaceutical composition is provided that comprises from about 10 mg to about 400 mg of the API. In some embodiments, a pharmaceutical composition is provided that comprises from about 25 mg to about 200 mg of the API. In some embodiments, a pharmaceutical composition is provided that comprises from about 50 mg to about 150 mg of the API. In some embodiments, a pharmaceutical composition is provided that comprises about 75 mg to about 125 mg of the API. In some embodiments, a pharmaceutical composition is provided that comprises from about 75 mg to about 100 mg of the API. In some embodiments, a pharmaceutical composition is provided that comprises from about 100 mg to about 125 mg of the API. In some embodiments the API is nilotinib or a pharmaceutically acceptable salt thereof. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, a pharmaceutical composition is provided that comprises from about 50 mg to about 150 mg of the API. In some embodiments, a pharmaceutical composition is provided that comprises from about 55 mg to about 150 mg of the API. In some embodiments, a pharmaceutical composition is provided that comprises from about 60 mg to about 150 mg of the API. In some embodiments, a pharmaceutical composition is provided that comprises from about 65 mg to about 150 mg of the API. In some embodiments, a pharmaceutical composition is provided that comprises from about 70 mg to about 150 mg of the API. In some embodiments, a pharmaceutical composition is provided that comprises from about 75 mg to about 150 mg of the API. In some embodiments, a pharmaceutical composition is provided that comprises from about 80 mg to about 150 mg of the API. In some embodiments, a pharmaceutical composition is provided that comprises from about 85 mg to about 150 mg of the API. In some embodiments, a pharmaceutical composition is provided that comprises from about 90 mg to about 150 mg of the API. In some embodiments, a pharmaceutical composition is provided that comprises from about 95 mg to about 150 mg of the API. In some embodiments, a pharmaceutical composition is provided that comprises from about 100 mg to about 150 mg of the API. In some embodiments, a pharmaceutical composition is provided that comprises from about 105 mg to about 150 mg of the API. In some embodiments, a pharmaceutical composition is provided that comprises from about 110 mg to about 150 mg of the API. In some embodiments, a pharmaceutical composition is provided that comprises from about 115 mg to about 150 mg of the API. In some embodiments, a pharmaceutical composition is provided that comprises from about 120 mg to about 150 mg of the API. In some embodiments, a pharmaceutical composition is provided that comprises from about 125 mg to about 150 mg of the API. In some embodiments, a pharmaceutical composition is provided that comprises from about 130 mg to about 150 mg of the API. In some embodiments, a pharmaceutical composition is provided that comprises from about 135 mg to about 150 mg of the API. In some embodiments, a pharmaceutical composition is provided that comprises from about 140 mg to about 150 mg of the API. In some embodiments, a pharmaceutical composition is provided that comprises from about 145 mg to about 150 mg of the API. In some embodiments, a pharmaceutical composition is provided that comprises from about 1 mg to about 50 mg of the API. In some embodiments, a pharmaceutical composition is provided that comprises from about 5 mg to about 40 mg of the API. In some embodiments, a pharmaceutical composition is provided that comprises from about 10 mg to about 30 mg of the API. In some embodiments, a pharmaceutical composition is provided that comprises from about 5 mg to about 25 mg of the API. In some embodiments, a pharmaceutical composition is provided that comprises from about 25 mg to about 50 mg of the API. In some embodiments, a pharmaceutical composition is provided that comprises from about 20 mg to about 40 mg of the API. In some embodiments, a pharmaceutical composition is provided that comprises from about 10 mg to about 25 mg of the API. In some embodiments, a pharmaceutical composition is provided that comprises from about 5 mg to about 20 mg of the API. In some embodiments, a pharmaceutical composition is provided that comprises from about 1 mg to about 10 mg of the API. In some embodiments, a pharmaceutical composition is provided that comprises from about 1 mg to about 20 mg of the API. In some embodiments the API is nilotinib or a pharmaceutically acceptable salt thereof. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, a pharmaceutical composition is provided that comprises from about 50 mg to about 145 mg of the API. In some embodiments, a pharmaceutical composition is provided that comprises from about 50 mg to about 140 mg of the API. In some embodiments, a pharmaceutical composition is provided that comprises from about 50 mg to about 135 mg of the API. In some embodiments, a pharmaceutical composition is provided that comprises from about 50 mg to about 130 mg of the API. In some embodiments, a pharmaceutical composition is provided that comprises from about 50 mg to about 125 mg of the API. In some embodiments, a pharmaceutical composition is provided that comprises from about 50 mg to about 120 mg of the API. In some embodiments, a pharmaceutical composition is provided that comprises from about 50 mg to about 115 mg of the API. In some embodiments, a pharmaceutical composition is provided that comprises from about 50 mg to about 110 mg of the API. In some embodiments, a pharmaceutical composition is provided that comprises from about 50 mg to about 105 mg of the API. In some embodiments, a pharmaceutical composition is provided that comprises from about 50 mg to about 100 mg of the API. In some embodiments, a pharmaceutical composition is provided that comprises from about 50 mg to about 95 mg of the API. In some embodiments, a pharmaceutical composition is provided that comprises from about 50 mg to about 90 mg of the API. In some embodiments, a pharmaceutical composition is provided that comprises from about 50 mg to about 85 mg of the API. In some embodiments, a pharmaceutical composition is provided that comprises from about 50 mg to about 80 mg of the API. In some embodiments, a pharmaceutical composition is provided that comprises from about 50 mg to about 75 mg of the API. In some embodiments, a pharmaceutical composition is provided that comprises from about 50 mg to about 70 mg of the API. In some embodiments, a pharmaceutical composition is provided that comprises from about 50 mg to about 65 mg of the API. In some embodiments, a pharmaceutical composition is provided that comprises from about 50 mg to about 60 mg of the API. In some embodiments, a pharmaceutical composition is provided that comprises from about 50 mg to about 55 mg of the API. In some embodiments, a pharmaceutical composition is provided that comprises from about 25 mg to about 50 mg of the API. In some embodiments, a pharmaceutical composition is provided that comprises from about 40 mg to about 80 mg of the API. In some embodiments, a pharmaceutical composition is provided that comprises from about 75 mg to about 125 mg of the API. In some embodiments, a pharmaceutical composition is provided that comprises an API in an amount of about 25 mg to about 200 mg. In some embodiments the API is nilotinib or a pharmaceutically acceptable salt thereof. In some embodiments the API is nilotinib HCl. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, the API comprises about 5%, 10%, 15%, 20%, 25%, 30%, 40%, or 50% of the total weight of the composition. In some embodiments the API is nilotinib or a pharmaceutically acceptable salt thereof. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, a pharmaceutical composition is provided that comprises from about 0.10% to about 99% by weight of the API. In some embodiments, a pharmaceutical composition is provided that comprises from about 0.1% to about 80% by weight of the API. In some embodiments, a pharmaceutical composition is provided that comprises from about 0.1% to about 60% by weight of the API. In some embodiments, a pharmaceutical composition is provided that comprises from about 0.1% to about 40% by weight of the API. In some embodiments, a pharmaceutical composition is provided that comprises from about 0.1% to about 20% by weight of the API. In some embodiments, a pharmaceutical composition is provided that comprises from about 0.1% to about 10% by weight of the API. In some embodiments, a pharmaceutical composition is provided that comprises from about 0.1% to about 1% by weight of the API. In some embodiments, a pharmaceutical composition is provided that comprises from about 20% to about 99% by weight of the API. In some embodiments, a pharmaceutical composition is provided that comprises from about 20% to about 80% by weight of the API. In some embodiments, a pharmaceutical composition is provided that comprises from about 20% to about 60% by weight of the API. In some embodiments, a pharmaceutical composition is provided that comprises from about 20% to about 40% by weight of the API. In some embodiments, a pharmaceutical composition is provided that comprises from about 30% to about 99% by weight of the API. In some embodiments, a pharmaceutical composition is provided that comprises from about 30% to about 80% by weight of the API. In some embodiments, a pharmaceutical composition is provided that comprises from about 30% to about 60% by weight of the API. In some embodiments, a pharmaceutical composition is provided that comprises from about 30% to about 40% by weight of the API. In some embodiments, a pharmaceutical composition is provided that comprises from about 40% to about 99% by weight of the API. In some embodiments, a pharmaceutical composition is provided that comprises from about 40% to about 80% by weight of the API. In some embodiments, a pharmaceutical composition is provided that comprises from about 40% to about 60% by weight of the API. In some embodiments, a pharmaceutical composition is provided that comprises from about 5% to about 70% by weight of the API. In some embodiments, a pharmaceutical composition is provided that comprises an API in a weight percent from about 5% to about 35%. In some embodiments, a pharmaceutical composition is provided that comprises an API in a weight percent from about 5% to about 10%, about 5% to about 15%, about 5% to about 18%, about 5% to about 19%, about 5% to about 20%, about 5% to about 21%, about 5% to about 22%, about 5% to about 24%, about 5% to about 25%, about 5% to about 30%, about 5% to about 35%, about 10% to about 15%, about 10% to about 18%, about 10% to about 19%, about 10% to about 20%, about 10% to about 21%, about 10% to about 22%, about 10% to about 24%, about 10% to about 25%, about 10% to about 30%, about 10% to about 35%, about 15% to about 18%, about 15% to about 19%, about 15% to about 20%, about 15% to about 21%, about 15% to about 22%, about 15% to about 24%, about 15% to about 25%, about 15% to about 30%, about 15% to about 35%, about 18% to about 19%, about 18% to about 20%, about 18% to about 21%, about 18% to about 22%, about 18% to about 24%, about 18% to about 25%, about 18% to about 30%, about 18% to about 35%, about 19% to about 20%, about 19% to about 21%, about 19% to about 22%, about 19% to about 24%, about 19% to about 25%, about 19% to about 30%, about 19% to about 35%, about 20% to about 21%, about 20% to about 22%, about 20% to about 24%, about 20% to about 25%, about 20% to about 30%, about 20% to about 35%, about 21% to about 22%, about 21% to about 24%, about 21% to about 25%, about 21% to about 30%, about 21% to about 35%, about 22% to about 24%, about 22% to about 25%, about 22% to about 30%, about 22% to about 35%, about 24% to about 25%, about 24% to about 30%, about 24% to about 35%, about 25% to about 30%, about 25% to about 35%, or about 30% to about 35%. In some embodiments, a pharmaceutical composition is provided that comprises an API in a weight percent from about 5%, about 10%, about 15%, about 18%, about 19%, about 20%, about 21%, about 22%, about 24%, about 25%, about 30%, or about 35%. In some embodiments, a pharmaceutical composition is provided that comprises an API in a weight percent from at least about 5%, about 10%, about 15%, about 18%, about 19%, about 20%, about 21%, about 22%, about 24%, about 25%, or about 30%. In some embodiments, a pharmaceutical composition is provided that comprises an API in a weight percent from at most about 10%, about 15%, about 18%, about 19%, about 20% about 21%, about 22%, about 24%, about 25%, about 30%, or about 35%. In some embodiments the API is nilotinib or a pharmaceutically acceptable salt thereof. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

The formation of the amorphous solid dispersion may require a specified particle size of the API. In some embodiments, the particle size of the API is from about 1 nm to 1 mm. In some embodiments, the particle size of the API is from about 0.01 to 1000 micrometers. In some embodiments, the particle size of the API is from about 0.01 micrometers to about 1,000 micrometers. In some embodiments, the particle size of the API is from at least about 0.01 micrometers. In some embodiments, the particle size of the API is from at most about 1,000 micrometers. In some embodiments, the particle size of the API is from about 1 micrometer to about 50 micrometers. In some embodiments, the particle size of the API is from at least about 1 micrometer. In some embodiments, the particle size of the API is from at most about 50 micrometers. In some embodiments, the particle size of the API is from about 1 micrometer to about 3 micrometers, about 1 micrometer to about 7 micrometers, about 1 micrometer to about 10 micrometers, about 1 micrometer to about 13 micrometers, about 1 micrometer to about 17 micrometers, about 1 micrometer to about 20 micrometers, about 1 micrometer to about 23 micrometers, about 1 micrometer to about 27 micrometers, about 1 micrometer to about 30 micrometers, about 1 micrometer to about 40 micrometers, about 1 micrometer to about 50 micrometers, about 10 micrometers to about 13 micrometers, about 10 micrometers to about 17 micrometers, about 10 micrometers to about 20 micrometers, about 10 micrometers to about 23 micrometers, about 10 micrometers to about 27 micrometers, about 10 micrometers to about 30 micrometers, about 10 micrometers to about 40 micrometers, about 10 micrometers to about 50 micrometers, about 20 micrometers to about 27 micrometers, about 20 micrometers to about 30 micrometers, about 20 micrometers to about 40 micrometers, about 20 micrometers to about 50 micrometers, about 30 micrometers to about 40 micrometers, about 30 micrometers to about 50 micrometers, or about 40 micrometers to about 50 micrometers. In some embodiments, the particle size of the API is from about 1 micrometer to about 100 micrometers. In some embodiments, the particle size of the API is from at least about 1 micrometer. In some embodiments, the particle size of the API is about 0.1, 1, 3, 5, 7, 10, 13, 17, 20, 23, 25, 27, 30, 33, 35, 37, 40, 43, 45, 47, 50, 60, 70, 80, 90, or 100 micrometers or less. In some embodiments, the particle size of the API is about 20 micrometers or less. In some embodiments the API is nilotinib or a pharmaceutically acceptable salt thereof. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, described herein is an amorphous solid dispersion that comprises an API such as nilotinib free base or a pharmaceutically acceptable salt thereof. In some embodiments, the amorphous solid dispersion is characterized by providing an amorphous powder X-ray diffraction pattern. In some embodiments, the nilotinib free base or a pharmaceutically acceptable salt thereof is present in the amorphous solid dispersion in an amount of about 5 wt % to about 70 wt % based on solids. In some embodiments, the nilotinib free base or a pharmaceutically acceptable salt thereof is present in the amorphous solid dispersion in an amount of about 10 wt % to about 50 wt % based on solids. In some embodiments, the nilotinib free base or a pharmaceutically acceptable salt thereof is present in the amorphous solid dispersion in an amount of about 20 wt % to about 40 wt % based on solids. In some embodiments, the nilotinib free base or a pharmaceutically acceptable salt thereof is present in the amorphous solid dispersion in an amount of about 10 wt % to about 30 wt % based on solids.

In some embodiments, an amorphous solid dispersion described herein comprises a surfactant. In some embodiments, the surfactant is selected from polymeric non-ionic surfactants and phospholipids. In some embodiments, the surfactant is a polymeric non-ionic surfactant. In some embodiments, the surfactant comprises a block copolymer of polyethylene glycol and polypropylene glycol. In some embodiments, the polymeric non-ionic surfactant has a number average molecular weight of from about 7,000 Da to about 10,000 Da. In some embodiments, an amorphous solid dispersion described herein comprises surfactant Poloxamer 188. In some embodiments, an amorphous solid dispersion described herein comprises a surfactant that comprises one or more phospholipids. In some embodiments, the surfactant comprises one or more of phosphatidylcholine, phosphatidylethanolamine, phosphatidylinositol, phosphatidylserine, plasmalogen, sphingomyelin, and phosphatidic acid. In some embodiments, the one or more phospholipids comprise greater than 50%, 60%, 70%, 80%, or 90% phosphatidylcholine by weight. In some embodiments, the surfactant comprises lecithin. In some embodiments, the surfactant is present in the amorphous solid dispersion in an amount of about 5 wt % to about 70 wt % based on solids. In some embodiments, the surfactant is present in the amorphous solid dispersion in an amount of about 20 wt % to about 60 wt % based on solids. In some embodiments, the surfactant is present in the amorphous solid dispersion in an amount of about 10 wt % to about 30 wt % based on solids. In some embodiments, a weight ratio of the nilotinib free base or a pharmaceutically acceptable salt thereof to the surfactant is from about 10:1 to about 1:10, or any ranges therebetween. In some embodiments, a weight ratio of the nilotinib free base or a pharmaceutically acceptable salt thereof to the surfactant is from about 5:1 to about 1:4. In some embodiments, a weight ratio of the nilotinib free base or a pharmaceutically acceptable salt thereof to the surfactant is from about 2:1 to about 1:2 In some embodiments, a weight ratio of the nilotinib free base or a pharmaceutically acceptable salt thereof to the surfactant is from about 1:1 to about 1:2 In some embodiments, a weight ratio of the nilotinib free base or a pharmaceutically acceptable salt thereof to the surfactant is from about 1:1 to about 1:1.5. In some embodiments, a weight ratio of the nilotinib free base or a pharmaceutically acceptable salt thereof to the surfactant is from about 0.5:1 to about 1:3 In some embodiments, a weight ratio of the nilotinib free base or a pharmaceutically acceptable salt thereof to the surfactant is from about 1:1 to about 1:3

In some embodiments, a pharmaceutical composition described herein comprises an active pharmaceutical ingredient or a salt thereof, such as nilotinib free base or a pharmaceutically acceptable salt thereof, a surfactant, and a non-ironic hydrophilic polymer. In some embodiments, the nilotinib free base or a pharmaceutically acceptable salt thereof is present in the pharmaceutical composition in an amount of about 10 mg to about 500 mg. In some embodiments, the nilotinib free base or a pharmaceutically acceptable salt thereof is present in the pharmaceutical composition in an amount of about 20 mg to about 200 mg. In some embodiments, the nilotinib free base or a pharmaceutically acceptable salt thereof is present in the pharmaceutical composition in an amount of about 25 mg, about 50 mg, about 100 mg about 150 mg, or about 200 mg. In some embodiments, the surfactant is present in the pharmaceutical composition in an amount of about 10 mg to about 500 mg. In some embodiments, the surfactant is present in the pharmaceutical composition in an amount of about 20 mg to about 200 mg. In some embodiments, the non-ionic hydrophilic polymer is present in the pharmaceutical composition in an amount of about 10 mg to about 500 mg. In some embodiments, the non-ionic hydrophilic polymer is present in the pharmaceutical composition in an amount of about 20 mg to about 200 mg.

In some embodiments, an amorphous solid dispersion described herein comprises a non-ionic hydrophilic polymer. In some embodiments the non-ionic hydrophilic polymer comprises polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), hydropropylmethylcellulose acetate succinate (HPMCAS), polyethylene glycol (PEG), polyvinyl acetate and polyvinylcaprolactame-based graft copolymer (PVAc-PVCap-PEG), or polyvinyl caprolactam-polyvinyl acetate-polyethylene glycol (PCL-PVAc-PEG also termed Soluplus®), polyethylene oxide, hydroxypropyl beta cyclodextrin (HP-β-CD), or a combination thereof. In some embodiments, the non-ionic hydrophilic polymer is HPMC, PVP, HP-β-CD, or PVA.

In some embodiments, the non-ionic hydrophilic polymer is present in the amorphous solid dispersion in an amount of about 5% to about 70%. In some embodiments, the non-ionic hydrophilic polymer is present in the amorphous solid dispersion in an amount of about 5% to about 10%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 5% to about 70%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 70%, about 20% to about 25%, about 20% to about 30%, about 20% to about 35%, about 20% to about 40%, about 20% to about 45%, about 20% to about 50%, about 20% to about 55%, about 20% to about 60%, about 20% to about 70%, about 25% to about 30%, about 25% to about 35%, about 25% to about 40%, about 25% to about 45%, about 25% to about 50% about 25% to about 55%, about 25% to about 60%, about 25% to about 70%, about 30% to about 35%, about 30% to about 40%, about 30% to about 45%, about 30% to about 50%, about 30% to about 55%, about 30% to about 60%, about 30% to about 70%, about 35% to about 40%, about 35% to about 45%, about 35% to about 50%, about 35% to about 55%, about 35% to about 60%, about 35% to about 70%, about 40% to about 45%, about 40% to about 50%, about 40% to about 55%, about 40% to about 60%, about 40% to about 70%, about 45% to about 50%, about 45% to about 55%, about 45% to about 60% about 45% to about 70%, about 50% to about 55%, about 50% to about 60%, about 50% to about 70%, about 55% to about 60%, about 55% to about 70%, or about 60% to about 70%. In some embodiments, the non-ionic hydrophilic polymer is present in the amorphous solid dispersion in an amount of about 5%, about 10%, about 20%, about 25%, about 30%, about 35%, about 40%, about 45%, about 50%, about 55%, about 60%, or about 70%. In some embodiments, the non-ionic hydrophilic polymer is present in the amorphous solid dispersion in an amount of at least about 5%, about 10%, about 20%, about 25%, about 30%, about 35%, about 40%, about 45%, about 50%, about 55%, or about 60%. In some embodiments, the non-ionic hydrophilic polymer is present in the amorphous solid dispersion in an amount of at most about 10%, about 20%, about 25%, about 30%, about 35%, about 40%, about 45%, about 50%, about 55%, about 60%, or about 70%.

In some embodiments, a weight ratio of the nilotinib free base or a pharmaceutically acceptable salt thereof to the non-ionic hydrophilic polymer is from about 1:1 to about 1:10. In some embodiments, a weight ratio of the nilotinib free base or a pharmaceutically acceptable salt thereof to the non-ionic hydrophilic polymer is from about 10:1 to about 8:1, about 10:1 to about 6:1, about 10:1 to about 4:1, about 10:1 to about 2:1, about 10:1 to about 1:1, about 10:1 to about 1:2, about 10:1 to about 1:4, about 10:1 to about 1:6, about 10:1 to about 1:8, about 10:1 to about 1:10, about 8:1 to about 6:1, about 8:1 to about 4:1, about 8:1 to about 2:1, about 8:1 to about 1:1, about 8:1 to about 1:2, about 8:1 to about 1:4, about 8:1 to about 1:6, about 8:1 to about 1:8, about 8:1 to about 1:10, about 6:1 to about 4:1, about 6:1 to about 2:1, about 6:1 to about 1:1, about 6:1 to about 1:2, about 6:1 to about 1:4, about 6:1 to about 1:6, about 6:1 to about 1:8, about 6:1 to about 1:10, about 4:1 to about 2:1, about 4:1 to about 1:1, about 4:1 to about 1:2, about 4:1 to about 1:4, about 4:1 to about 1:6, about 4:1 to about 1:8, about 4:1 to about 1:10, about 2:1 to about 1:1, about 2:1 to about 1:2, about 2:1 to about 1:4, about 2:1 to about 1:6, about 2:1 to about 1:8, about 2:1 to about 1:10, about 1:1 to about 1:2, about 1:1 to about 1:4, about 1:1 to about 1:6, about 1:1 to about 1:8, about 1:1 to about 1:10, about 1:2 to about 1:4, about 1:2 to about 1:6, about 1:2 to about 1:8, about 1:2 to about 1:10, about 1:4 to about 1:6, about 1:4 to about 1:8, about 1:4 to about 1:10, about 1:6 to about 1:8, about 1:6 to about 1:10, or about 1:8 to about 1:10. In some embodiments, a weight ratio of the nilotinib free base or a pharmaceutically acceptable salt thereof to the non-ionic hydrophilic polymer is from about 10:1, about 8:1, about 6:1, about 4:1, about 2:1, about 1:1, about 1:2, about 1:4, about 1:6, about 1:8, or about 1:10. In some embodiments, a weight ratio of the nilotinib free base or a pharmaceutically acceptable salt thereof to the non-ionic hydrophilic polymer is from at least about 10:1, about 8:1, about 6:1, about 4:1, about 2:1, about 1:1, about 1:2, about 1:4, about 1:6, or about 1:8. In some embodiments, a weight ratio of the nilotinib free base or a pharmaceutically acceptable salt thereof to the non-ionic hydrophilic polymer is from at most about 8:1, about 6:1, about 4:1, about 2:1, about 1:1, about 1:2, about 1:4, about 1:6, about 1:8, or about 1:10.

In some embodiments, an amorphous solid dispersion and/or a pharmaceutical composition described herein is free of organic acid. In some embodiments, the amorphous solid dispersion and/or the pharmaceutical composition is free of any acid.

A herein described amorphous solid dispersion can have a particle size distribution. In some embodiments, an average particle size of the amorphous solid dispersion, in terms of particle diameter, is from about 1 μm to about 500 μm. In some embodiments, an average particle size of the amorphous solid dispersion, in terms of particle diameter, is from about 1 μm to about 300 μm. In some embodiments, an average particle size of the amorphous solid dispersion, in terms of particle diameter, is from about 1 μm to about 20 μm. In some embodiments, an average particle size of the amorphous solid dispersion, in terms of particle diameter, is from about 5 μm to about 15 μm.

In some embodiments, a distribution of amorphous solid dispersion particle sizes is obtained. In some embodiments, the terms D10, D50, and D90 are used to describe a particle size distribution. The D10 diameter has ten percent of the particles smaller and ninety percent larger. D50 is the median diameter where fifty percent of the total mass of particles are larger and 50% are smaller. D90 defines the diameter where ninety percent of the distribution has a smaller particle diameter and ten percent has a larger particle diameter.

In some embodiments, an error-band is included. The term "total error band" is used herein to specify all sources of including sampling and sample preparation calculated at a 95% confidence level. An example is: D50 100 μm with a total error band of +/−5% on size. Other statistics are sometimes used to describe a particle size distribution. The most common calculations are standard deviation and variance. The standard deviation (St Dev.) specification defines the diameter where approximately 68.27% of the total population lies within +/−1 St Dev, and 95.45% lies within +/−2 St Dev.

In some embodiments, a distribution of amorphous solid dispersion particle sizes is obtained. In some embodiments, the terms D10, D50, and D90 are used to describe a particle size distribution. In some embodiments, the D90 particle size equal to or less than about 1,000 μm, 950 μm, 900 μm, 800 μm, 700 μm, 600 μm, 500 μm, 400 μm, 300 μm, 200 μm, 100 μm, 75 μm, 65 μm, 50 μm, 25 μm, 20 μm, 15 μm, or 10 μm. In some embodiments, the D50 particle size equal to or less than about 500 μm, 400 μm, 300 μm, 200 μm, 100 μm, 50 μm, 35 μm, 25 μm, 20 μm, 15 μm, 10 μm, or 5 μm. In some embodiments, the D10 particle size equal to or less than about 200 μm, 100 μm, 50 μm, 45 μm, 40 μm, 35 m, 30 μm, 25 m, 20 μm, 15 μm, 10 μm, 9 μm, 8 μm, 7 μm, 6 μm, 5 μm, 4 μm, 3 m, 2 μm, or 1 μm.

In some embodiments, a distribution of amorphous solid dispersion particle sizes is obtained. In some embodiments, the terms D10, D50, and D90 are used to describe a particle size distribution. In some embodiments, the D90 particle size is about 10 m to about 1,000 μm. In some embodiments, the D90 particle size is about 10 m to about 20 μm, about 10 μm to about 30 μm, about 10 m to about 50 μm, about 10 m to about 100 μm, about 10 μm to about 150 μm, about 10 μm to about 200 μm, about 10 μm to about 300 μm, about 10 μm to about 400 μm, about 10 μm to about 500 μm, about 10 μm to about 750 μm, about 10 μm to about 1,000 μm, about 20 μm to about 30 μm, about 20 μm to about 50 μm, about 20 μm to about 100 μm, about 20 μm to about 150 μm, about 20 μm to about 200 μm, about 20 μm to about 300 μm, about 20 μm to about 400 μm, about 20 μm to about 500 μm, about 20 μm to about 750 μm, about 20 m to about 1,000 μm, about 30 μm to about 50 μm, about 30 μm to about 100 μm, about 30 μm to about 150 μm, about 30 μm to about 200 μm, about 30 μm to about 300 μm, about 30 μm to about 400 μm, about 30 μm to about 500 μm, about 30 μm to about 750 μm, about 30 μm to about 1,000 μm, about 50 μm to about 100 μm, about 50 μm to about 150 μm, about 50 μm to about 200 μm, about 50 μm to about 300 μm, about 50 μm to about 400 μm, about 50 μm to about 500 μm, about 50 μm to about 750 μm, about 50 µm to about 1,000 µm, about 100 µm to about 150 µm, about 100 µm to about 200 µm, about 100 µm to about 300 µm, about 100 µm to about 400 µm, about 100 µm to about 500 µm, about 100 µm to about 750 µm, about 100 µm to about 1,000 µm, about 150 µm to about 200 µm, about 150 µm to about 300 µm, about 150 µm to about 400 µm, about 150 µm to about 500 µm, about 150 µm to about 750 µm, about 150 µm to about 1,000 µm, about 200 µm to about 300 µm, about 200 µm to about 400 µm, about 200 µm to about 500 µm, about 200 µm to about 750 µm, about 200 µm to about 1,000 µm, about 300 µm to about 400 µm, about 300 µm to about 500 µm, about 300 µm to about 750 µm, about 300 µm to about 1,000 µm, about 400 µm to about 500 µm, about 400 µm to about 750 µm, about 400 µm to about 1,000 µm, about 500 µm to about 750 µm, about 500 µm to about 1,000 µm, or about 750 µm to about 1,000 µm. In some embodiments, the D90 particle size is about 10 µm, about 20 µm, about 30 µm, about 50 µm, about 100 µm, about 150 µm, about 200 µm, about 300 µm, about 400 µm, about 500 µm, about 750 µm, or about 1,000 µm. In some embodiments, the D90 particle size is at least about 10 µm, about 20 µm, about 30 µm, about 50 µm, about 100 µm, about 150 µm, about 200 µm, about 300 µm, about 400 µm, about 500 µm, or about 750 µm. In some embodiments, the D90 particle size is at most about 20 µm, about 30 µm, about 50 µm, about 100 µm, about 150 µm, about 200 µm, about 300 µm, about 400 µm, about 500 µm, about 750 µm, or about 1,000 µm.

In some embodiments, a distribution of amorphous solid dispersion particle sizes is obtained. In some embodiments, the terms D10, D50, and D90 are used to describe a particle size distribution. In some embodiments, the D50 particle size is about 5 µm to about 100 µm. In some embodiments, the D50 particle size is about 5 µm to about 10 µm, about 5 µm to about 15 µm, about 5 µm to about 20 µm, about 5 µm to about 25 µm, about 5 µm to about 30 µm, about 5 µm to about 40 µm, about 5 µm to about 50 µm, about 5 µm to about 60 µm, about 5 µm to about 75 µm, about 5 µm to about 100 µm, about 10 µm to about 15 µm, about 10 µm to about 20 µm, about 10 µm to about 25 µm, about 10 µm to about 30 µm, about 10 µm to about 40 µm, about 10 µm to about 50 µm, about 10 µm to about 60 µm, about 10 µm to about 75 µm, about 10 µm to about 100 µm, about 15 µm to about 20 µm, about 15 µm to about 25 µm, about 15 µm to about 30 µm, about 15 µm to about 40 µm, about 15 µm to about 50 µm, about 15 µm to about 60 µm, about 15 µm to about 75 µm, about 15 µm to about 100 µm, about 20 µm to about 25 µm, about 20 µm to about 30 µm, about 20 µm to about 40 µm, about 20 µm to about 50 µm, about 20 µm to about 60 µm, about 20 µm to about 75 µm, about 20 µm to about 100 µm, about 25 µm to about 30 µm, about 25 µm to about 40 µm, about 25 µm to about 50 µm, about 25 µm to about 60 µm, about 25 µm to about 75 µm, about 25 µm to about 100 µm, about 30 µm to about 40 µm, about 30 µm to about 50 µm, about 30 µm to about 60 µm, about 30 µm to about 75 µm, about 30 µm to about 100 µm, about 40 µm to about 50 µm, about 40 µm to about 60 µm, about 40 µm to about 75 µm, about 40 µm to about 100 µm, about 50 µm to about 60 µm, about 50 µm to about 75 µm, about 50 µm to about 100 µm, about 60 µm to about 75 µm, about 60 µm to about 100 µm, or about 75 µm to about 100 µm. In some embodiments, the D50 particle size is about 5 µm, about 10 µm, about 15 µm, about 20 µm, about 25 µm, about 30 µm, about 40 µm, about 50 µm, about 60 µm, about 75 µm, or about 100 µm. In some embodiments, the D50 particle size is at least about 5 µm, about 10 µm, about 15 µm, about 20 µm, about 25 µm, about 30 µm, about 40 µm, about 50 µm, about 60 µm, or about 75 µm. In some embodiments, the D50 particle size is at most about 10 µm, about 15 µm, about 20 µm, about 25 µm, about 30 µm, about 40 µm, about 50 µm, about 60 µm, about 75 µm, or about 100 µm.

In some embodiments, a distribution of amorphous solid dispersion particle sizes is obtained. In some embodiments, the terms D10, D50, and D90 are used to describe a particle size distribution. In some embodiments, the D10 particle size is about 0.1 µm to about 50 µm. In some embodiments, the D10 particle size is about 0.1 µm to about 1 µm, about 0.1 µm to about 2 µm, about 0.1 µm to about 3 µm, about 0.1 µm to about 4 µm, about 0.1 µm to about 5 µm, about 0.1 µm to about 7 µm, about 0.1 µm to about 10 µm, about 0.1 µm to about 20 µm, about 0.1 µm to about 30 µm, about 0.1 µm to about 40 µm, about 0.1 µm to about 50 µm, about 1 µm to about 2 µm, about 1 µm to about 3 µm, about 1 µm to about 4 µm, about 1 µm to about 5 µm, about 1 µm to about 7 µm, about 1 µm to about 10 µm, about 1 µm to about 20 µm, about 1 µm to about 30 µm, about 1 µm to about 40 µm, about 1 µm to about 50 µm, about 2 µm to about 3 µm, about 2 µm to about 4 µm, about 2 µm to about 5 µm, about 2 µm to about 7 µm, about 2 µm to about 10 µm, about 2 µm to about 20 µm, about 2 µm to about 30 µm, about 2 µm to about 40 µm, about 2 µm to about 50 µm, about 3 µm to about 4 µm, about 3 µm to about 5 µm, about 3 µm to about 7 µm, about 3 µm to about 10 µm, about 3 µm to about 20 µm, about 3 µm to about 30 µm, about 3 µm to about 40 µm, about 3 µm to about 50 µm, about 4 µm to about 5 µm, about 4 µm to about 7 µm, about 4 µm to about 10 µm, about 4 µm to about 20 µm, about 4 µm to about 30 µm, about 4 µm to about 40 µm, about 4 µm to about 50 µm, about 5 µm to about 7 µm, about 5 µm to about 10 µm, about 5 µm to about 20 µm, about 5 µm to about 30 µm, about 5 µm to about 40 µm, about 5 µm to about 50 µm, about 7 µm to about 10 µm, about 7 µm to about 20 µm, about 7 µm to about 30 µm, about 7 µm to about 40 µm, about 7 µm to about 50 µm, about 10 µm to about 20 µm, about 10 µm to about 30 µm, about 10 µm to about 40 µm, about 10 µm to about 50 µm, about 20 µm to about 30 µm, about 20 µm to about 40 µm, about 20 µm to about 50 µm, about 30 µm to about 40 µm, about 30 µm to about 50 µm, or about 40 µm to about 50 µm. In some embodiments, the D10 particle size is about 0.1 µm, about 1 µm, about 2 µm, about 3 µm, about 4 µm, about 5 µm, about 7 µm, about 10 µm, about 20 µm, about 30 µm, about 40 µm, or about 50 µm. In some embodiments, the D10 particle size is at least about 0.1 µm, about 1 µm, about 2 µm, about 3 µm, about 4 µm, about 5 µm, about 7 µm, about 10 µm, about 20 µm, about 30 µm, or about 40 µm. In some embodiments, the D10 particle size is at most about 1 µm, about 2 µm, about 3 µm, about 4 µm, about 5 µm, about 7 µm, about 10 µm, about 20 µm, about 30 µm, about 40 µm, or about 50 µm.

In some embodiments, a distribution of amorphous solid dispersion particle sizes is obtained. In some embodiments, the terms D10, D50, and D90 are used to describe a particle size distribution. In some embodiments, D10 has a particle size range of about 0.1 to about 50 µm, D50 has a particle size range of about 5 to about 100 µm, and D90 has a particle size range of about 10 to about 600 µm. In some embodiments, D10 has a particle size range of about 2 to about 10 µm, D50 has a particle size range of about 5 to about 60 µm, and D90 has a particle size range of about 20 to about 250 µm. In some embodiments, D10 has a particle size range of about 2 to about 4 µm, D50 has a particle size range of about 5 to about 20 µm, and D90 has a particle size range of about 100 to about 300 µm. In some embodiments, D10 has a particle size range of about 2 to about 4 µm, D50 has a particle size range of about 5 to about 20 µm, and D90 has a particle size range of about 20 to about 50 µm. In some embodiments, D10 has a particle size range of about 0.1 to about 5 µm, D50 has a particle size range of about 2 to about 10 µm, and D90 has a particle size range of about 10 to about 35 µm.

Nilotinib

In some embodiments, the API is nilotinib or a pharmaceutically acceptable salt thereof. In some embodiments, the API is nilotinib hydrochloride.

In some embodiments, pharmaceutical compositions described herein have acceptable storage stability. In some embodiments, the pharmaceutical composition is storage stable for at least 2 weeks at 75° C./75% RH, wherein a storage stable pharmaceutical composition has less than 100 ppm of Impurity A at the end of the storage period. In some embodiments, the pharmaceutical composition is storage stable for at least 6 months at 40° C./75% RH, wherein a storage stable pharmaceutical composition has less than 100 ppm of Impurity A at the end of the storage period. In some embodiments, the pharmaceutical composition is storage stable for at least 2 weeks, 1 month, 2 months, 3 months, 6 months, 12 months, or 24 months at 40° C./75% RH, wherein a storage stable pharmaceutical composition has less than 100 ppm of Impurity A at the end of the storage period.

In some embodiments, pharmaceutical compositions described herein have superior bioavailability. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of a corresponding formulation comprising crystalline nilotinib, when measured as the total area under the curve (AUC) after oral administration. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of a corresponding formulation comprising crystalline nilotinib, when measured as $C_{max}$ after oral administration. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of TASIGNA® capsule comprising nilotinib HCl, when measured as the total area under the curve (AUC) after oral administration. In some embodiments, the pharmaceutical composition exhibits a bioavailability that is at least 1.1-fold, 1.2-fold, 1.3-fold, 1.4-fold, 1.5-fold, 1.6-fold, 1.7-fold, 1.8-fold, 1.9-fold, 2-fold, 2.5-fold, 3-fold, 3.5-fold, 4-fold, 4.5-fold, 5-fold, 5.5-fold, 6-fold, 7-fold, 8-fold, 9-fold, or 10-fold higher than a bioavailability of TASIGNA® capsule comprising nilotinib HCl, when measured as $C_{m}ax$ after oral administration. In some embodiments, the pharmaceutical composition exhibits a bioavailability that is higher than a bioavailability of TASIGNA® by about 1.1 fold to about 10 fold. In some embodiments, the pharmaceutical composition exhibits a bioavailability that is higher than a bioavailability of TASIGNA® by about 1.1 fold to about 2 fold, about 1.1 fold to about 3 fold, about 1.1 fold to about 4 fold, about 1.1 fold to about 5 fold, about 1.1 fold to about 6 fold, about 1.1 fold to about 7 fold, about 1.1 fold to about 8 fold, about 1.1 fold to about 10 fold, about 1.5 fold to about 2 fold, about 1.5 fold to about 3 fold, about 1.5 fold to about 4 fold, about 1.5 fold to about 5 fold, about 1.5 fold to about 6 fold, about 1.5 fold to about 7 fold, about 1.5 fold to about 8 fold, about 1.5 fold to about 10 fold, about 2 fold to about 4 fold, about 2 fold to about 5 fold, about 2 fold to about 6 fold, about 2 fold to about 7 fold, about 2 fold to about 8 fold, about 2 fold to about 10 fold, about 3 fold to about 4 fold, about 3 fold to about 5 fold, about 3 fold to about 6 fold, about 3 fold to about 7 fold, about 3 fold to about 8 fold, about 3 fold to about 10 fold, about 4 fold to about 5 fold, about 4 fold to about 6 fold, about 4 fold to about 7 fold, about 4 fold to about 8 fold, about 4 fold to about 10 fold, about 5 fold to about 6 fold, about 5 fold to about 7 fold, about 5 fold to about 8 fold, about 5 fold to about 10 fold, about 6 fold to about 7 fold, about 6 fold to about 8 fold, about 6 fold to about 10 fold, about 7 fold to about 8 fold, about 7 fold to about 10 fold, or about 8 fold to about 10 fold. In some embodiments, the pharmaceutical composition exhibits a bioavailability that is higher than a bioavailability of TASIGNA® by at least about 1.1 fold, about 1.3 fold, about 1.5 fold, about 1.8 fold, about 2 fold, about 3 fold, about 4 fold, about 5 fold, about 6 fold, about 7 fold, or about 8 fold. In some embodiments, the pharmaceutical composition exhibits a bioavailability that is higher than a bioavailability of TASIGNA® by at least about 2 fold. In some embodiments, the pharmaceutical composition exhibits a bioavailability that is higher than a bioavailability of TASIGNA® by at least about 4 fold. In some embodiments, the pharmaceutical composition exhibits a bioavailability that is higher than a bioavailability of TASIGNA® by at most about 1.3 fold, about 1.5 fold, about 1.8 fold, about 2 fold, about 3 fold, about 4 fold, about 5 fold, about 6 fold, about 7 fold, about 8 fold, or about 10 fold. In some embodiments, the bioavailability is measured in a dog model in a fasted state. In some embodiments, the bioavailability is measured in a dog model in a fed state. In some embodiments, a bioavailability of the pharmaceutical composition does not vary for more than 50%, 40%, 30%, 20%, 15%, or 10% when orally administered in a fed state compared to administered in a fasted state, when measured as the area under the total curve (AUC) after oral administration. In some embodiments, a bioavailability of the pharmaceutical composition does not vary for more than 50%, 40%, 30%, 20%, 15%, or 10% when orally administered in a fed state compared to administered in a fasted state, when measured as $C_{max}$ after oral administration. In some embodiments, a bioavailability of the pharmaceutical composition does not vary for more than 50% when orally administered in a fed state compared to administered in a fasted state. In some embodiments, a bioavailability of the pharmaceutical composition does not vary for more than 40% when orally administered in a fed state compared to administered in a fasted state. In some embodiments, a bioavailability of the pharmaceutical composition does not vary for more than 20% when orally administered in a fed state compared to administered in a fasted state.

In some embodiments, a pharmaceutical composition described herein comprises an amorphous solid dispersion. In some embodiments, the amorphous solid dispersion comprises an API. In some embodiments, the API is nilotinib or a pharmaceutically acceptable salt thereof. In some embodiments, the API is nilotinib hydrochloride. In some embodiments, the API is a compound of Formula (I), or a N-oxide or a pharmaceutically acceptable salt thereof,

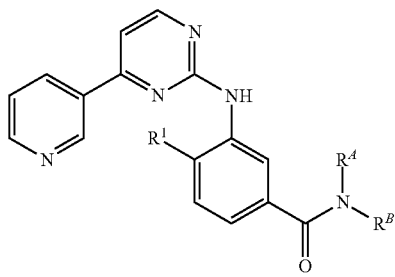

Formula (I)

wherein
R¹ is hydrogen, $C_1$-$C_6$ alkyl, or halogen;
$R^A$ is hydrogen, $C_1$-$C_6$ alkyl, $C_{1-6}$ alkoxy-$C_{1-6}$ alkyl, acyloxy-$C_{1-6}$ alkyl, carboxy-$C_{1-6}$ alkyl, $C_{1-6}$ alkoxycarbonyl-$C_{1-6}$ alkyl, or phenyl-$C_{1-6}$ alkyl,
$R^B$ is hydrogen, $C_1$-$C_6$ alkyl, optionally and independently substituted by one or more $R^{10}$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or poly-substituted, wherein
$R^{10}$ represents hydroxy, $C_1$-$C_6$ alkoxy, acyloxy, carboxy, $C_{1-6}$ alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted; or
$R^A$ and $R^B$ taken together form a $C_4$-$C_6$ alkylene optionally mono- or disubstituted by $C_1$-$C_6$ alkyl, cycloalkyl, heterocyclyl, phenyl, hydroxy, $C_1$-$C_6$ alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by $C_1$-$C_6$ alkyl, phenyl-$C_1$-$C_6$ alkyl, $C_{1-6}$ alkoxycarbonyl-$C_{1-6}$ alkyl, carboxy-$C_{1-6}$ alkyl, carbamoyl-$C_{1-6}$ alkyl, N-mono- or N,N-disubstituted carbamoyl-$C_{1-6}$ alkyl, cycloalkyl, $C_{1-6}$ alkoxycarbonyl, carboxy, phenyl, substituted phenyl, pyridinyl, pyrimidinyl, or pyrazinyl.

In some embodiments, the API is a compound of Formula (I), or a N-oxide or a pharmaceutically acceptable salt thereof, wherein:
R¹ is hydrogen, $C_1$-$C_6$ alkyl, or halogen;
$R^A$ is hydrogen, $C_1$-$C_6$ alkyl, $C_{1-6}$ alkoxy-$C_{1-6}$ alkyl, or benzyl;
$R^B$ is phenyl substituted by one or two substituents selected from the group consisting of $C_1$-$C_6$ alkyl, trifluoro-$C_{1-6}$ alkyl, hydroxy-$C_{1-6}$ alkyl, amino-$C_{1-6}$ alkyl, $C_{1-6}$ alkylamino-$C_{1-6}$ alkyl, di-$C_{1-6}$ alkylamino-$C_{1-6}$ alkyl, N-cyclohexyl-N-$_{1-6}$ alkylamino-$C_{1-6}$ alkyl, $C_{1-6}$ alkoxycarbonylpiperidino-$C_{1-6}$ alkyl, N—$C_{1-6}$ alkylpiperazino-$C_{1-6}$ alkyl, $C_{1-6}$ alkoxycarbonyl-$C_{1-6}$ alkyl, hydroxy, $C_1$-$C_6$ alkoxy, trifluoro-$C_{1-6}$ alkoxy, 1H-imidazolyl-$C_{1-6}$ alkoxy, $C_{1-6}$ alkanoyloxy, benzoyloxy, carboxy, $C_{1-6}$ alkoxycarbonyl, carbamoyl, $C_{1-6}$ alkylcarbamoyl, amino, $C_{1-6}$ alkanoylamino, benzoylamino, amino mono- or di-substituted by $C_1$-$C_6$ alkyl, by hydroxy-$C_{1-6}$ alkyl or by $C_{1-6}$ alkoxy-$C_{1-6}$ alkyl, 1H-imidazolyl, $C_{1-6}$ alkyl-1H-imidazolyl, carboxy-TH-imidazolyl, $C_{1-6}$ alkyl-estercarboxy-1H-imidazolyl, pyrrolidino, piperidino, piperazino, N—$C_{1-6}$ alkylpiperazino, morpholino, sulfamoyl, $C_{1-6}$ alkylsulfonyl, phenyl, pyridyl, halogenyl, or benzoyl.

In some embodiments, the API is a compound of Formula (I), or a pharmaceutically acceptable salt thereof, wherein:
R¹ is methyl;
$R^A$ is hydrogen;
$R^B$ is phenyl substituted by trifluoromethyl and optionally a further substituent selected from the group consisting of hydroxy-$C_{1-6}$ alkyl, $C_{1-6}$ alkylamino, hydroxy-$C_{1-6}$ alkylamino, di-$C_{1-6}$ alkylamino, 1H-imidazolyl, $C_{1-6}$ alkyl-1H-imidazolyl, carbamoyl, $C_{1-6}$ alkylcarbamoyl, pyrrolidino, piperidino, piperazino, $C_{1-6}$ alkylpiperazino, morpholino, $C_1$-$C_6$ alkoxy, trifluoro-$C_{1-6}$ alkoxy, phenyl, pyridyl, and halogenyl.

In some embodiments, the API is a compound of Formula (I), or a N-oxide or a pharmaceutically acceptable salt thereof, wherein:
R¹ is methyl;
$R^A$ is hydrogen;
$R^B$ is phenyl substituted by 5-trifluoromethyl and optionally a further substituent selected from the group consisting of 2-methyl-1H-imidazolyl, 4-methyl-1H-imidazolyl, 2,4-dimethyl-TH-imidazolyl, 5-methyl-1H imidazolyl, 2-methoxymethylamino, propoxy, ethoxy, methylaminocarbonyl, benzoyl, 4-methoxy-2-methyl, acetylamino 2,4-dimethyl-TH-imidazolyl, acetic acid ethyl ester, piperidine carboxylic acid ethyl ester.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The disclosure relates also to possible tautomers of the compounds of Formula (I).

Lower alkyl is preferably alkyl with from and including 1 up to and including 6, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Lower acyl is preferably formyl or lower alkylcarbonyl, in particular acetyl.

An aryl group is an aromatic radical which is bound to the molecule via a bond located at an aromatic ring carbon atom of the radical. In a preferred embodiment, aryl is an aromatic radical having 6 to 14 carbon atoms, especially phenyl, naphthyl, tetrahydronaphthyl, fluorenyl or phenanthrenyl, and is unsubstituted or substituted by one or more, preferably up to three, especially one or two substituents, especially selected from amino, mono- or disubstituted amino, halogen, lower alkyl, substituted lower alkyl, lower alkenyl, lower alkynyl, phenyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, dihydroxybora (—B(OH)2), heterocyclyl, a mono- or bicyclic heteroaryl group and lower alkylene dioxy bound at adjacent C-atoms of the ring, such as methylene dioxy. Aryl is more preferably phenyl, naphthyl or tetrahydronaphthyl, which in each case is either unsubstituted or independently substituted by one or two substituents selected from the group comprising halogen, especially fluorine, chlorine, or bromine; hydroxy; hydroxy etherified by lower alkyl, e.g. by methyl, by halogen-lower alkyl, e.g. trifluoromethyl, or by phenyl; lower alkylene dioxy bound to two adjacent C-atoms, e.g. methylenedioxy, lower alkyl, e.g. methyl or propyl; halogen-lower alkyl, e.g. trifluoromethyl; hydroxy-lower alkyl, e.g. hydroxymethyl or 2-hydroxy-2-propyl; lower alkoxy-lower alkyl; e.g. methoxymethyl or 2-methoxyethyl; lower alkoxycarbonyl-lower alkyl, e.g. methoxy-carbonylmethyl; lower alkynyl, such as 1-propynyl; esterified carboxy, especially lower alkoxycarbonyl, e.g. methoxycarbonyl, n-propoxy carbonyl or iso-propoxy carbonyl; N-mono-substituted carbamoyl, in particular carbamoyl monosubstituted by lower alkyl, e.g. methyl, n-propyl or iso-propyl; amino; lower alkylamino, e.g. methylamino; di-lower alkylamino, e.g. dimethylamino or diethylamino; lower alkylene-amino, e.g. pyrrolidino or piperidino; lower oxaalkylene-amino, e.g. morpholino, lower azaalkylene-amino, e.g. piperazino, acylamino, e.g. acetylamino or benzoylamino; lower alkylsulfonyl, e.g. methylsulfonyl; sulfamoyl; or phenylsulfonyl.

A cycloalkyl group is preferably cyclopropyl, cyclopentyl, cyclohexyl or cycloheptyl, and may be unsubstituted or substituted by one or more, especially one or two, substitutents selected from the group defined above as substitutents for aryl, most preferably by lower alkyl, such as methyl, lower alkoxy, such as methoxy or ethoxy, or hydroxy, and further by oxo or fused to a benzo ring, such as in benzcyclopentyl or benzcyclohexyl.

Substituted alkyl is alkyl as last defined, especially lower alkyl, preferably methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Mono- or disubstituted amino is especially amino substituted by one or two radicals selected independently of one another from lower alkyl, such as methyl; hydroxy-lower alkyl, such as 2-hydroxyethyl; lower alkoxy lower alkyl, such as methoxy ethyl; phenyl-lower alkyl, such as benzyl or 2-phenylethyl; lower alkanoyl, such as acetyl; benzoyl; substituted benzoyl, wherein the phenyl radical is especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino.

Disubstituted amino is also lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazino or N-methoxycarbonylpiperazino.

Halogen is especially fluorine, chlorine, bromine, or iodine, especially fluorine, chlorine, or bromine.

Etherified hydroxy is especially C8-C20 alkyloxy, such as n-decyloxy, lower alkoxy (preferred), such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic hetero-aryl comprising one or two nitrogen atoms, preferably lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

A mono- or bicyclic heteroaryl group comprising zero, one, two or three ring nitrogen atoms and zero or one oxygen atom and zero or one sulfur atom, which groups in each case are unsubstituted or mono- or polysubstituted, refers to a heterocyclic moiety that is unsaturated in the ring binding the heteroaryl radical to the rest of the molecule in formula I and is preferably a ring, where in the binding ring, but optionally also in any annealed ring, at least one carbon atom is replaced by a heteroatom selected from the group consisting of nitrogen, oxygen and sulfur; where the binding ring preferably has 5 to 12, more preferably 5 or 6 ring atoms; and which may be unsubstituted or substituted by one or more, especially one or two, substitutents selected from the group defined above as substituents for aryl, most preferably by lower alkyl, such as methyl, lower alkoxy, such as methoxy or ethoxy, or hydroxy. Preferably the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinnolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl and furanyl. More preferably the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, benzo[d]pyrazolyl, thienyl, and furanyl. In one preferred embodiment of the invention the pyridyl radical is substituted by hydroxy in ortho position to the nitrogen atom and hence exists at least partially in the form of the corresponding tautomer which is pyridin-(1H)2-one. In another preferred embodiment, the pyrimidinyl radical is substituted by hydroxy both in position 2 and 4 and hence exists in several tautomeric forms, e.g. as pyrimidine-(1H, 3H)2,4-dione.

Heterocyclyl is especially a five, six or seven-membered heterocyclic system with one or two heteroatoms selected from the group comprising nitrogen, oxygen, and sulfur, which may be unsaturated or wholly or partly saturated, and is unsubstituted or substituted especially by lower alkyl, such as methyl, phenyl-lower alkyl, such as benzyl, oxo, or heteroaryl, such as 2-piperazinyl; heterocyclyl is especially 2- or 3-pyrrolidinyl, 2-oxo-5-pyrrolidinyl, piperidinyl, N-benzyl-4-piperidinyl, N-lower alkyl-4-piperidinyl, N-lower alkyl-piperazinyl, morpholinyl, e.g. 2- or 3-morpholinyl, 2-oxo-1H-azepin-3-yl, 2-tetrahydrofuranyl, or 2-methyl-1,3-dioxolan-2-yl.

In some embodiments, salts of compounds of Formula (I) are formed, for example, as acid addition salts (e.g., with organic or inorganic acids), from compounds of formula I with a basic nitrogen atom, e.g., the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of Formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

Surfactants

In some embodiments, pharmaceutical compositions described herein include a lipophilic API, a hydrophilic polymer, and a surfactant. In some embodiments, pharmaceutical compositions described herein include a lipophilic API, a hydrophilic polymer, and one or more surfactants. In some embodiments, pharmaceutical compositions described herein include an amorphous solid dispersion comprising a lipophilic API, a hydrophilic polymer, and a surfactant. In some embodiments, pharmaceutical compositions described herein include an amorphous solid dispersion comprising a lipophilic API, a hydrophilic polymer, and one or more surfactants. In some embodiments, the API is an API of Table 1 or a pharmaceutically acceptable salt thereof. In some embodiments, the surfactants are compounds or mixture of compounds comprising a hydrophobic group (usually a hydrocarbon chain) and a hydrophilic group. They may perform one or more roles including solubility enhancer, bioavailability enhancer, stability enhancer, antioxidant and emulsifying agent. Other terms in the art for surfactants include emulsifier, emulsifying agent, surface-active agent, wetting agent, suspending agent and the like. Examples of surfactants include, but are not limited to, phospholipids, sucrose esters of fatty acids, polyoxyl stearate, polyoxyethylene hydrogenated castor oil, Polyoxyl 40 hydrogenated castor, macrogolglycerol hydroxystearate oil, PEG-40 castor oil, Kolliphor® RH40, polyoxyethylene polyoxypropylene glycol, sorbitan sesquioleate, sorbitan trioleate, sorbitan monostearate, sorbitan monopalmitate, sorbitan monolaurate, polysorbate, glyceryl monostearate, sodium lauryl sulfate, sodium dodecyl sulfate, lauromacrogol Arlasolve, Poloxamers, Labrafil, Labrasol, TWEEN® 80, Tocopheryl polyethylene glycol 1000 succinate (simply TPGS or Vitamin E TPGS) and the like. In some embodiments the API is nilotinib or a pharmaceutically acceptable salt thereof. In some embodiments, the API is nilotinib. In some embodiments, the API is a pharmaceutically acceptable salt of nilotinib. In some embodiments, the lipophilic API has a calculated log P or log P of at least 2.0. In some embodiments, the lipophilic API is one listed in Table 1, or a pharmaceutically acceptable salt thereof. In some embodiments, the lipophilic API, hydrophilic polymer, and the surfactant are formulated as an amorphous solid dispersion. The surfactant used in the present disclosure can be one or more non-ionic surfactant, one or more an ionic surfactant, or a mixture thereof. In some embodiments, a non-ionic surfactant has no charged groups in its head. Exemplary nonionic surfactants include, without limitation, fatty alcohols, cetyl alcohol, stearyl alcohol, cetostearyl alcohol, and oleyl alcohol. Exemplary nonionic surfactants include, but are not limited to, polyethylene glycol alkyl ethers (such as octaethylene glycol monododecyl ether, pentaethylene glycol monododecyl ether), polypropylene glycol alkyl ethers, glucoside alkyl ethers (such as decyl glucoside, lauryl glucoside, octyl glucoside), polyethylene glycol octylphenyl ethers (such as Triton™ X-100), polyethylene glycol alkylphenyl ethers (such as nonoxynol-9), glycerol alkyl esters (such as glyceryl laurate), polyoxyethylene glycol sorbitan alkyl esters (such as polysorbate), sorbitan alkyl esters (such as Spans), cocamide MEA, cocamide DEA, dodecyldimethylamine oxide, block copolymers of polyethylene glycol and polypropylene glycol (such as poloxamers), polyethoxylated tallow amine (POEA), and Tocopheryl polyethylene glycol 1000 succinate (simply TPGS or Vitamin E TPGS). In some embodiments, a non-ionic surfactant comprises one or more of fatty alcohols, cetyl alcohol, stearyl alcohol, cetostearyl alcohol, and oleyl alcohol. Exemplary nonionic surfactants include, but are not limited to, polyethylene glycol alkyl ethers (such as octaethylene glycol monododecyl ether, pentaethylene glycol monododecyl ether), polypropylene glycol alkyl ethers, glucoside alkyl ethers (such as decyl glucoside, lauryl glucoside, octyl glucoside), polyethylene glycol octylphenyl ethers (such as Triton™ X-100), polyethylene glycol alkylphenyl ethers (such as nonoxynol-9), glycerol alkyl esters (such as glyceryl laurate), polyoxyethylene glycol sorbitan alkyl esters (such as polysorbate), sorbitan alkyl esters (such as Spans), cocamide MEA, cocamide DEA, dodecyldimethylamine oxide, block copolymers of polyethylene glycol and polypropylene glycol (such as poloxamers), polyethoxylated tallow amine (POEA), and Tocopheryl polyethylene glycol 1000 succinate (simply TPGS or Vitamin E TPGS). In some embodiments, a non-ionic surfactant comprises Vitamin E, a block copolymer of polyethylene glycol and polypropylene glycol, or any combination thereof. In some embodiments, the surfactant comprises two more repeating units, such as polyoxyalkylene units. In some embodiments, the surfactant is a non-ionic surfactant that comprises polyethylene glycol. In some embodiments, the surfactant is a block copolymer of polyethylene glycol and polypropylene glycol. In some embodiments, the pharmaceutical composition or the amorphous solid dispersion comprises polysorbate (e.g, polysorbate 20, polysorbate 80). In some embodiments, the pharmaceutical composition or the amorphous solid dispersion comprises Tocopheryl polyethylene glycol succinate (TPGS). In some embodiments, the pharmaceutical composition or the amorphous solid dispersion comprises polyethylene glycol castor oil, such as PEG-40 castor oil. In some embodiments, the pharmaceutical composition or the amorphous solid dispersion comprises sorbitan oleate. In some embodiments, the pharmaceutical composition or the amorphous solid dispersion comprises two surfactants.

In some embodiments, an ionic surfactant has a charged group in its head. In some embodiments, an ionic surfactant is has an anionic head group or a cationic head group. In some embodiments, exemplary ionic surfactants include sodium lauryl sulfate, sodium dodecyl sulfate, calcium oleate, triethanolamine oleate, docusate sodium, benzalkonium chloride, and cetylpyridinium chloride. In some embodiments, the surfactant is a mixture of one or more non-ionic surfactants and one or more ionic surfactant.

In some embodiments, the non-ionic surfactant has a number average molecular weight of from about from about 1000 to about 100,000 Da, 2000 to about 20,000 Da, from about 4000 to about 15,000 Da, from about 6000 to about 12,000 Da, or from about 7000 to about 10,000 Da. In some embodiments, the non-ionic surfactant has a number average molecular weight of from about 7000 to about 10,000 Da. In some embodiments, the non-ionic surfactant has an ethylene glycol content of from about 30 wt % to about 99 wt %, from about 50 wt % to about 95 wt %, from about 60 wt % to about 95 wt %, from about 75 wt % to about 90 wt %, or from about 80 wt % to about 85 wt %. In some embodiments, the non-ionic surfactant has an ethylene glycol content of from about 80 wt % to about 85 wt %.

In some embodiments, the surfactants are selected from fatty acids, phospholipids, sphingolipids, saccharolipids, polyketides, sterol lipids, prenol lipids and the like. In some embodiments, phospholipids are made up of glycerol to which is attached a phosphate group and two fatty acids. Other terms in the art for phospholipids include glycerophospholipids, phosphoglycerides, diacylglycerides and the like. The phosphate group can be unmodified (i.e. in the structure below R=H) or modified by attachment (i.e. in the structure below R≠H) to simple organic molecules such as, but not limited to choline, ethanolamine or serine. Phospholipids may be further modified by substitution onto one or more for the hydrocarbon chains.

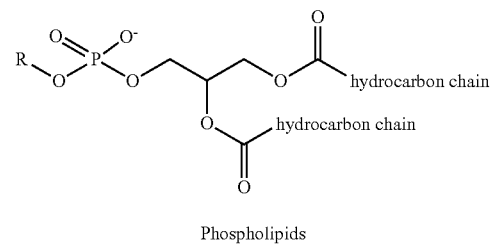

Phospholipids

Pharmaceutical compositions and amorphous solid dispersions described herein can comprise a phospholipid. In some embodiments, phospholipids are selected from glycerophospholipid, sphingolipid, and/or phospholipid derivatives. In some embodiments, glycerophospholipids include, but are not limited to phosphatidylcholine, phosphatidyl ethanolamine, phosphatidyl ethanolamine, phosphatidyl serine, phosphatidyl glycerol, diphosphatidylglycerol, phosphatidylinositol, and mixtures thereof. Phospholipid derivatives according to the present invention include, but are not limited to dioleoylphosphatidylcholine, dimyristoylphosphatidylcholine, dipentadeanoylphosphatidylcholine, dilauroylphosphatidylchoine, dipalmitoylphosphatidylcholine (DPPC), distearoylphosphatidylcholine (DSPC), diarachidonyiphosphatidylcholine (DAPC), dioleoylphosphatidylethanolamine, dipalmitoylphosphatidylethanolamine (DPPE), and distearoylphosphatidylethanolamine (DSPE), disteraoylphosphatidylglycerol (DSPG), phosphatidylinositol, dipalmitoylphosphatidic acid (DPPA), distearoylphosphatidic acid (DSPA), and the like, and mixtures thereof. In some embodiments, the phospholipids comprise at least 40%, 50%, 60%, 70%, 80%, 90%, or 95% phosphatidylcholine by weight. In some embodiments, the phospholipids comprise greater than 80% phosphatidylcholine.

In some embodiments, the phospholipid is present in the pharmaceutical composition in an amount of about 25 mg to about 200 mg. In some embodiments, the phospholipid is present in an amount of about 50 mg to 150 mg. In some embodiments, the phospholipids comprise 2.5%-20% of the total weight of the pharmaceutical composition. In some embodiments, the phospholipids comprise 5%-17% of the total weight of the pharmaceutical composition. In some embodiments, the phospholipids comprise greater than 80% phosphatidylcholine.

In some embodiments, phosphatidylcholines are phospholipids wherein a choline group ($Me_3N^+$—$CH_2$—$CH_2$—O—) is attached to the phosphate group.

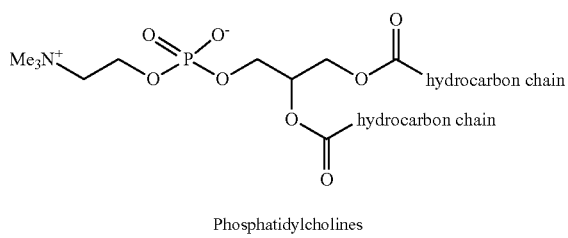

Phosphatidylcholines

Pharmaceutical compositions and amorphous solid dispersions described herein can comprise a phosphatidylcholine. A non-limiting example of a phosphatidylcholine is 1-oleoyl-2-palmitoyl-phosphatidyl choline, as shown below:

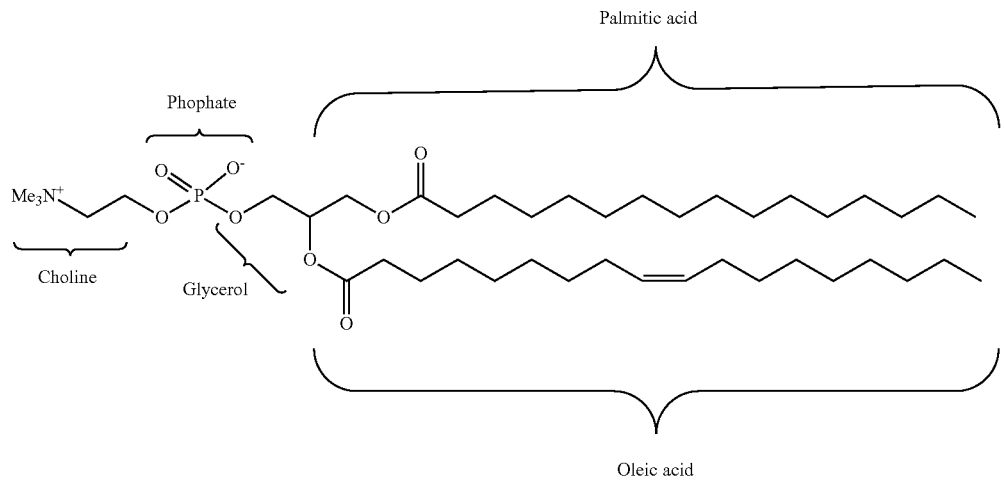

In some embodiments, the surfactant is lecithin. The USP 40 definition of lecithin is "a complex mixture of acetone-insoluble phosphatides, which consist chiefly of phophatidylcholine, phosphatidylethanolamine, phosphatilinositol, and phosphatidic acid, present in conjunction with various amounts of other substances such as triglycerides, fatty acids, and carbohydrates, as separated from the crude vegetable oil source." In some embodiments, lecithin is a mixture of phospholipids. Lecithins can be isolated from various sources including, but not limited to eggs, soybeans, milk, marine sources, rapeseed, cottonseed and sunflower. In some embodiments, the lecithin used in the disclosed amorphous solid dispersions and/or pharmaceutical compositions is isolated from egg yolk.

In some embodiments, the surfactant is a phospholipid. In some embodiments, the phospholipid is phosphatidylcholine. In some embodiments, the phospholipid is a mixture comprising phosphatidylcholine. In some embodiments, the surfactant is lecithin. In some embodiments, lecithin is a mixture of phospholipids. In some embodiments, the lecithin is comprised of phosphatidylcholine. In some embodiments, the lecithin contains more than 25% of phosphatidylcholine. In some embodiments, the lecithin contains more than 80% of phosphatidylcholine. In some embodiments, the phosphatidylcholine is from egg origin. In some embodiments, the phosphatidylcholine is from or soybean origin.

In some embodiments, the surfactant is present in an amorphous solid dispersion or in a pharmaceutical composition disclosed herein in an amount of about 25 mg to about 125 mg. In some embodiments, the surfactant is present in an amorphous solid dispersion or in a pharmaceutical composition disclosed herein in an amount of about 50 mg to about 100 mg In some embodiments, the surfactant is present in an amorphous solid dispersion or in a pharmaceutical composition disclosed herein in an amount of about 25 mg, about 50 mg, about 60 mg, about 70 mg, about 75 mg, about 80 mg, about 90 mg, about 100 mg, about 110 mg, about 120 mg, or about 125 mg. In some embodiments, the surfactant is present in an amorphous solid dispersion or in a pharmaceutical composition disclosed herein in an amount of at least about 25 mg, about 50 mg, about 60 mg, about 70 mg, about 75 mg, about 80 mg, about 90 mg, about 100 mg, about 110 mg, or about 120 mg. In some embodiments, the surfactant is present in an amorphous solid dispersion or in a pharmaceutical composition disclosed herein in an amount of at most about 50 mg, about 60 mg, about 70 mg, about 75 mg, about 80 mg, about 90 mg, about 100 mg, about 110 mg, about 120 mg, or about 125 mg. In some embodiments, the lecithin is present in an amount of 50 mg to 500 mg. In some embodiments, the lecithin is present in an amount of 75 mg to 300 mg. In some embodiments, the lecithin is present in an amount of 100 mg to 200 mg. In some embodiments, the lecithin is present in an amount of 125 mg to 175 mg. In some embodiments, the lecithin is present in an amount of about 50, 75, 100, 125, 150, 175, 200, 225, 250, 300, 350, 400, 450, or 500 mg. In some embodiments, the surfactant is or comprises a phospholipid. In some embodiments, the phospholipid is or comprises lecithin. In some embodiments, the surfactant is or comprises a poloxamer. In some embodiments, the surfactant is or comprises TPGS. In some embodiments, the surfactant is or comprises a non-ionic surfactant such as polysorbate (e.g, polysorbate 20, polysorbate 80), tocopheryl polyethylene glycol succinate (TPGS), polyethylene glycol castor oil (e.g., PEG-40 castor oil) and/or sorbitan oleate.

In some embodiments, the ratio by weight of the API to the surfactant is from about 2:1 to about 1:10. In some embodiments, the ratio by weight of the API to the surfactant is from about 1:0.5 to about 1:6. In some embodiments, the ratio by weight of the API to the surfactant is from about 1:0.8 to about 1:5. In some embodiments, the ratio by weight of the API to the surfactant is from about 1:0.8 to about 1:3.

In some embodiments, the ratio by weight of the API to the surfactant is from about 1:1 to about 1:3. In some embodiments, the ratio by weight of the API to the surfactant is from about 1:0.8 to about 1:2.8. In some embodiments, the ratio by weight of the API to the surfactant is from about 1:0.8 to about 1:2.5. In some embodiments, the ratio by weight of the API to the surfactant is from about 1:1 to about 1:2.5. In some embodiments, the ratio by weight of the API to the surfactant is from about 1:1 to about 1:2. In some embodiments, the ratio by weight of the API to the surfactant is from about 1:1 to about 1:1.5. In some embodiments, the ratio by weight of the API to the surfactant is from about 1:1 to about 1:4. In some embodiments, the ratio by weight of the API to the surfactant is from about 1:1 to about 1:3.5. In some embodiments, the surfactant is a phospholipid. In some embodiments, the phospholipid is lecithin. In some embodiments, the surfactant is a poloxamer. In some embodiments, the surfactant is TPGS.

In some embodiments, the surfactant is present in an amorphous solid dispersion in a weight percent of about 10% to about 40%. In some embodiments, the surfactant is present in an amorphous solid dispersion in a weight percent of about 15% to about 30% In some embodiments, the surfactant is present in an amorphous solid dispersion in a weight percent of about 10%, about 13%, about 14 m %, about 15%, about 16%, about 17%, about 18%, about 19%, about 20%, about 25%, about 30%, or about 40%. In some embodiments, the surfactant is present in an amorphous solid dispersion in a weight percent of at least about 10%, about 13%, about 14 m %, about 15%, about 16%, about 17%, about 18%, about 19%, about 20%, about 25%, about 30%, or about 40%. In some embodiments, the surfactant is present in an amorphous solid dispersion in a weight percent of at most about 10%, about 13%, about 14 m %, about 15%, about 16%, about 17%, about 18%, about 19%, about 20%, about 25%, about 30%, or about 40%. In some embodiments, the surfactant is a phospholipid. In some embodiments, the phospholipid is lecithin. In some embodiments, the surfactant is a poloxamer.

In some embodiments, the lecithin is present in an amorphous solid dispersion or in a pharmaceutical composition disclosed herein in an amount of no less than 5 mg, 10 mg, 15 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, or 250 mg. In some embodiments, the lecithin is present in an amorphous solid dispersion or in a pharmaceutical composition disclosed herein in an amount of about 5 mg, 10 mg, 15 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, or 250 mg. In some embodiments the API is nilotinib or a pharmaceutically acceptable salt thereof. In some embodiments, the API is nilotinib. In some embodiments, the API is a pharmaceutically acceptable salt of nilotinib. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

In some embodiments, the phospholipid is present in an amorphous solid dispersion or in a pharmaceutical composition disclosed herein in an amount of 50 mg to 500 mg. In some embodiments, the phospholipid is present in an amount of 75 mg to 300 mg. In some embodiments, the phospholipid is present in an amount of 100 mg to 200 mg. In some embodiments, the phospholipid is present in an amount of 125 mg to 175 mg. In some embodiments, the phospholipid is present in an amount of about 50, 75, 100, 125, 150, 175, 200, 225, 250, 300, 350, 400, 450, or 500 mg. In some embodiments, the phospholipid is present in an amorphous solid dispersion or in a pharmaceutical composition disclosed herein in an amount of no more than 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, 250 mg, 300 mg, or 500 mg. In some embodiments, the phospholipid is present in an amorphous solid dispersion or in a pharmaceutical composition disclosed herein in an amount of no less than 5 mg, 10 mg, 15 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, 250 mg.

In some embodiments, the phospholipid comprises 0.1%-50% of the total weight of a herein described composition. In some embodiments, the composition is an amorphous solid dispersion. In some embodiments, the composition is a pharmaceutical composition. In some embodiments, the phospholipid comprises 1%-30% of the total weight of the composition. In some embodiments, the composition is a pharmaceutical composition. In some embodiments, the phospholipid comprises 5%-20% of the total weight of the composition. In some embodiments, the phospholipid comprises 10%-17% of the total weight of the composition. In some embodiments, the phospholipid comprises about 15% of the total weight of the composition. In some embodiments, the phospholipid comprises about 16% of the total weight of the composition. In some embodiments, the phospholipid comprises about 17% of the total weight of the composition. In some embodiments, the ratio by weight of the hydrophilic polymer to lecithin is greater than 0.75. In some embodiments, the ratio by weight of the hydrophilic polymer to lecithin is greater than 1.0. In some embodiments, the ratio by weight of the hydrophilic polymer to lecithin is greater than 1.1. In some embodiments, the ratio by weight of the hydrophilic polymer to lecithin is greater 1.2. In some embodiments, the ratio by weight of the hydrophilic polymer to lecithin is greater 1.3. In some embodiments, the ratio by weight of the hydrophilic polymer to lecithin is greater 1.4. In some embodiments, the ratio by weight of the hydrophilic polymer to lecithin is greater than 1.5. In some embodiments, pharmaceutical compositions described herein include a lipophilic API, a hydrophilic polymer, and a surfactant. In some embodiments, pharmaceutical compositions described herein include a lipophilic API, a hydrophilic polymer, and a phospholipid or poloxamer. In some embodiments, pharmaceutical compositions described herein include a lipophilic API, a hydrophilic polymer, and lecithin. In some embodiments, pharmaceutical compositions described herein include a lipophilic API, a non-ionic hydrophilic polymer, and lecithin. In some embodiments the API is nilotinib or a pharmaceutically acceptable salt thereof. In some embodiments, the API is nilotinib. In some embodiments, the API is a pharmaceutically acceptable salt of nilotinib. In some embodiments, the API is a lipophilic API. In some embodiments, the lipophilic API is one listed in Table 1, or a pharmaceutically acceptable salt thereof. In some embodiments, the lipophilic API has a log P 2.0 or higher. In some embodiments, an amorphous solid dispersion includes a lipophilic API, a hydrophilic polymer, and a surfactant. In some embodiments, the amorphous solid dispersions described herein additionally comprise one or more adsorbents. In some embodiments, the amorphous solid dispersions described herein additionally comprise one or more other additives. In some embodiments, other additives comprise organic and inorganic acids. In some embodiments, other additives comprise antioxidants.

Hydrophilic Polymers

In some embodiments, pharmaceutical compositions described herein comprise a lipophilic API, a hydrophilic polymer, a surfactant, and optionally silicon dioxide. In some embodiments, the API is an API of Table 1 or a pharmaceutically acceptable salt thereof.

In some embodiments, pharmaceutical compositions described herein comprise a hydrophilic polymer. In some embodiments, the hydrophilic polymer comprises at least one of povidone, HPMC, PVP, polyvinylpolypyrrolidone (PVPP), Kollidon VA64 HP-b-CD, and PVA, hydropropylmethylcellulose acetate succinate (HPMCAS), and polyethylene glycol, polyvinyl acetate and polyvinylcaprolactame-based graft copolymer (PVAc-PVCap-PEG) or polyvinyl caprolactam-polyvinyl acetate-polyethylene glycol (PCL-PVAc-PEG, also termed Soluplus®). In some embodiments, PVP comprises PVP K30. In some embodiments, HMPC comprises HPMC E5 and HMPC E50.

In some embodiments, the hydrophilic polymer is present in an amorphous solid dispersion or in a pharmaceutical composition described herein in an amount of at least 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, or 200 mg. In some embodiments, the hydrophilic polymer is polyvinylpyrrolidone K30. In some embodiments, the hydrophilic polymer is crosslinked polyvinylpyrrolidone.

In some embodiments, the hydrophilic polymer is present in an amorphous solid dispersion or in a pharmaceutical composition described herein in an amount of about 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, or 250 mg. In some embodiments, the hydrophilic polymer is present in an amorphous solid dispersion or in a pharmaceutical composition described herein in an amount of no more than 1000 mg, 750 mg, 500 mg, 400 mg, 300 mg, 250 mg, 225 mg, 200 mg, 175 mg, 150 mg, 125 mg, 100 mg, 90 mg, 80 mg, 75 mg, 60 mg, 55 mg, or 50 mg. In some embodiments, the hydrophilic polymer is polyvinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone K30. In some embodiments, the hydrophilic polymer is polyvinylpyrrolidone VA64. In some embodiments, the hydrophilic polymer is polyvinylpyrrolidone HPMC. In some embodiments, the hydrophilic polymer is polyvinylpyrrolidone HPMC E5. In some embodiments, the hydrophilic polymer is polyvinylpyrrolidone HPMC E50.

In some embodiments, the hydrophilic polymer is present in an amorphous solid dispersion or in a pharmaceutical composition described herein in an amount of 10 mg to 1000 mg. In some embodiments, the hydrophilic polymer is present in an amount of 20 mg to 500 mg. In some embodiments, the hydrophilic polymer is present in an amount of 20 mg to 400 mg. In some embodiments, the hydrophilic polymer is present in an amount of 20 mg to 300 mg. In some embodiments, the hydrophilic polymer is present in an amount of 25 mg to 250 mg. In some embodiments, the hydrophilic polymer is present in an amount of 30 mg to 200 mg. In some embodiments, the hydrophilic polymer is present in an amount of about 50 mg, about 100 mg or about 150 mg. In some embodiments, the hydrophilic polymer is present in an amount of 50 mg, 100 mg or 150 mg. In some embodiments, the hydrophilic polymer is present in an amount of about 25 mg to about 200 mg. In some embodiments, the hydrophilic polymer is present in an amount of about 10 mg to about 400 mg. In some embodiments, the hydrophilic polymer is polyvinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone K30. In some embodiments, the hydrophilic polymer is polyvinylpyrrolidone VA64. In some embodiments, the hydrophilic polymer is polyvinylpyrrolidone HPMC. In some embodiments, the hydrophilic polymer is polyvinylpyrrolidone HPMC E5. In some embodiments, the hydrophilic polymer is polyvinylpyrrolidone HPMC E50.

In some embodiments a pharmaceutical composition is provided that comprises an hydrophilic polymer that is present at an amount from about 1.0 mg to about 1000 mg, including but not limited to about 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 326 mg, 326.5 mg, 327 mg, 327.5 mg, 328 mg, 328.5 mg, 329 mg, 329.5 mg, 330 mg, 330.5 mg, 331 mg, 331.5 mg, 332 mg, 332.5 mg, 333 mg, 333.5 mg, 334 mg, 334.5 mg, 335 mg, 335.5 mg, 336 mg, 336.5 mg, 337 mg, 337.5 mg, 338 mg, 338.5 mg, 339 mg, 339.5 mg, 340 mg, 340.5 mg, 341 mg, 341.5 mg, 342 mg, 342.5 mg, 343 mg, 343.5 mg, 344 mg, 344.5 mg, 345 mg, 345.5 mg, 346 mg, 346.5 mg, 347 mg, 347.5 mg, 348 mg, 348.5 mg, 349 mg, 349.5 mg, 350 mg, 350.5 mg, 351 mg, 351.5 mg, 352 mg, 352.5 mg, 353 mg, 353.5 mg, 354 mg, 354.5 mg, 355 mg, 355.5 mg, 356 mg, 356.5 mg, 357 mg, 357.5 mg, 358 mg, 358.5 mg, 359 mg, 359.5 mg, 360 mg, 360.5 mg, 361 mg, 361.5 mg, 362 mg, 362.5 mg, 363 mg, 363.5 mg, 364 mg, 364.5 mg, 365 mg, 365.5 mg, 366 mg, 366.5 mg, 367 mg, 367.5 mg, 368 mg, 369.5 mg, 370 mg, 370.5 mg, 371 mg, 371.5 mg, 372 mg, 372.5 mg, 373 mg, 373.5 mg, 374 mg, 374.5 mg, 375 mg, 375.5 mg, 376 mg, 376.5 mg, 377 mg, 377.5 mg, 378 mg, 378.5 mg, 379 mg, 379.5 mg, 380 mg, 380.5 mg, 381 mg, 381.5 mg, 382 mg, 382.5 mg, 383 mg, 383.5 mg, 384 mg, 384.5 mg, 385 mg, 385.5 mg, 386 mg, 386.5 mg, 387 mg, 387.5 mg, 388 mg, 388.5 mg, 389 mg, 389.5 mg, 390 mg, 390.5 mg, 391 mg, 391.5 mg, 392 mg, 392.5 mg, 393 mg, 393.5 mg, 394 mg, 394.5 mg, 395 mg, 395.5 mg, 396 mg, 396.5 mg, 397 mg, 397.5 mg, 398 mg, 398.5 mg, 399 mg, 399.5 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, or 1000 mg. In some embodiments, the composition is an amorphous solid dispersion. In some embodiments, the hydrophilic polymer polyvinylpyrrolidone or HPMC. In some embodiments, the hydrophilic polymer is PVP K30, PVP VA64, HMPC E5, or HMC E50

In some embodiments, a pharmaceutical composition is provided that comprises from about 1 mg to about 500 mg of the hydrophilic polymer. In some embodiments, a pharmaceutical composition is provided that comprises from about 10 mg to about 400 mg of the hydrophilic polymer. In some embodiments, a pharmaceutical composition is provided that comprises from about 25 mg to about 200 mg of the hydrophilic polymer. In some embodiments, a pharmaceutical composition is provided that comprises from about 50 mg to about 150 mg of the hydrophilic polymer. In some embodiments, a pharmaceutical composition is provided that comprises from about 75 mg to about 125 mg of the hydrophilic polymer. In some embodiments, a pharmaceutical composition is provided that comprises from about 75 mg to about 100 mg of the hydrophilic polymer. In some embodiments, a pharmaceutical composition is provided that comprises from about 100 mg to about 125 mg of the hydrophilic polymer. In some embodiments, the hydrophilic polymer is polyvinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone K30. In some embodiments, the hydrophilic polymer is polyvinylpyrrolidone VA64. In some embodiments, the hydrophilic polymer is polyvinylpyrrolidone HPMC. In some embodiments, the hydrophilic polymer is polyvinylpyrrolidone HPMC E5. In some embodiments, the hydrophilic polymer is polyvinylpyrrolidone HPMC E50. In some embodiments, the composition is an amorphous solid dispersion.

In some embodiments, a pharmaceutical composition is provided that comprises from about 50 mg to about 150 mg of the hydrophilic polymer. In some embodiments, a pharmaceutical composition is provided that comprises from about 55 mg to about 150 mg of the hydrophilic polymer. In some embodiments, a pharmaceutical composition is provided that comprises from about 60 mg to about 150 mg of the hydrophilic polymer. In some embodiments, a pharmaceutical composition is provided that comprises from about 65 mg to about 150 mg of the hydrophilic polymer. In some embodiments, a pharmaceutical composition is provided that comprises from about 70 mg to about 150 mg of the hydrophilic polymer. In some embodiments, a pharmaceutical composition is provided that comprises from about 75 mg to about 150 mg of the hydrophilic polymer. In some embodiments, a pharmaceutical composition is provided that comprises from about 80 mg to about 150 mg of the hydrophilic polymer. In some embodiments, a pharmaceutical composition is provided that comprises from about 85 mg to about 150 mg of the hydrophilic polymer. In some embodiments, a pharmaceutical composition is provided that comprises from about 90 mg to about 150 mg of the hydrophilic polymer. In some embodiments, a pharmaceutical composition is provided that comprises from about 95 mg to about 150 mg of the hydrophilic polymer. In some embodiments, a pharmaceutical composition is provided that comprises from about 100 mg to about 150 mg of the hydrophilic polymer. In some embodiments, a pharmaceutical composition is provided that comprises from about 105 mg to about 150 mg of the hydrophilic polymer. In some embodiments, a pharmaceutical composition is provided that comprises from about 110 mg to about 150 mg of the hydrophilic polymer. In some embodiments, a pharmaceutical composition is provided that comprises from about 115 mg to about 150 mg of the hydrophilic polymer. In some embodiments, a pharmaceutical composition is provided that comprises from about 120 mg to about 150 mg of the hydrophilic polymer. In some embodiments, a pharmaceutical composition is provided that comprises from about 125 mg to about 150 mg of the hydrophilic polymer. In some embodiments, a pharmaceutical composition is provided that comprises from about 130 mg to about 150 mg of the hydrophilic polymer. In some embodiments, a pharmaceutical composition is provided that comprises from about 135 mg to about 150 mg of the hydrophilic polymer. In some embodiments, a pharmaceutical composition is provided that comprises from about 140 mg to about 150 mg of the hydrophilic polymer. In some embodiments, a pharmaceutical composition is provided that comprises from about 145 mg to about 150 mg of the hydrophilic polymer. In some embodiments, the hydrophilic polymer is polyvinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone K30. In some embodiments, the hydrophilic polymer is polyvinylpyrrolidone VA64. In some embodiments, the hydrophilic polymer is polyvinylpyrrolidone HPMC. In some embodiments, the hydrophilic polymer is polyvinylpyrrolidone HPMC E5. In some embodiments, the hydrophilic polymer is polyvinylpyrrolidone HPMC E50. In some embodiments, the composition is an amorphous solid dispersion.

In some embodiments, the hydrophilic polymer comprises about 5% of the total weight of the composition. In some embodiments, the hydrophilic polymer comprises about 10% of the total weight of the composition. In some embodiments, the hydrophilic polymer comprises about 15% of the total weight of the composition. In some embodiments, the hydrophilic polymer comprises about 20% of the total weight of the composition. In some embodiments, the hydrophilic polymer comprises about 25% of the total weight of the composition. In some embodiments, the hydrophilic polymer comprises about 30% of the total weight of the composition. In some embodiments, the hydrophilic polymer comprises about 40% of the total weight of the composition. In some embodiments, the hydrophilic polymer comprises about 50% of the total weight of the composition. In some embodiments, the hydrophilic polymer is polyvinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone K30. In some embodiments, the hydrophilic polymer is polyvinylpyrrolidone VA64. In some embodiments, the hydrophilic polymer is polyvinylpyrrolidone HPMC. In some embodiments, the hydrophilic polymer is polyvinylpyrrolidone HPMC E5. In some embodiments, the hydrophilic polymer is polyvinylpyrrolidone HPMC E50. In some embodiments, the composition is an amorphous solid dispersion.

In some embodiments, a pharmaceutical composition is provided that comprises from about 0.10% to about 99% by weight of the hydrophilic polymer. In some embodiments, a pharmaceutical composition is provided that comprises from about 0.10% to about 80% by weight of the hydrophilic polymer. In some embodiments, a pharmaceutical composition is provided that comprises from about 0.10% to about 60% by weight of the hydrophilic polymer. In some embodiments, a pharmaceutical composition is provided that comprises from about 0.10% to about 40% by weight of the hydrophilic polymer. In some embodiments, a pharmaceutical composition is provided that comprises from about 0.10% to about 20% by weight of the hydrophilic polymer. In some embodiments, a pharmaceutical composition is provided that comprises from about 0.10% to about 10% by weight of the hydrophilic polymer. In some embodiments, a pharmaceutical composition is provided that comprises from about 0.10% to about 1% by weight of the hydrophilic polymer. In some embodiments, a pharmaceutical composition is provided that comprises from about 20% to about 99% by weight of the hydrophilic polymer. In some embodiments, a pharmaceutical composition is provided that comprises from about 20% to about 80% by weight of the hydrophilic polymer. In some embodiments, a pharmaceutical composition is provided that comprises from about 20% to about 60% by weight of the hydrophilic polymer. In some embodiments, a pharmaceutical composition is provided that comprises from about 20% to about 40% by weight of the hydrophilic polymer. In some embodiments, a pharmaceutical composition is provided that comprises from about 30% to about 99% by weight of the hydrophilic polymer. In some embodiments, a pharmaceutical composition is provided that comprises from about 30% to about 80% by weight of the hydrophilic polymer. In some embodiments, a pharmaceutical composition is provided that comprises from about 30% to about 60% by weight of the hydrophilic polymer. In some embodiments, a pharmaceutical composition is provided that comprises from about 30% to about 40% by weight of the hydrophilic polymer. In some embodiments, a pharmaceutical composition is provided that comprises from about 40% to about 99% by weight of the hydrophilic polymer. In some embodiments, a pharmaceutical composition is provided that comprises from about 40% to about 80% by weight of the hydrophilic polymer. In some embodiments, a pharmaceutical composition is provided that comprises from about 40% to about 60% by weight of the hydrophilic polymer. In some embodiments, the hydrophilic polymer is polyvinylpyrrolidone. In some embodiments, the composition is a herein described amorphous solid dispersion. In some embodiments, the composition is a herein described pharmaceutical composition.

The formation of the amorphous solid dispersion may require a specified particle size of the hydrophilic polymer. In some embodiments, the particle size of the hydrophilic polymer is from about 1 nm to 1 mm. In some embodiments, the particle size of the hydrophilic polymer is from about 0.01 to 1000 micrometers. In some embodiments, the particle size of the hydrophilic polymer is from about 0.01 micrometers to about 1,000 micrometers. In some embodiments, the particle size of the hydrophilic polymer is from at least about 0.01 micrometers. In some embodiments, the particle size of the hydrophilic polymer is from at most about 1,000 micrometers. In some embodiments, the particle size of the hydrophilic polymer is from about 1 micrometer to about 50 micrometers. In some embodiments, the particle size of the hydrophilic polymer is from at least about 1 micrometer. In some embodiments, the particle size of the hydrophilic polymer is from at most about 50 micrometers. In some embodiments, the particle size of the hydrophilic polymer is from about 1 micrometer to about 3 micrometers, about 1 micrometer to about 7 micrometers, about 1 micrometer to about 10 micrometers, about 1 micrometer to about 13 micrometers, about 1 micrometer to about 17 micrometers, about 1 micrometer to about 20 micrometers, about 1 micrometer to about 23 micrometers, about 1 micrometer to about 27 micrometers, about 1 micrometer to about 30 micrometers, about 1 micrometer to about 40 micrometers, about 1 micrometer to about 50 micrometers, about 10 micrometers to about 13 micrometers, about 10 micrometers to about 17 micrometers, about 10 micrometers to about 20 micrometers, about 10 micrometers to about 23 micrometers, about 10 micrometers to about 27 micrometers, about 10 micrometers to about 30 micrometers, about 10 micrometers to about 40 micrometers, about 10 micrometers to about 50 micrometers, about 20 micrometers to about 27 micrometers, about 20 micrometers to about 30 micrometers, about 20 micrometers to about 40 micrometers, about 20 micrometers to about 50 micrometers, about 30 micrometers to about 40 micrometers, about 30 micrometers to about 50 micrometers, or about 40 micrometers to about 50 micrometers. In some embodiments, the particle size of the hydrophilic polymer is from about 1 micrometer to about 100 micrometers. In some embodiments, the particle size of the hydrophilic polymer is from at least about 1 micrometer. In some embodiments, the particle size of the hydrophilic polymer is about 0.1, 1, 3, 5, 7, 10, 13, 17, 20, 23, 25, 27, 30, 33, 35, 37, 40, 43, 45, 47, 50, 60, 70, 80, 90, or 100 micrometers or less. In some embodiments, the particle size of the hydrophilic polymer is about 20 micrometers or less. In some embodiments, the hydrophilic polymer is polyvinylpyrrolidone (PVP) or hydroxypropyl methylcellulose HMPC. In some embodiments, the hydrophilic polymer is polyvinylpyrrolidone. In some embodiments, the hydrophilic polymer is polyvinylpyrrolidone K30. In some embodiments, the hydrophilic polymer is polyvinylpyrrolidone VA64. In some embodiments, the hydrophilic polymer is polyvinylpyrrolidone HPMC. In some embodiments, the hydrophilic polymer is polyvinylpyrrolidone HPMC E5. In some embodiments, the hydrophilic polymer is polyvinylpyrrolidone HPMC E50.

In some embodiments, a pharmaceutical composition comprises an amorphous solid dispersion. In some embodiments, the amorphous solid dispersion comprises a hydrophilic polymer in a weight percent of about 1% to about 90%. In some embodiments, the amorphous solid dispersion comprises a hydrophilic polymer in a weight percent of about 1% to about 80%. In some embodiments, the amorphous solid dispersion comprises a hydrophilic polymer in a weight percent of about 10% to about 60%. In some embodiments, the amorphous solid dispersion comprises a hydrophilic polymer in a weight percent of about 20% to about 50%. In some embodiments, the amorphous solid dispersion comprises a hydrophilic polymer in a weight percent of about 1%, about 10%, about 20%, about 30% about 35%, about 40%, about 45%, about 50%, about 55%, about 60%, about 80%, or about 90%. In some embodiments, the amorphous solid dispersion comprises a hydrophilic polymer in a weight percent of at least about 1%, about 10%, about 20%, about 30%, about 35%, about 40%, about 45%, about 50%, about 55%, about 60%, or about 80%. In some embodiments, the amorphous solid dispersion comprises a hydrophilic polymer in a weight percent of at most about 10%, about 20%, about 30%, about 35%, about 40%, about 45%, about 50%, about 55%, about 60%, about 80%, or about 90%.

Adsorbents

In some embodiments, pharmaceutical compositions described herein include a lipophilic API, a hydrophilic polymer, a surfactant and, optionally, an adsorbent. In some embodiments, the API is an API of Table 1 or a pharmaceutically acceptable salt thereof. Many adsorbents are solid, porous or super porous adsorption materials. They comprise numerous micro- or nano-pores within their structures, resulting in very large surface areas, for example, greater than 500 $m^2/g$. Exemplary adsorbents include, without limitation, silicon dioxide, active carbon, magnesium aluminum silicate, diatomite, microcrystalline cellulose (MCC), silicified microcrystalline cellulose (SMCC), talc, crosslinked povidone, sodium carboxymethylcellulose, sodium carboxymethyl starch, and also sugars or sugar alcohols such as sorbitol, mannitol, lactose, cyclodextrin, and maltodextrin. In some embodiments, the adsorbent is silicon dioxide.

In some embodiments, an adsorbent, such as silicon dioxide, is present in a pharmaceutical composition described herein in an amount of at least 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, or 200 mg. In some embodiments, the silicon dioxide is present in an amount of about 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, or 250 mg. In some embodiments, the silicon dioxide is present in an amount of no more than 1000 mg, 750 mg, 500 mg, 400 mg, 300 mg, 250 mg, 225 mg, 200 mg, 175 mg, 150 mg, 125 mg, 100 mg, 90 mg, 80 mg, 75 mg, 60 mg, 55 mg, 50 mg, or 25 mg. In some embodiments, the silicon dioxide is present in the amorphous solid dispersion.

In some embodiments, an adsorbent, such as silicon dioxide, is present in a pharmaceutical composition described herein in an amount from about 1.0 mg to about 1000 mg, including but not limited to about 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg. In some embodiments, the silicon dioxide is present in the amorphous solid dispersion.

In some embodiments, a pharmaceutical composition is provided that comprises from about 1 mg to about 500 mg of an adsorbent such, as silicon dioxide. In some embodiments, a pharmaceutical composition is provided that comprises from about 10 mg to about 400 mg of the adsorbent. In some embodiments, a pharmaceutical composition is provided that comprises from about 25 mg to about 200 mg of the adsorbent. In some embodiments, a pharmaceutical composition is provided that comprises from about 50 mg to about 150 mg of the adsorbent. In some embodiments, a pharmaceutical composition is provided that comprises from about 75 mg to about 125 mg of the adsorbent. In some embodiments, a pharmaceutical composition is provided that comprises from about 75 mg to about 100 mg of the adsorbent. In some embodiments, a pharmaceutical composition is provided that comprises from about 100 mg to about 125 mg of the adsorbent. In some embodiments, a pharmaceutical composition is provided that comprises from about 1 mg to about 200 mg of the adsorbent. In some embodiments, a pharmaceutical composition is provided that comprises from about 25 mg to about 200 mg of the adsorbent. In some embodiments, a pharmaceutical composition is provided that comprises from about 50 mg to about 200 mg of the adsorbent. In some embodiments, a pharmaceutical composition is provided that comprises from about 50 mg to about 150 mg of the adsorbent. In some embodiments, a pharmaceutical composition is provided that comprises from about 75 mg to about 125 mg of the adsorbent. In some embodiments, a pharmaceutical composition is provided that comprises from about 75 mg to about 100 mg of the adsorbent. In some embodiments, a pharmaceutical composition is provided that comprises from about 100 mg to about 125 mg of the adsorbent. In some embodiments, a pharmaceutical composition is provided that comprises from about 50 mg to about 150 mg of the adsorbent. In some embodiments, a pharmaceutical composition is provided that comprises from about 55 mg to about 150 mg of the adsorbent. In some embodiments, a pharmaceutical composition is provided that comprises from about 60 mg to about 150 mg of the adsorbent. In some embodiments, a pharmaceutical composition is provided that comprises from about 65 mg to about 150 mg of the adsorbent. In some embodiments, a pharmaceutical composition is provided that comprises from about 70 mg to about 150 mg of the adsorbent. In some embodiments, a pharmaceutical composition is provided that comprises from about 75 mg to about 150 mg of the adsorbent. In some embodiments, a pharmaceutical composition is provided that comprises from about 80 mg to about 150 mg of the adsorbent. In some embodiments, a pharmaceutical composition is provided that comprises from about 85 mg to about 150 mg of the adsorbent. In some embodiments, a pharmaceutical composition is provided that comprises from about 90 mg to about 150 mg of the adsorbent. In some embodiments, a pharmaceutical composition is provided that comprises from about 95 mg to about 150 mg of the adsorbent. In some embodiments, a pharmaceutical composition is provided that comprises from about 100 mg to about 150 mg of the adsorbent. In some embodiments, a pharmaceutical composition is provided that comprises from about 105 mg to about 150 mg of the adsorbent. In some embodiments, a pharmaceutical composition is provided that comprises from about 110 mg to about 150 mg of the adsorbent. In some embodiments, a pharmaceutical composition is provided that comprises from about 115 mg to about 150 mg of the adsorbent. In some embodiments, a pharmaceutical composition is provided that comprises from about 120 mg to about 150 mg of the adsorbent. In some embodiments, a pharmaceutical composition is provided that comprises from about 125 mg to about 150 mg of the adsorbent. In some embodiments, a pharmaceutical composition is provided that comprises from about 130 mg to about 150 mg of the adsorbent. In some embodiments, a pharmaceutical composition is provided that comprises from about 135 mg to about 150 mg of the adsorbent. In some embodiments, a pharmaceutical composition is provided that comprises from about 140 mg to about 150 mg of the adsorbent. In some embodiments, a pharmaceutical composition is provided that comprises from about 145 mg to about 150 mg of the adsorbent. In some embodiments, a pharmaceutical composition is provided that comprises from about 50 mg to about 145 mg of the adsorbent. In some embodiments, a pharmaceutical composition is provided that comprises from about 50 mg to about 140 mg of the adsorbent. In some embodiments, a pharmaceutical composition is provided that comprises from about 50 mg to about 135 mg of the adsorbent. In some embodiments, a pharmaceutical composition is provided that comprises from about 50 mg to about 130 mg of the adsorbent. In some embodiments, a pharmaceutical composition is provided that comprises from about 50 mg to about 125 mg of the adsorbent. In some embodiments, a pharmaceutical composition is provided that comprises from about 50 mg to about 120 mg of the adsorbent. In some embodiments, a pharmaceutical composition is provided that comprises from about 50 mg to about 115 mg of the adsorbent. In some embodiments, a pharmaceutical composition is provided that comprises from about 50 mg to about 110 mg of the adsorbent. In some embodiments, a pharmaceutical composition is provided that comprises from about 50 mg to about 105 mg of the adsorbent. In some embodiments, a pharmaceutical composition is provided that comprises from about 50 mg to about 100 mg of the adsorbent. In some embodiments, a pharmaceutical composition is provided that comprises from about 50 mg to about 95 mg of the adsorbent. In some embodiments, a pharmaceutical composition is provided that comprises from about 50 mg to about 90 mg of the adsorbent. In some embodiments, a pharmaceutical composition is provided that comprises from about 50 mg to about 85 mg of the adsorbent. In some embodiments, a pharmaceutical composition is provided that comprises from about 50 mg to about 80 mg of the adsorbent. In some embodiments, a pharmaceutical composition is provided that comprises from about 50 mg to about 75 mg of the adsorbent. In some embodiments, a pharmaceutical composition is provided that comprises from about 50 mg to about 70 mg of the adsorbent. In some embodiments, a pharmaceutical composition is provided that comprises from about 50 mg to about 65 mg of the adsorbent. In some embodiments, a pharmaceutical composition is provided that comprises from about 50 mg to about 60 mg of the adsorbent. In some embodiments, a pharmaceutical composition is provided that comprises from about 50 mg to about 55 mg of the adsorbent. In some embodiments, the adsorbent comprises about 5% of the total weight of the composition. In some embodiments, the adsorbent comprises about 10% of the total weight of the composition. In some embodiments, the adsorbent comprises about 15% of the total weight of the composition. In some embodiments, the adsorbent comprises about 20% of the total weight of the composition. In some embodiments, the adsorbent comprises about 25% of the total weight of the composition. In some embodiments, the adsorbent comprises about 30% of the total weight of the composition. In some embodiments, the adsorbent comprises about 40% of the total weight of the composition. In some embodiments, the adsorbent comprises about 50% of the total weight of the composition. In some embodiments, the adsorbent is present in the amorphous solid dispersion. In some embodiments, the silicon dioxide comprises about 5% of the total weight of the composition. In some embodiments, the silicon dioxide comprises about 10% of the total weight of the composition. In some embodiments, the silicon dioxide comprises about 15% of the total weight of the composition. In some embodiments, the silicon dioxide comprises about 20% of the total weight of the composition. In some embodiments, the silicon dioxide comprises about 25% of the total weight of the composition. In some embodiments, the silicon dioxide comprises about 30% of the total weight of the composition. In some embodiments, the silicon dioxide comprises about 40% of the total weight of the composition. In some embodiments, the silicon dioxide comprises about 50% of the total weight of the composition. In some embodiments, the silicon dioxide is present in the amorphous solid dispersion.

In some embodiments, a pharmaceutical composition is provided that comprises from about 0.10% to about 99% by weight of an adsorbent, such as silicon dioxide. In some embodiments, a pharmaceutical composition is provided that comprises from about 0.1% to about 80% by weight of the adsorbent. In some embodiments, a pharmaceutical composition is provided that comprises from about 0.10% to about 60% by weight of the adsorbent. In some embodiments, a pharmaceutical composition is provided that comprises from about 0.1% to about 40% by weight of the adsorbent. In some embodiments, a pharmaceutical composition is provided that comprises from about 0.1% to about 20% by weight of the adsorbent. In some embodiments, a pharmaceutical composition is provided that comprises from about 0.1% to about 10% by weight of the adsorbent. In some embodiments, a pharmaceutical composition is provided that comprises from about 0.10% to about T % by weight of the adsorbent. In some embodiments, a pharmaceutical composition is provided that comprises from about 20% to about 99% by weight of the adsorbent. In some embodiments, a pharmaceutical composition is provided that comprises from about 20% to about 80% by weight of the adsorbent. In some embodiments, a pharmaceutical composition is provided that comprises from about 20% to about 60% by weight of the adsorbent. In some embodiments, a pharmaceutical composition is provided that comprises from about 20% to about 40% by weight of the adsorbent. In some embodiments, a pharmaceutical composition is provided that comprises from about 30% to about 99% by weight of the adsorbent. In some embodiments, a pharmaceutical composition is provided that comprises from about 30% to about 80% by weight of the adsorbent. In some embodiments, a pharmaceutical composition is provided that comprises from about 30% to about 60% by weight of the adsorbent. In some embodiments, a pharmaceutical composition is provided that comprises from about 30% to about 40% by weight of the adsorbent. In some embodiments, a pharmaceutical composition is provided that comprises from about 40% to about 99% by weight of the adsorbent. In some embodiments, a pharmaceutical composition is provided that comprises from about 40% to about 80% by weight of the adsorbent. In some embodiments, a pharmaceutical composition is provided that comprises from about 40% to about 60% by weight of the adsorbent. In some embodiments, a pharmaceutical composition is provided that comprises from about 15% to about 45% by weight of the adsorbent. In some embodiments, a pharmaceutical composition is provided that comprises from about 25% to about 40% by weight of the adsorbent. In some embodiments, a pharmaceutical composition is provided that comprises from about 20% to about 35% by weight of the adsorbent. In some embodiments, a pharmaceutical composition is provided that comprises from about 25% to about 40% by weight of the adsorbent. In some embodiments, a pharmaceutical composition is provided that comprises from about 15% to about 35% by weight of the adsorbent. In some embodiments, a pharmaceutical composition is provided that comprises from about 15 to about 50% by weight of the adsorbent. In some embodiments, the adsorbent is present in the amorphous solid dispersion.

In some embodiments, an adsorbent is present in a pharmaceutical composition. In some embodiments, an adsorbent powder described herein has an average diameter of 1-1000 nm. In some embodiments, the particle size of the adsorbent is from about 0.01 to 1000 nanometers. In some embodiments, the particle size of the adsorbent is from about 0.01 nanometers to about 1,000 nanometers. In some embodiments, the particle size of the adsorbent is from at least about 0.01 nanometers. In some embodiments, the particle size of the adsorbent is from at most about 1,000 nanometers. In some embodiments, the particle size of the adsorbent is from about 1 nanometer to about 500 nanometers. In some embodiments, the particle size of the adsorbent is from at least about 1 nanometer. In some embodiments, the particle size of the adsorbent is from at most about 500 nanometers. In some embodiments, the particle size of the adsorbent is from about 1 nanometer to about 300 nanometers, about 1 nanometer to about 700 nanometers, about 1 nanometer to about 100 nanometers, about 1 nanometer to about 130 nanometers, about 1 nanometer to about 170 nanometers, about 1 nanometer to about 200 nanometers, about 1 nanometer to about 230 nanometers, about 1 nanometer to about 270 nanometers, about 1 nanometer to about 30 nanometers, about 1 nanometer to about 400 nanometers, about 1 nanometer to about 500 nanometers, about 10 nanometers to about 130 nanometers, about 10 nanometers to about 170 nanometers, about 100 nanometers to about 200 nanometers, about 100 nanometers to about 230 nanometers, about 100 nanometers to about 270 nanometers, about 100 nanometers to about 300 nanometers, about 100 nanometers to about 400 nanometers, about 200 nanometers to about 270 nanometers, about 200 nanometers to about 300 nanometers, about 200 nanometers to about 400 nanometers, about 200 nanometers to about 500 nanometers, about 300 nanometers to about 400 nanometers, or about 400 nanometers to about 500 nanometers. In some embodiments, the particle size of the adsorbent is from about 1 nanometer to about 100 nanometers. In some embodiments, the particle size of the adsorbent is from at least about 1 nanometer. In some embodiments, the particle size of the adsorbent is about 0.1, 1, 30, 50, 70, 100, 130, 170, 200, 230, 250, 270, 300, 330, 350, 370, 400, 430, 450, 470, 500, 600, 700, 800, 900, or 1000 nanometers or less. In some embodiments, the adsorbent is silicon dioxide powder with an average diameter of 1-1000 nm. In some embodiments, the particle size of the silicon dioxide is from about 0.01 to 1000 nanometers. In some embodiments, the particle size of the silicon dioxide is from about 0.01 nanometers to about 1,000 nanometers. In some embodiments, the particle size of the silicon dioxide is from at least about 0.01 nanometers. In some embodiments, the particle size of the silicon dioxide is from at most about 1,000 nanometers. In some embodiments, the particle size of the silicon dioxide is from about 1 nanometer to about 500 nanometers. In some embodiments, the particle size of the silicon dioxide is from at least about 1 nanometer. In some embodiments, the particle size of the silicon dioxide is from at most about 500 nanometers. In some embodiments, the particle size of the silicon dioxide is from about 1 nanometer to about 300 nanometers, about 1 nanometer to about 700 nanometers, about 1 nanometer to about 100 nanometers, about 1 nanometer to about 130 nanometers, about 1 nanometer to about 170 nanometers, about 1 nanometer to about 200 nanometers, about 1 nanometer to about 230 nanometers, about 1 nanometer to about 270 nanometers, about 1 nanometer to about 30 nanometers, about 1 nanometer to about 400 nanometers, about 1 nanometer to about 500 nanometers, about 10 nanometers to about 130 nanometers, about 10 nanometers to about 170 nanometers, about 100 nanometers to about 200 nanometers, about 100 nanometers to about 230 nanometers, about 100 nanometers to about 270 nanometers, about 100 nanometers to about 300 nanometers, about 100 nanometers to about 400 nanometers, about 100 nanometers to about 500 nanometers, about 200 nanometers to about 270 nanometers, about 200 nanometers to about 300 nanometers, about 200 nanometers to about 400 nanometers, about 200 nanometers to about 500 nanometers, about 300 nanometers to about 400 nanometers, about 300 nanometers to about 500 nanometers, or about 400 nanometers to about 500 nanometers. In some embodiments, the particle size of the silicon dioxide is from about 1 nanometer to about 100 nanometers. In some embodiments, the particle size of the silicon dioxide is from at least about 1 nanometer. In some embodiments, the particle size of the silicon dioxide is about 0.1, 1, 30, 50, 70, 100, 130, 170, 200, 230, 250, 270, 300, 330, 350, 370, 400, 430, 450, 470, 500, 600, 700, 800, 900, or 1000 nanometers or less.

In some embodiments, the silicon dioxide is present in the amorphous solid dispersion. In some embodiments, the amorphous solid dispersion is granulated and incorporated into a pharmaceutical composition with extra granular additives. In some embodiments, the silicon dioxide is present outside of the amorphous solid dispersion as an extra-granular additive. In some embodiments, silicon dioxide is present in the amorphous solid dispersion as well as being an extra-granular additive.

Other Additives

In some embodiments, pharmaceutical compositions described herein comprise a lipophilic API, a hydrophilic polymer, a surfactant, optionally an adsorbent, and optionally an additional additive or additives. In some embodiments, the API is an API of Table 1 or a pharmaceutically acceptable salt thereof. In some embodiments, a pharmaceutically acceptable organic or inorganic acid or acid is included as an internal additive and thus as part of a solid dispersion. In some embodiments, a pharmaceutically acceptable organic or inorganic acid or acids are included as an external additive that is not part of the solid dispersion. The pharmaceutically acceptable organic acid is selected from the group consisting of tartaric acid, fumaric acid, succinic acid, citric acid, lactic acid, malic acid, aliphatic sulfonic acids (e.g., methanesulfonic acid, ethanesulfonic acid, isethionic acid, etc.) and aromatic sulfonic acids (e.g., benzenesulfonic acid, p-toluenesulfonic acid, etc.), and the pharmaceutically acceptable inorganic acid is selected from the group consisting of hydrochloric acid, sulfuric acid, phosphoric acid and the like.

In some embodiments, the organic acid or inorganic acid is present in a pharmaceutical composition described herein in an amount of at least 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, or 200 mg. In some embodiments, the organic acid or inorganic acid is present in an amount of about 10 mg, 20 mg, 25 mg, 30 mg, 40 mg, 50 mg, 60 mg, 70 mg, 75 mg, 80 mg, 90 mg, 100 mg, 110 mg, 120 mg, 125 mg, 130 mg, 140 mg, 150 mg, 160 mg, 170 mg, 175 mg, 180 mg, 190 mg, 200 mg, 225 mg, or 250 mg. In some embodiments, the organic acid or inorganic acid is present in an amount of no more than 1000 mg, 750 mg, 500 mg, 400 mg, 300 mg, 250 mg, 225 mg, 200 mg, 175 mg, 150 mg, 125 mg, 100 mg, 90 mg, 80 mg, 75 mg, 60 mg, 55 mg, 50 mg, or 25 mg. In some embodiments, the organic acid or inorganic acid is present in the amorphous solid dispersion.

In some embodiments, organic acid or inorganic acid is present in a pharmaceutical composition described herein in an amount from about 1.0 mg to about 1000 mg, including but not limited to about 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0 mg, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg. In some embodiments, the organic acid or inorganic acid is present in the amorphous solid dispersion.

In some embodiments, a pharmaceutical composition is provided that comprises from about 1 mg to about 500 mg of the organic acid or inorganic acid. In some embodiments, a pharmaceutical composition is provided that comprises from about 10 mg to about 400 mg of the organic acid or inorganic acid. In some embodiments, a pharmaceutical composition is provided that comprises from about 25 mg to about 200 mg of the organic acid or inorganic acid. In some embodiments, a pharmaceutical composition is provided that comprises from about 50 mg to about 150 mg of the organic acid or inorganic acid. In some embodiments, a pharmaceutical composition is provided that comprises from about 75 mg to about 125 mg of the organic acid or inorganic acid. In some embodiments, a pharmaceutical composition is provided that comprises from about 75 mg to about 100 mg of the organic acid or inorganic acid. In some embodiments, a pharmaceutical composition is provided that comprises from about 100 mg to about 125 mg of the organic acid or inorganic acid. In some embodiments, a pharmaceutical composition is provided that comprises from about 1 mg to about 200 mg of the organic acid or inorganic acid. In some embodiments, a pharmaceutical composition is provided that comprises from about 25 mg to about 200 mg of the organic acid or inorganic acid. In some embodiments, a pharmaceutical composition is provided that comprises from about 50 mg to about 200 mg of the organic acid or inorganic acid. In some embodiments, a pharmaceutical composition is provided that comprises from about 50 mg to about 150 mg of the organic acid or inorganic acid. In some embodiments, a pharmaceutical composition is provided that comprises from about 75 mg to about 125 mg of the organic acid or inorganic acid. In some embodiments, a pharmaceutical composition is provided that comprises from about 75 mg to about 100 mg of the organic acid or inorganic acid. In some embodiments, a pharmaceutical composition is provided that comprises from about 100 mg to about 125 mg of the organic acid or inorganic acid. In some embodiments, a pharmaceutical composition is provided that comprises from about 50 mg to about 150 mg of the organic acid or inorganic acid. In some embodiments, a pharmaceutical composition is provided that comprises from about 55 mg to about 150 mg of the organic acid or inorganic acid. In some embodiments, a pharmaceutical composition is provided that comprises from about 60 mg to about 150 mg of the organic acid or inorganic acid. In some embodiments, a pharmaceutical composition is provided that comprises from about 65 mg to about 150 mg of the organic acid or inorganic acid. In some embodiments, a pharmaceutical composition is provided that comprises from about 70 mg to about 150 mg of the organic acid or inorganic acid. In some embodiments, a pharmaceutical composition is provided that comprises from about 75 mg to about 150 mg of the organic acid or inorganic acid. In some embodiments, a pharmaceutical composition is provided that comprises from about 80 mg to about 150 mg of the organic acid or inorganic acid. In some embodiments, a pharmaceutical composition is provided that comprises from about 85 mg to about 150 mg of the organic acid or inorganic acid. In some embodiments, a pharmaceutical composition is provided that comprises from about 90 mg to about 150 mg of the organic acid or inorganic acid. In some embodiments, a pharmaceutical composition is provided that comprises from about 95 mg to about 150 mg of the organic acid or inorganic acid. In some embodiments, a pharmaceutical composition is provided that comprises from about 100 mg to about 150 mg of the organic acid or inorganic acid. In some embodiments, a pharmaceutical composition is provided that comprises from about 105 mg to about 150 mg of the organic acid or inorganic acid. In some embodiments, a pharmaceutical composition is provided that comprises from about 110 mg to about 150 mg of the organic acid or inorganic acid. In some embodiments, a pharmaceutical composition is provided that comprises from about 115 mg to about 150 mg of the organic acid or inorganic acid. In some embodiments, a pharmaceutical composition is provided that comprises from about 120 mg to about 150 mg of the organic acid or inorganic acid. In some embodiments, a pharmaceutical composition is provided that comprises from about 125 mg to about 150 mg of the organic acid or inorganic acid. In some embodiments, a pharmaceutical composition is provided that comprises from about 130 mg to about 150 mg of the organic acid or inorganic acid. In some embodiments, a pharmaceutical composition is provided that comprises from about 135 mg to about 150 mg of the organic acid or inorganic acid. In some embodiments, a pharmaceutical composition is provided that comprises from about 140 mg to about 150 mg of the organic acid or inorganic acid. In some embodiments, a pharmaceutical composition is provided that comprises from about 145 mg to about 150 mg of the organic acid or inorganic acid. In some embodiments, a pharmaceutical composition is provided that comprises from about 50 mg to about 145 mg of the organic acid or inorganic acid. In some embodiments, a pharmaceutical composition is provided that comprises from about 50 mg to about 140 mg of the organic acid or inorganic acid. In some embodiments, a pharmaceutical composition is provided that comprises from about 50 mg to about 135 mg of the organic acid or inorganic acid. In some embodiments, a pharmaceutical composition is provided that comprises from about 50 mg to about 130 mg of the organic acid or inorganic acid. In some embodiments, a pharmaceutical composition is provided that comprises from about 50 mg to about 125 mg of the organic acid or inorganic acid. In some embodiments, a pharmaceutical composition is provided that comprises from about 50 mg to about 120 mg of the organic acid or inorganic acid. In some embodiments, a pharmaceutical composition is provided that comprises from about 50 mg to about 115 mg of the organic acid or inorganic acid. In some embodiments, a pharmaceutical composition is provided that comprises from about 50 mg to about 110 mg of the organic acid or inorganic acid. In some embodiments, a pharmaceutical composition is provided that comprises from about 50 mg to about 105 mg of the organic acid or inorganic acid. In some embodiments, a pharmaceutical composition is provided that comprises from about 50 mg to about 100 mg of the organic acid or inorganic acid. In some embodiments, a pharmaceutical composition is provided that comprises from about 50 mg to about 95 mg of the organic acid or inorganic acid. In some embodiments, a pharmaceutical composition is provided that comprises from about 50 mg to about 90 mg of the organic acid or inorganic acid. In some embodiments, a pharmaceutical composition is provided that comprises from about 50 mg to about 85 mg of the organic acid or inorganic acid. In some embodiments, a pharmaceutical composition is provided that comprises from about 50 mg to about 80 mg of the organic acid or inorganic acid. In some embodiments, a pharmaceutical composition is provided that comprises from about 50 mg to about 75 mg of the organic acid or inorganic acid. In some embodiments, a pharmaceutical composition is provided that comprises from about 50 mg to about 70 mg of the organic acid or inorganic acid. In some embodiments, a pharmaceutical composition is provided that comprises from about 50 mg to about 65 mg of the organic acid or inorganic acid. In some embodiments, a pharmaceutical composition is provided that comprises from about 50 mg to about 60 mg of the organic acid or inorganic acid. In some embodiments, a pharmaceutical composition is provided that comprises from about 50 mg to about 55 mg of the organic acid or inorganic acid. In some embodiments, the organic acid or inorganic acid comprises about 5% of the total weight of the composition. In some embodiments, the organic acid or inorganic acid comprises about 10% of the total weight of the composition. In some embodiments, the organic acid or inorganic acid comprises about 15% of the total weight of the composition. In some embodiments, the organic acid or inorganic acid comprises about 20% of the total weight of the composition. In some embodiments, the organic acid or inorganic acid comprises about 25% of the total weight of the composition. In some embodiments, the organic acid or inorganic acid comprises about 30% of the total weight of the composition. In some embodiments, the organic acid or inorganic acid comprises about 40% of the total weight of the composition. In some embodiments, the organic acid or inorganic acid comprises about 50% of the total weight of the composition. In some embodiments, the organic acid or inorganic acid is present in the amorphous solid dispersion.

In some embodiments, a pharmaceutical composition is provided that comprises from about 0.10% to about 99% by weight of the organic acid or inorganic acid. In some embodiments, a pharmaceutical composition is provided that comprises from about 0.1% to about 80% by weight of the organic acid or inorganic acid. In some embodiments, a pharmaceutical composition is provided that comprises from about 0.1% to about 60% by weight of the organic acid or inorganic acid. In some embodiments, a pharmaceutical composition is provided that comprises from about 0.1% to about 40% by weight of the organic acid or inorganic acid. In some embodiments, a pharmaceutical composition is provided that comprises from about 0.1% to about 20% by weight of the organic acid or inorganic acid. In some embodiments, a pharmaceutical composition is provided that comprises from about 0.1% to about 10% by weight of the organic acid or inorganic acid. In some embodiments, a pharmaceutical composition is provided that comprises from about 0.1% to about 1% by weight of the organic acid or inorganic acid. In some embodiments, a pharmaceutical composition is provided that comprises from about 20% to about 99% by weight of the organic acid or inorganic acid. In some embodiments, a pharmaceutical composition is provided that comprises from about 20% to about 80% by weight of the organic acid or inorganic acid. In some embodiments, a pharmaceutical composition is provided that comprises from about 20% to about 60% by weight of the organic acid or inorganic acid. In some embodiments, a pharmaceutical composition is provided that comprises from about 20% to about 40% by weight of the organic acid or inorganic acid. In some embodiments, a pharmaceutical composition is provided that comprises from about 30% to about 99% by weight of the organic acid or inorganic acid. In some embodiments, a pharmaceutical composition is provided that comprises from about 30% to about 80% by weight of the organic acid or inorganic acid. In some embodiments, a pharmaceutical composition is provided that comprises from about 30% to about 60% by weight of the organic acid or inorganic acid. In some embodiments, a pharmaceutical composition is provided that comprises from about 30% to about 40% by weight of the organic acid or inorganic acid. In some embodiments, a pharmaceutical composition is provided that comprises from about 40% to about 99% by weight of the organic acid or inorganic acid. In some embodiments, a pharmaceutical composition is provided that comprises from about 40% to about 80% by weight of the organic acid or inorganic acid. In some embodiments, a pharmaceutical composition is provided that comprises from about 40% to about 60% by weight of the organic acid or inorganic acid.

An amorphous solid dispersion composition or a pharmaceutical composition described herein can comprise one or more preservatives. Preservatives can include anti-microbials, antioxidants, and agents that enhance sterility. Exemplary preservatives include ascorbic acid, ascorbyl palmitate, butylatedhydroxyanisole (BHA), Butylatedhydroxytoulene (BHT), propyl gallate, citric acid, EDTA and its salts, erythorbic acid, fumaric acid, malic acid, propyl gallate, sodium ascorbate, sodium bisulfate, sodium metabisulfite, sodium sulfite, parabens (such as methylparaben, ethylparaben, propylparaben, butylparaben and their salts), benzoic acid, sodium benzoate, potassium sorbate, vanillin, and the like. In some embodiments, an amorphous solid dispersion composition or a pharmaceutical composition described herein comprises an antioxidant. In some embodiments, the antioxidant comprises a-tocopherol acetate, acetone sodium bisulfite, acetylcysteine, ascorbic acid, vitamin E, ascorbyl palmitate, BHA, BHT, cysteine, cysteine hydrochloride, d-a-tocopherol (natural or synthetic), dithiothreitol, monothioglycerol, nordihydroguaiaretic acid, propyl gallate, sodium bisulfite, sodium formaldehyde sulfoxylate, sodium metabisulfite, sodium sulfite, sodium thiosulfate, thiourea, or tocopherols.

In some embodiments, pharmaceutical compositions described herein comprise a lipophilic API, a hydrophilic polymer, a surfactant, optionally an adsorbent, and optionally an additional additive or additives. In some embodiments, an antioxidant or mixture of antioxidants are included as the internal additive thus as part of a solid dispersion. In some embodiments, an antioxidant or mixture of antioxidants are included as an external additive. The exemplary antioxidants include but are not limited to BHT, BHA, gallic acid, propyl gallate, ascorbic acid, ascorbyl palmitate, 4hydroxymethyl-2,6-di-tert-butyl phenol, and tocopherol.

In some embodiments, the antioxidant is present in a pharmaceutical composition described herein in an amount of at least 1 mg, 2 mg, 2.5 mg, 3 mg, 4 mg, 5 mg, 6 mg, 7 mg, 7.5 mg, 8 mg, 9 mg, 10 mg, 11 mg, 12 mg, 12.5 mg, 13 mg, 14 mg, 1.5 mg, 16 mg, 17 mg, 17.5 mg, 18 mg, 19 mg, or 20 mg. In some embodiments, the antioxidant is present in an amount of about 1 mg, 2 mg, 2.5 mg, 3 mg, 4 mg, 5 mg, 6 mg, 7 mg, 7.5 mg, 8 mg, 9 mg, 10 mg, 11 mg, 12 mg, 12.5 mg, 13 mg, 14 mg, 1.5 mg, 16 mg, 17 mg, 17.5 mg, 18 mg, 19 mg, 20 mg, 22.5 mg, or 2.5 mg. In some embodiments, the antioxidant is present in an amount of no more than 100 mg, 7.5 mg, 50 mg, 40 mg, 30 mg, 2.5 mg, 22.5 mg, 20 mg, 17.5 mg, 1.5 mg, 12.5 mg, 10 mg, 9 mg, 8 mg, 7.5 mg, 6 mg, 5.5 mg, 5 mg, or 2.5 mg. In some embodiments, the antioxidant is present in the amorphous solid dispersion.

In some embodiments, the antioxidant is present in a pharmaceutical composition described herein in an amount from about 1.0 mg to about 100 mg, including but not limited to about 1.0 mg, 1.5 mg, 2.5 mg, 3.0 mg, 4.0 mg, 5.0 mg, 6.0 mg, 6.5 mg, 7.0 mg, 7.5 mg, 8.0 mg, 8.5 mg, 9.0 mg, 9.5 mg, 10.0, 10.5 mg, 11.0 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, or 100 mg. In some embodiments, the antioxidant is present in the amorphous solid dispersion.

In some embodiments, a pharmaceutical composition is provided that comprises from about 0.01 mg to about 100 mg of an antioxidant. In some embodiments, the amount of antioxidant is from about 0.01 mg to about 100 mg. In some embodiments, the amount of antioxidant is from about 0.01 mg to about 0.1 mg, about 0.01 mg to about 1 mg, about 0.01 mg to about 3 mg, about 0.01 mg to about 5 mg, about 0.01 mg to about 7 mg, about 0.01 mg to about 10 mg, about 0.01 mg to about 15 mg, about 0.01 mg to about 20 mg, about 0.01 mg to about 25 mg, about 0.01 mg to about 50 mg, about 0.01 mg to about 100 mg, about 0.1 mg to about 1 mg, about 0.1 mg to about 3 mg, about 0.1 mg to about 5 mg, about 0.1 mg to about 7 mg, about 0.1 mg to about 10 mg, about 0.1 mg to about 15 mg, about 0.1 mg to about 20 mg, about 0.1 mg to about 25 mg, about 0.1 mg to about 50 mg, about 0.1 mg to about 100 mg, about 1 mg to about 3 mg, about 1 mg to about 5 mg, about 1 mg to about 7 mg, about 1 mg to about 10 mg, about 1 mg to about 15 mg, about 1 mg to about 20 mg, about 1 mg to about 25 mg, about 1 mg to about 50 mg, about 1 mg to about 100 mg, about 3 mg to about 5 mg, about 3 mg to about 7 mg, about 3 mg to about 10 mg, about 3 mg to about 15 mg, about 3 mg to about 20 mg, about 3 mg to about 25 mg, about 3 mg to about 50 mg, about 3 mg to about 100 mg, about 5 mg to about 7 mg, about 5 mg to about 10 mg, about 5 mg to about 15 mg, about 5 mg to about 20 mg, about 5 mg to about 25 mg, about 5 mg to about 50 mg, about 5 mg to about 100 mg, about 7 mg to about 10 mg, about 7 mg to about 15 mg, about 7 mg to about 20 mg, about 7 mg to about 25 mg, about 7 mg to about 50 mg, about 7 mg to about 100 mg, about 10 mg to about 15 mg, about 10 mg to about 20 mg, about 10 mg to about 25 mg, about 10 mg to about 50 mg, about 10 mg to about 100 mg, about 15 mg to about 20 mg, about 15 mg to about 25 mg, about 15 mg to about 50 mg, about 15 mg to about 100 mg, about 20 mg to about 25 mg, about 20 mg to about 50 mg, about 20 mg to about 100 mg, about 25 mg to about 50 mg, about 25 mg to about 100 mg, or about 50 mg to about 100 mg. In some embodiments, the amount of antioxidant is from about 0.01 mg, about 0.1 mg, about 1 mg, about 3 mg, about 5 mg, about 7 mg, about 10 mg, about 15 mg, about 20 mg, about 25 mg, about 50 mg, or about 100 mg. In some embodiments, the amount of antioxidant is from at least about 0.01 mg, about 0.1 mg, about 1 mg, about 3 mg, about 5 mg, about 7 mg, about 10 mg, about 15 mg, about 20 mg, about 25 mg, or about 50 mg. In some embodiments, the amount of antioxidant is from at most about 0.1 mg, about 1 mg, about 3 mg, about 5 mg, about 7 mg, about 10 mg, about 15 mg, about 20 mg, about 25 mg, about 50 mg, or about 100 mg. In some embodiments, the antioxidant comprises about 0.001% of the total weight of the composition. In some embodiments, the antioxidant comprises about 0.01% of the total weight of the composition. In some embodiments, the antioxidant comprises about 0.10% of the total weight of the composition. In some embodiments, the antioxidant comprises about 1% of the total weight of the composition. In some embodiments, the antioxidant comprises about 2% of the total weight of the composition. In some embodiments, the antioxidant comprises about 3% of the total weight of the composition. In some embodiments, the antioxidant comprises about 4% of the total weight of the composition. In some embodiments, the antioxidant comprises about 5% of the total weight of the composition. In some embodiments, the antioxidant comprises about 6% of the total weight of the composition. In some embodiments, the antioxidant comprises about 7% of the total weight of the composition. In some embodiments, the antioxidant comprises about 8% of the total weight of the composition. In some embodiments, the antioxidant comprises about 9% of the total weight of the composition. In some embodiments, the antioxidant comprises about 10% of the total weight of the composition. In some embodiments, the antioxidant is present in the amorphous solid dispersion.

In some embodiments, a pharmaceutical composition is provided that comprises from about 0.001% to about 10% by weight of antioxidant. In some embodiments, the percent weight of antioxidant is from about 0.001% to about 0.01%, about 0.001% to about 0.1%, about 0.001% to about 1%, about 0.001% to about 2%, about 0.001% to about 3%, about 0.001% to about 4%, about 0.001% to about 5%, about 0.001% to about 6%, about 0.001% to about 7%, about 0.001% to about 8%, about 0.001% to about 10%, about 0.01% to about 0.1%, about 0.01% to about 1%, about 0.01% to about 2%, about 0.01% to about 3%, about 0.01% to about 4%, about 0.01% to about 5%, about 0.01% to about 6%, about 0.01% to about 7%, about 0.01% to about 8%, about 0.01% to about 10%, about 0.1% to about 1%, about 0.1% to about 2%, about 0.1% to about 3%, about 0.1% to about 4%, about 0.1% to about 5%, about 0.1% to about 6%, about 0.1% to about 7%, about 0.1% to about 8%, about 0.1% to about 10%, about 1% to about 2%, about 1% to about 3%, about 1% to about 4%, about 1% to about 5%, about 1% to about 6%, about 1% to about 7%, about 1% to about 8%, about 1% to about 10%, about 2% to about 3%, about 2% to about 4%, about 2% to about 5%, about 2% to about 6%, about 2% to about 7%, about 2% to about 8%, about 2% to about 10%, about 3% to about 4%, about 3% to about 5%, about 3% to about 6%, about 3% to about 7%, about 3% to about 8%, about 3% to about 10%, about 4% to about 5%, about 4% to about 6% about 4% to about 7%, about 4% to about 8%, about 4% to about 10%, about 5% to about 6%, about 5% to about 7%, about 5% to about 8%, about 5% to about 10%, about 6% to about 7%, about 6% to about 8%, about 6% to about 10%, about 7% to about 8% about 7% to about 10%, or about 8% to about 10%. In some embodiments, the percent weight of antioxidant is from about 0.001%, about 0.01% about 0.1%, about 1%, about 2%, about 3%, about 4%, about 5%, about 6%, about 7%, about 8%, or about 10%. In some embodiments, the percent weight of antioxidant is from at least about 0.001%, about 0.01%, about 0.1%, about 1%, about 2%, about 3%, about 4%, about 5%, about 6%, about 7%, or about 8%. In some embodiments, the percent weight of antioxidant is from at most about 0.01%, about 0.1%, about 1%, about 2%, about 3%, about 4%, about 5% about 6%, about 7%, about 8%, or about 10%.

The above different internal additives can be used alone or together.

In some embodiments, a pharmaceutical composition described herein comprises a glidants. In some embodiments, the glidant is silicon dioxide powder. In some embodiments, the silicon dioxide is present in the amorphous solid dispersion. In some embodiments, silicon dioxide is not present in the amorphous solid dispersion, but is included in the pharmaceutical formulation. In some embodiments, the silicon dioxide is present in the amorphous solid dispersion as well as being a component of the pharmaceutical composition outside of the amorphous solid dispersion.

In some embodiments, pharmaceutical compositions described herein comprise a lipophilic API, a hydrophilic polymer, a surfactant, optionally an adsorbent, optionally an internal additive, and optionally and external additive. In some embodiments, the lipophilic API has a calculated log P or log P of at least 2.0. In some embodiments the API is nilotinib or a pharmaceutically acceptable salt thereof. In some embodiments, the API is nilotinib. In some embodiments, the API is a pharmaceutically acceptable salt of nilotinib. In some embodiments, the API is a lipophilic API. In some embodiments, the lipophilic API is one listed in Table 1, or a pharmaceutically acceptable salt thereof. In some embodiments, other external additives conventionally mixed with pharmaceutical compositions can be included, and these additives are well known in the art. Such additives include, but are not limited to, anti-adherents (anti-sticking agents, glidants, flow promoters, lubricants) (e.g., talc, magnesium stearate, fumed silica (CarboSil®, AEROSIL®), micronized silica (SYLOID® No. FP 244, Grace U.S.A.), polyethylene glycols, surfactants, waxes, stearic acid, stearic acid salts, stearic acid derivatives, starch, hydrogenated vegetable oils, sodium benzoate, sodium acetate, silicone dioxide, leucine, PEG-4000 and magnesium lauryl sulfate) anticoagulants (e.g., acetylated monoglycerides), antifoaming agents (e.g., long-chain alcohols and silicone derivatives), antioxidants (e.g., BHT, BHA, gallic acid, propyl gallate, ascorbic acid, ascorbyl palmitate, 4hydroxymethyl-2,6-di-tert-butyl phenol, tocopherol, etc.), binders (adhesives), i.e., agents that impart cohesive properties to powdered materials through particle-particle bonding, (e.g., matrix binders (dry starch, dry sugars), film binders (, starch paste, celluloses, bentonite, sucrose)), chemical binders (e.g., polymeric cellulose derivatives, such as carboxy methyl cellulose, etc., sugar syrups, corn syrup, water soluble polysaccharides (e.g., acacia, tragacanth, guar, alginates, etc), gelatin, gelatin hydrolysate, agar, sucrose, dextrose, non-cellulosic binders (e.g., PEG, pregelatinized starch, sorbitol, glucose, etc.), bufferants, where the acid is a pharmaceutically acceptable acid, (e.g., hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, etc) and where the base is a pharmaceutically acceptable base, (e.g., an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a pharmaceutically acceptable salt of acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, parabromophenylsulfonic acid, propionic acid, p-toluenesulfonic acid, salicylic acid, stearic acid, succinic acid, tannic acid, tartaric acid, thioglycolic acid, toluenesulfonic acid, and uric acid, chelating agents (e.g., EDTA and EDTA salts), coagulants (e.g., alginates) colorants or opaquants, (e.g., titanium dioxide, food dyes, lakes, natural vegetable colorants, iron oxides, silicates, sulfates, magnesium hydroxide and aluminum hydroxide), coolants, (e.g. halogenated hydrocarbons (e.g., trichloroethane, trichloroethylene, dichloromethane, fluorotrichloromethane), diethylether and liquid nitrogen) cryoprotectants (e.g., trehelose, phosphates, citric acid, tartaric acid, gelatin, dextran, mannitol, etc.), diluents or fillers, (e.g., lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose disintegrants or super disintegrants (e.g., croscarmellose sodium, starch, starch derivatives, clays, gums, cellulose, cellulose derivatives, alginates, sodium starch glycolate and microcrystalline cellulose), hydrogen bonding agents, (e.g., magnesium oxide), flavorants or desensitizers, (e.g., spray-dried flavors, essential oils and ethyl vanillin), ion-exchange resins (e.g., styrene/divinyl benzene copolymers, and quaternary ammonium compounds), plasticizers (e.g., polyethylene glycol, citrate esters (e.g., triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl seccate), preservatives (e.g., ascorbic acid, boric acid, sorbic acid, benzoic acid, and salts thereof, parabens, phenols, benzyl alcohol, and quaternary ammonium compounds), solvents (e.g., alcohols, ketones, esters, chlorinated hydrocarbons and water) sweeteners, including natural sweeteners (e.g., maltose, sucrose, glucose, sorbitol, glycerin and dextrins), and artificial sweeteners (e.g., aspartame, saccharine and saccharine salts) and thickeners (viscosity modifiers, thickening agents), (e.g., sugars, cellulosics, polymers and alginates).

Additives can also be materials such as proteins (e.g., collagen, gelatin, Zein, gluten, mussel protein, lipoprotein), carbohydrates (e.g., alginates, carrageenan, cellulose derivatives, pectin, starch, chitosan), gums (e.g., xanthan gum, gum arabic), spermaceti, natural or synthetic waxes, carnauba wax, fatty acids (e.g., stearic acid, hydroxystearic acid), fatty alcohols, sugars, shellacs, such as those based on sugars (e.g., lactose, sucrose, dextrose) or starches, polysaccharide-based polymers (e.g., maltodextrin and maltodextrin derivatives, dextrates, cyclodextrin and cyclodextrin derivatives), cellulosic-based polymers (e.g., microcrystalline cellulose, sodium carboxymethyl cellulose, hydroxypropylmethyl cellulose, ethyl cellulose, hydroxypropyl cellulose, cellulose acetate, cellulose nitrate, cellulose acetate butyrate, cellulose acetate, trimellitate, carboxymethylethyl cellulose, hydroxypropylmethyl cellulose phthalate), inorganics, (e.g., dicalcium phosphate, hydroxyapitite, tricalcium phosphate, talc and titania), polyols (e.g., mannitol, xylitol and sorbitol polyethylene glycol esters) and polymers (e.g., alginates, poly(lactide coglycolide), gelatin, crosslinked gelatin and agar-agar).

Surface Modified Acid

In some embodiments, pharmaceutical compositions described herein comprise a lipophilic API, a hydrophilic polymer, a surfactant, optionally an adsorbent, optionally an internal additive, and optionally and external additive. In some embodiments, the lipophilic API, a hydrophilic polymer, a surfactant, optionally an adsorbent, and optionally an internal additive make up an amorphous solid dispersion. In some embodiments, the API is an API of Table 1 or a pharmaceutically acceptable salt thereof. An external additive differs from an internal additive in that the external additive is not incorporated into the amorphous solid dispersion. In some embodiments, the external additive is an external acid that is not included in the amorphous solid dispersion. In some embodiments, the external acid is an organic acid or amino acid. In some embodiments, the organic acid is tartaric acid, fumaric acid, succinic acid, citric acid, lactic acid, malic acid, maleic acid, benzenesulfonic acid, or p-toluenesulfonic acid. In some embodiments, the amino acid is glutamic acid, aspartic acid, or acidic salts of glycine, alanine or serine. In some embodiments, the external acid is a surface modified acid. In some embodiments, a surface modified acid comprises a powdered or granulated acid with a neutral salt layer at least partially coating the exterior of the powdered or granulated acid. In some embodiments, the surface modified acid comprises a powdered or granulated acid selected from tartaric acid, fumaric acid, succinic acid, citric acid, lactic acid, malic acid, maleic acid, benzenesulfonic acid, p-toluenesulfonic acid, glutamic acid, aspartic acid, and acidic salts of glycine, alanine or serine. In some embodiments, the surface modified acid comprises a powdered or granulated acid selected from tartaric acid, fumaric acid, succinic acid, citric acid, lactic acid, and malic acid. In some embodiments, the surface modified acid comprises a powdered or granulated acid selected from tartaric acid.

In some embodiments, the neutral salt layer decreases the reactivity of the acid with other components of the formulation, such as the active ingredient. Many active ingredients, such as nilotinib, show improved solubility in the presence of acids (see Table 39 and Table 40) but degrade over time to form toxic impurities (see Example 5). In some embodiments, formulations with surface modified acids provide increased solubility while preserving the stability of the active ingredient.

In some embodiments, the surface modified acid is prepared by reacting a basic solution with the acid particle (e.g., powdered or granulated acid to form a neutral salt layer on the surface of the acid. In some embodiments, the neutral salt layer comprises an anion from the acid and a cation from the base. In some embodiments, the basic solution comprises a pharmaceutically acceptable base. In some embodiments, the pharmaceutically acceptable base is selected from sodium carbonate, potassium carbonate, sodium acetate, potassium acetate, sodium stearate, potassium stearate, lysine, arginine and histidine. In some embodiments, the pharmaceutically acceptable base is a carbonate base.

In some embodiments, the surface modified acid is prepared by reacting a basic solution with the powdered or granulated acid to form a neutral salt layer on the surface of the acid. In some embodiments, the concentration of the basic solution by weight is about 1% to about 30%. In some embodiments, the concentration of the basic solution by weight is about 5% to about 15%. In some embodiments, the concentration of the basic solution by weight is about 1% to about 2.5%, about 1% to about 5%, about 1% to about 7.5%, about 1% to about 10%, about 1% to about 12.5%, about 1% to about 15%, about 1% to about 20%, about 1% to about 25%, about 1% to about 30%, about 2.5% to about 5%, about 2.5% to about 7.5%, about 2.5% to about 10%, about 2.5% to about 12.5%, about 2.5% to about 15%, about 2.5% to about 20%, about 2.5% to about 25%, about 2.5% to about 30%, about 5% to about 7.5%, about 5% to about 10%, about 5% to about 12.5%, about 5% to about 15%, about 5% to about 20%, about 5% to about 25%, about 5% to about 30%, about 7.5% to about 10%, about 7.5% to about 12.5%, about 7.5% to about 15%, about 7.5% to about 20%, about 7.5% to about 25%, about 7.5% to about 30%, about 10% to about 12.5%, about 10% to about 15%, about 10% to about 20%, about 10% to about 25%, about 10% to about 30%, about 12.5% to about 15%, about 12.5% to about 20%, about 12.5% to about 25%, about 12.5% to about 30%, about 15% to about 20%, about 15% to about 25%, about 15% to about 30%, about 20% to about 25%, about 20% to about 30%, or about 25% to about 30%. In some embodiments, the concentration of the basic solution by weight is about 1%, about 2.5%, about 5%, about 7.5%, about 10%, about 12.5%, about 15%, about 20%, about 25%, or about 30%. In some embodiments, the concentration of the basic solution by weight is at least about 1% about 2.5% about 5%, about 7.5%, about 10%, about 12.5%, about 15%, about 20%, or about 25%. In some embodiments, the concentration of the basic solution by weight is at most about 2.5%, about 5%, about 7.5%, about 10%, about 12.5%, about 15%, about 20%, about 25%, or about 30%. In some embodiments, the weight ratio of the base to acid is about 1% to about 20%. In some embodiments, the weight ratio of the base to acid is about 1% to about 2%, about 1% to about 3%, about 1% to about 4%, about 1% to about 5%, about 1% to about 6%, about 1% to about 7%, about 1% to about 8%, about 1% to about 9%, about 1% to about 10%, about 1% to about 15%, about 1% to about 20%, about 2% to about 3%, about 2% to about 4%, about 2% to about 5%, about 2% to about 6%, about 2% to about 7%, about 2% to about 8%, about 2% to about 9%, about 2% to about 10%, about 2% to about 15%, about 2% to about 20%, about 3% to about 4%, about 3% to about 5%, about 3% to about 6%, about 3% to about 7%, about 3% to about 8%, about 3% to about 9%, about 3% to about 10%, about 3% to about 15%, about 3% to about 20%, about 4% to about 5%, about 4% to about 6%, about 4% to about 7%, about 4% to about 8%, about 4% to about 9%, about 4% to about 10%, about 4% to about 15%, about 4% to about 20%, about 5% to about 6%, about 5% to about 7%, about 5% to about 8%, about 5% to about 9%, about 5% to about 10%, about 5% to about 15%, about 5% to about 20%, about 6% to about 7%, about 6% to about 8%, about 6% to about 9%, about 6% to about 10%, about 6% to about 15%, about 6% to about 20%, about 7% to about 8%, about 7% to about 9%, about 7% to about 10%, about 7% to about 15%, about 7% to about 20%, about 8% to about 9%, about 8% to about 10%, about 8% to about 15%, about 8% to about 20%, about 9% to about 10%, about 9% to about 15%, about 9% to about 20%, about 10% to about 15%, about 10% to about 20%, or about 15% to about 20%. In some embodiments, the weight ratio of the base to acid is about 1%, about 2%, about 3%, about 4%, about 5%, about 6% about 7%, about 8%, about 9%, about 10%, about 15%, or about 20%. In some embodiments, the weight ratio of the base to acid is at least about 1%, about 2%, about 3%, about 4%, about 5%, about 6%, about 7%, about 8%, about 9%, about 10%, or about 15%. In some embodiments, the weight ratio of the base to acid is at most about 2%, about 3% about 4%, about 5%, about 6%, about 7%, about 8%, about 9%, about 10%, about 15% or about 20%.

In some embodiments, the external acid is present in the pharmaceutical composition in an amount of about 25 mg to about 500 mg. In some embodiments, the external acid is present in the pharmaceutical composition in an amount of about 50 mg to about 400 mg. In some embodiments, the external acid is present in the pharmaceutical composition in an amount of about 100 mg to about 300 mg. In some embodiments, the external acid is present in the pharmaceutical composition in an amount of about 200 mg to about 400 mg. In some embodiments, the external acid is present in the pharmaceutical composition in an amount of about 50 mg to about 500 mg. In some embodiments, the external acid is present in the pharmaceutical composition in an amount of about 50 mg to about 75 mg, about 50 mg to about 100 mg, about 50 mg to about 125 mg, about 50 mg to about 150 mg, about 50 mg to about 200 mg, about 50 mg to about 250 mg, about 50 mg to about 275 mg, about 50 mg to about 300 mg, about 50 mg to about 350 mg, about 50 mg to about 400 mg, about 50 mg to about 500 mg, about 75 mg to about 100 mg, about 75 mg to about 125 mg, about 75 mg to about 150 mg, about 75 mg to about 200 mg, about 75 mg to about 250 mg, about 75 mg to about 275 mg, about 75 mg to about 300 mg, about 75 mg to about 350 mg, about 75 mg to about 400 mg, about 75 mg to about 500 mg, about 100 mg to about 125 mg, about 100 mg to about 150 mg, about 100 mg to about 200 mg, about 100 mg to about 250 mg, about 100 mg to about 275 mg, about 100 mg to about 300 mg, about 100 mg to about 350 mg, about 100 mg to about 400 mg, about 100 mg to about 500 mg, about 125 mg to about 150 mg, about 125 mg to about 200 mg, about 125 mg to about 250 mg, about 125 mg to about 275 mg, about 125 mg to about 300 mg, about 125 mg to about 350 mg, about 125 mg to about 400 mg, about 125 mg to about 500 mg, about 150 mg to about 200 mg, about 150 mg to about 250 mg, about 150 mg to about 275 mg, about 150 mg to about 300 mg, about 150 mg to about 350 mg, about 150 mg to about 400 mg, about 150 mg to about 500 mg, about 200 mg to about 250 mg, about 200 mg to about 275 mg, about 200 mg to about 300 mg, about 200 mg to about 350 mg, about 200 mg to about 400 mg, about 200 mg to about 500 mg, about 250 mg to about 275 mg, about 250 mg to about 300 mg, about 250 mg to about 350 mg, about 250 mg to about 400 mg, about 250 mg to about 500 mg, about 275 mg to about 300 mg, about 275 mg to about 350 mg, about 275 mg to about 400 mg, about 275 mg to about 500 mg, about 300 mg to about 350 mg, about 300 mg to about 400 mg, about 300 mg to about 500 mg, about 350 mg to about 400 mg, about 350 mg to about 500 mg, or about 400 mg to about 500 mg. In some embodiments, the external acid is present in the pharmaceutical composition in an amount of about 50 mg, about 75 mg, about 100 mg, about 125 mg, about 150 mg, about 200 mg, about 250 mg, about 275 mg, about 300 mg, about 350 mg, about 400 mg, or about 500 mg. In some embodiments, the external acid is present in the pharmaceutical composition in an amount of at least about 50 mg, about 75 mg, about 100 mg, about 125 mg, about 150 mg, about 200 mg, about 250 mg, about 275 mg, about 300 mg, about 350 mg, or about 400 mg. In some embodiments, the external acid is present in the pharmaceutical composition in an amount of at most about 75 mg, about 100 mg, about 125 mg, about 150 mg, about 200 mg, about 250 mg, about 275 mg, about 300 mg, about 350 mg, about 400 mg, or about 500 mg.

In some embodiments, the external acid is present in the pharmaceutical composition in a weight percent of about 1% to about 50%. In some embodiments, the external acid is present in the pharmaceutical composition in a weight percent of about 5% to about 30%. In some embodiments, the external acid is present in the pharmaceutical composition in a weight percent of about 10% to about 30%. In some embodiments, the external acid is present in the pharmaceutical composition in a weight percent of about 5% to about 15%. In some embodiments, the external acid is present in the pharmaceutical composition in a weight percent of about 20% to about 40%. In some embodiments, the external acid is present in the pharmaceutical composition in a weight percent of about 10% to about 60%. In some embodiments, the external acid is present in the pharmaceutical composition in a weight percent of about 1% to about 5%, about 1% to about 10%, about 1% to about 15%, about 1% to about 20%, about 1% to about 25%, about 1% to about 30%, about 1% to about 35%, about 1% to about 40%, about 1% to about 45%, about 1% to about 50%, about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 10% to about 15%, about 10% to about 20%, about 10% to about 25%, about 10% to about 30%, about 10% to about 35%, about 10% to about 40%, about 10% to about 45%, about 10% to about 50%, about 15% to about 20%, about 15% to about 25%, about 15% to about 30%, about 15% to about 35%, about 15% to about 40%, about 15% to about 45%, about 15% to about 50%, about 20% to about 25%, about 20% to about 30%, about 20% to about 35%, about 20% to about 40%, about 20% to about 45%, about 20% to about 50%, about 25% to about 30%, about 25% to about 35%, about 25% to about 40%, about 25% to about 45% about 25% to about 50%, about 30% to about 35%, about 30% to about 40%, about 30% to about 45%, about 30% to about 50%, about 35% to about 40%, about 35% to about 45%, about 35% to about 50%, about 40% to about 45%, about 40% to about 50%, or about 45% to about 50%. In some embodiments, the external acid is present in the pharmaceutical composition in a weight percent of about 1%, about 5%, about 10%, about 15%, about 20%, about 25%, about 30%, about 35%, about 40%, about 45%, or about 50%. In some embodiments, the external acid is present in the pharmaceutical composition in a weight percent of at least about 1%, about 5%, about 10% about 15%, about 20%, about 25% about 30% about 35%, about 40%, or about 45%. In some embodiments, the external acid is present in the pharmaceutical composition in a weight percent of at most about 5%, about 10%, about 15% about 20%, about 25%, about 30%, about 35%, about 40%, about 45%, or about 50%.

In an exemplary embodiment, surface modified tartaric acid is prepared by reacting a basic solution of sodium carbonate with powdered tartaric acid to form a neutral salt layer on the tartaric acid. In some embodiments, the sodium carbonate aqueous solution is formulated at a concentration of about 5-30%. The amount of sodium carbonate is about 1-10% in a ratio by weight to the tartaric acid Second, the formulated sodium carbonate aqueous solution is added to tartaric acid powder particles having a particle size of about 40 to 60 mesh. After stirring, the tartaric acid powder particles are dried in a drying oven or a fluidized bed to yield the modified tartaric acid powder particles.

Oral Dosage Forms

The present pharmaceutical compositions can take the form of solutions, suspensions, emulsion, tablets, pills, pellets, capsules, capsules containing liquids, powders, suppositories, emulsions, suspensions, or any other form suitable for use. Preferred pharmaceutical compositions are formulated for oral delivery. In some embodiments, the pharmaceutically acceptable vehicle is a capsule. Capsules may be hard capsules or soft capsules, push-fit capsules made of gelatin, as well as soft, sealed capsules made of gelatin and a plasticizer (such as glycerol or sorbitol). In some embodiments, the capsule contains about 1000 mg of the pharmaceutical composition. In some embodiments, the capsule contains less than 1000 mg of the pharmaceutical composition. Capsules can be of any size. Examples of standard sizes include, but are not limited to those listed in Table 2, (#000, #00, #0, #1, #2, #3, #4, and #5). In some embodiments, the pharmaceutical composition is in the dosage form of a liquid filled into a hard capsule. In some embodiments, the pharmaceutical composition is in the dosage form of a liquid filled into a soft capsule. In some embodiments, the pharmaceutical composition is in the dosage form of a tablet. In some embodiments, the pharmaceutical composition comprises an amorphous solid dispersion. In some embodiments, the pharmaceutical composition comprises an amorphous solid dispersion in the dosage form of a tablet. In some embodiments, the pharmaceutical composition is in the dosage form of a multilayer tablet. In some embodiments, the tablet has one, two, three, four or more layers. In some embodiments, the tablet has an inner core and an outer core.

TABLE 2

| Size | Volume (mL) | Locked length (mm) | External diameter (mm) |
|---|---|---|---|
| 000 | 1.37 | 26.1 | 9.9 |
| 00 | 0.91 | 23.3 | 8.5 |
| 0 | 0.68 | 21.7 | 7.6 |
| 1 | 0.50 | 19.4 | 6.9 |
| 2 | 0.37 | 18.0 | 6.3 |
| 3 | 0.30 | 15.9 | 5.8 |
| 4 | 0.21 | 14.3 | 5.3 |

See, e.g., Remington's Pharmaceutical Sciences, page 1658-1659 (Alfonso Gennaro ed., Mack Publishing Company, Easton Pa., $18^{th}$ ed., 1990), which is incorporated by reference. In some embodiments, the capsules used herein are of size #00 or #0.

Methods of Administration

Pharmaceutical compositions described herein can be administered for the treatment or prevention of diseases. When used to treat or prevent diseases or disorders, pharmaceutical compositions may be administered or applied singly, or in combination with other agents. Pharmaceutical compositions may also be administered or applied singly, in combination with other pharmaceutically active agents. Provided herein are methods of treatment and prophylaxis by administration to a subject in need of such treatment of a therapeutically effective amount of a pharmaceutical composition of the invention. The subject may be an animal, e.g., a mammal such as a human. In some embodiments, pharmaceutical compositions described herein include a lipophilic API, a hydrophilic polymer, and a surfactant. In some embodiments, pharmaceutical compositions described herein include a lipophilic API, a hydrophilic polymer, and a phospholipid or poloxamer. In some embodiments, pharmaceutical compositions described herein include a lipophilic API, a hydrophilic polymer, and lecithin. In some embodiments, pharmaceutical compositions described herein include a lipophilic API, a non-ionic hydrophilic polymer, and lecithin. In some embodiments the API is nilotinib or a pharmaceutically acceptable salt thereof. In some embodiments, the API is nilotinib. In some embodiments, the API is a pharmaceutically acceptable salt of nilotinib. In some embodiments, the API is a lipophilic API. In some embodiments, the lipophilic API is one listed in Table 1, or a pharmaceutically acceptable salt thereof. In some embodiments, the lipophilic API, hydrophilic polymer, and the surfactant are formulated as an amorphous solid dispersion.

In some embodiments, the pharmaceutical compositions are administered orally. In some embodiments, the pharmaceutical compositions are administered in an oral liquid, semi-liquid or semisolid dosage form. In some embodiments, the pharmaceutical compositions are administered as a solid oral dosage form. In some embodiments, the pharmaceutical compositions are administered as a liquid oral dosage form. In some embodiments, the pharmaceutical compositions are administered as a pill, tablet, chewable tablet, specialty tablet, buccal tablet, sub-lingual tablet, orally-disintegrating tablet, capsule, gel capsule, soft gel capsule, hard gel capsule, specialty capsule, buccal capsule, sub-lingual capsule, orally-disintegrating capsule, powder, granule, crystal or orally dispersible film. In some embodiments, the pharmaceutical compositions are administered as a liquid or a capsule. In some embodiments, the pharmaceutical compositions are administered as a soft gel capsule.

In some embodiments, the pharmaceutical compositions are administered as a hard gel capsule.

In some embodiments, the pharmaceutical composition is formulated for oral administration. In some embodiments, the pharmaceutical composition is formulated for once daily dosing. In some embodiments, the pharmaceutical composition is formulated for twice daily dosing.

Conditions

In some embodiments, the pharmaceutical compositions may be used to inhibit Bcr-Abl tyrosine kinase/in a subject in need of inhibiting Bcr-Abl tyrosine kinase. In some embodiments, the subject has a disease or condition associated with tyrosine kinase. In some embodiments, pharmaceutical compositions described herein include a lipophilic API, a hydrophilic polymer, and a surfactant. In some embodiments, pharmaceutical compositions described herein include a lipophilic API, a hydrophilic polymer, and a surfactant. In some embodiments the API is nilotinib or a pharmaceutically acceptable salt thereof. In some embodiments, the API is a lipophilic API. In some embodiments, the lipophilic API is one listed in Table 1, or a pharmaceutically acceptable salt thereof. In some embodiments, the lipophilic API, hydrophilic polymer, and the surfactant are formulated as an amorphous solid dispersion.

In one aspect, described herein is a method of treating a disease or condition in a subject. The disease or condition can be a cancer. In some embodiments, a pharmaceutical composition described herein may be used to treat or prevent cancer. In some embodiments, the pharmaceutical compositions may be used to treat or prevent prostate cancer, breast cancer, ovarian cancer, endometrial cancer, bladder cancer, pancreatic cancer, hepatocellular cancer, kidney cancer, liver cancer, salivary gland carcinoma, hair loss, acne, hirsutism, ovarian cysts, polycystic ovary disease, precocious puberty, spinal and bulbar muscular atrophy, or age-related macular degeneration. In some embodiments, the pharmaceutical compositions may be used to treat or prevent prostate cancer. In some embodiments, the pharmaceutical compositions can be used to treat or prevent one or more of leukemia, Philadelphia chromosome (Ph+)-positive chronic myelogenous leukemia, gastrointestinal stromal tumor, Parkinson's disease, castration-resistant prostate cancer, metastatic castration-resistant prostate cancer, castration-recurrent prostate cancer, high-risk castration-sensitive prostate cancer, metastatic high-risk castration-sensitive prostate cancer, hormone-resistant prostate cancer, hormone-refractory prostate cancer, androgen-independent prostate cancer, androgen deprivation resistant prostate cancer, androgen ablation resistant prostate cancer, androgen depletion-independent prostate cancer, anti-androgen-recurrent prostate cancer, metastatic castration-resistant prostate cancer in patients who have already received prior chemotherapy containing docetaxel, newly diagnosed high risk metastatic hormone sensitive prostate cancer (mHSPC), metastatic castration resistant prostate cancer in patients who are asymptomatic, mildly symptomatic after failure of androgen deprivation therapy in whom chemotherapy is not yet clinically indicated, metastatic castration resistant prostate cancer in patients whose disease has progressed on or after a docetaxel-based chemotherapy regimen. In some embodiments, the pharmaceutical compositions are used to treat newly diagnosed adult patients with Philadelphia chromosome positive chronic myeloid leukemia (Ph+ CML) in chronic phase. In some embodiments, the pharmaceutical compositions are used to treat children with newly diagnosed Philadelphia chromosome-positive (Ph+) chronic myeloid leukemia (CML) in the chronic phase (CP). In some embodiments, the pharmaceutical compositions are used to treat chronic phase (CP) and accelerated phase (AP) Ph+ CML in adult patients resistant to or intolerant to prior therapy that included imatinib. In some embodiments, pharmaceutical compositions described herein include a lipophilic API, a hydrophilic polymer, and a surfactant. In some embodiments, pharmaceutical compositions described herein include a lipophilic API, a hydrophilic polymer, and a phospholipid or poloxamer. In some embodiments, pharmaceutical compositions described herein include a lipophilic API, a hydrophilic polymer, and lecithin. In some embodiments, pharmaceutical compositions described herein include a lipophilic API, a non-ionic hydrophilic polymer, and lecithin. In some embodiments the API is nilotinib or a pharmaceutically acceptable salt thereof. In some embodiments, the API is nilotinib. In some embodiments, the API is a pharmaceutically acceptable salt of nilotinib. In some embodiments, the API is a lipophilic API. In some embodiments, the lipophilic API is one listed in Table 1, or a pharmaceutically acceptable salt thereof. In some embodiments, the lipophilic API, hydrophilic polymer, and the surfactant are formulated as an amorphous solid dispersion. In some embodiments, the subject is an adult. In some embodiments, the subject is a child. In some embodiments, the subject is at least one year old. In some embodiments, the subject is less than one year old. In some embodiments, the subject is 1 to 12 years old. In some embodiments, the subject is 1 to 18 years old. In some embodiments, the subject is 12 to 18 years old. In some embodiments, the subject is at least 18 years old. In some embodiments, the subject is at least 24 years old. In some embodiments, the subject is 1 to 90 years old. In one aspect, described herein is a method of inhibiting tyrosine kinase that targets BCR-ABL. In some embodiments, the method comprises administering a pharmaceutical composition or an amorphous solid dispersion comprising nilotinib or a salt thereof.

In some embodiments, the pharmaceutical composition is used to treat a cancer selected from the group consisting of breast cancer, cancer is selected from the group consisting of acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, and Wilms tumor. In some embodiments, the disease or condition is associated with tyrosine kinase.

In some embodiments, pharmaceutical compositions described herein can be used in combination therapy with at least one other therapeutic agent. The pharmaceutical composition and the therapeutic agent can act additively or, more preferably, synergistically. In some embodiments, the pharmaceutical composition is administered concurrently with the administration of another therapeutic agent. In some embodiments, a pharmaceutical composition is administered prior or subsequent to administration of another therapeutic agent. In some embodiments, a pharmaceutical composition is administered in combination with omacetaxine, imatinib, selumetinib, ruxolitinib, asciminib, Pegylated Interferon Alfa-2B, Cetuximab, paclitaxel, or dasatinib. In some embodiments, pharmaceutical compositions described herein include a lipophilic API, a hydrophilic polymer, and a surfactant. In some embodiments, pharmaceutical compositions described herein include a lipophilic API, a hydrophilic polymer, and a phospholipid or poloxamer. In some embodiments, pharmaceutical compositions described herein include a lipophilic API, a hydrophilic polymer, and lecithin. In some embodiments, pharmaceutical compositions described herein include a lipophilic API, a non-ionic hydrophilic polymer, and lecithin. In some embodiments the API is nilotinib or a pharmaceutically acceptable salt thereof. In some embodiments, the API is nilotinib. In some embodiments, the API is a pharmaceutically acceptable salt of nilotinib. In some embodiments, the API is a lipophilic API. In some embodiments, the lipophilic API is one listed in Table 1, or a pharmaceutically acceptable salt thereof. In some embodiments, the lipophilic API, hydrophilic polymer, and the surfactant are formulated as an amorphous solid dispersion.

Methods of Manufacture

Disclosed herein is a method for preparing an amorphous solid dispersion, comprising the steps of (a) combining (i) an active pharmaceutical ingredient or a pharmaceutically acceptable salt thereof, (ii) one or more surfactants (e.g., polymeric non-ionic surfactants and phospholipids), (iii) a hydrophilic polymer (e.g., non-ionic hydrophilic polymer), (iv) optionally an adsorbent or adsorbents, (v) optionally other additional additives and (vi) a solvent or solvent mixture, thereby producing a liquid mixture (a solution or suspension), and (b) removing all or a part of the solvent from said mixture, thereby producing an amorphous solid dispersion. In some embodiments, the solvent is selected from an organic solvent and water. In some embodiments, the organic solvent is ethyl acetate, ethanol, isopropanol, or methanol, n-butanol, n-propanol, isopropanol, formic acid, nitromethane, ethanol, acetic acid, N-methylpyrrolidone, tetrahydrofuran (THF), methyl acetate, dimethylformamide, acetonitrile, dimethyl sulfoxide, dichloromethane (DCM), acetone, and any combination thereof. In some embodiments, the solvent is an alcohol. In some embodiments, the alcohol is ethanol. In some embodiments, the solvent is selected from dichloromethane, methanol, tetrahydrofuran, and acetone. In some embodiments, the solvent is selected from a mixture of these solvents. In some embodiments, combining comprises dissolving the active pharmaceutical ingredient or a pharmaceutically acceptable salt thereof, the surfactant, the non-ionic hydrophilic polymer, and optionally an adsorbent and/or additional additives in the solvent. In some embodiments, the adsorbent is suspended in the solvent. In some embodiments, removing of the solvent comprises spray-drying or rotor evaporation. In some embodiments, the API is an API of Table 1 or a pharmaceutically acceptable salt thereof.

In some embodiments, the method for preparing an amorphous solid dispersion, comprises the steps of (a) combining (i) an active pharmaceutical ingredient or a pharmaceutically acceptable salt thereof, (ii) one or more surfactants (e.g., polymeric non-ionic surfactants and phospholipids), (iii) a hydrophilic polymer (e.g., non-ionic hydrophilic polymer), (iv) optionally other additional additives and (v) a solvent or solvent mixture, to produce a liquid mixture or solution; (b) spraying the liquid mixture or solution onto an adsorbent or adsorbents; and (c) removing all or a part of the solvent from the liquid mixture or solution to produce an amorphous solid dispersion. In some embodiments, the solvent is selected from an organic solvent and water. In some embodiments, the organic solvent is ethyl acetate, ethanol, isopropanol, or methanol, n-butanol, n-propanol, isopropanol, formic acid, nitromethane, ethanol, acetic acid, N-methylpyrrolidone, tetrahydrofuran, methyl acetate, dimethylformamide, acetonitrile, dimethyl sulfoxide, dichloromethane (DCM), acetone, and any combination thereof. In some embodiments, the solvent is an alcohol. In some embodiments, the alcohol is ethanol. In some embodiments, the solvent is selected from dichloromethane, tetrahydrofuran, methanol and acetone. In some embodiments, the solvent is selected from a mixture of these solvents. In some embodiments, combining comprises dissolving the active pharmaceutical ingredient or a pharmaceutically acceptable salt thereof, the surfactant, the non-ionic hydrophilic polymer, and optionally additional additives in the solvent. In some embodiments, an amorphous solid dispersion is produced by a fluid-bed spraying and drying process. In some embodiments, an amorphous solid dispersion is produced by rotor evaporation.

In an exemplary manufacturing workflow, an amorphous solid dispersion is formed by first the API, hydrophilic polymer, surfactant, and optionally an additive or additives in a solvent or water at a room temperature or heated to form a clear solution. The clear solution is then spray dried to form an amorphous solid dispersion. Additionally, an amorphous solid dispersion is formed by first the API, hydrophilic polymer, surfactant, and optionally an additive or additives in a solvent or water in a room temperature or heated to form a clear solution. An adsorbent or a mixture of adsorbents is further added at a room temperature or heated to form a homogenous suspension. The homogenous suspension is then spray dried to form an amorphous solid dispersion. Following the formation of an amorphous solid dispersion, the amorphous solid dispersion is mixed with other additives and excipients used in the formulation. The mixture is then pressed into tablets or loaded into capsules.

A typical spray dryer comprises three chambers, a drying chamber, a cyclone chamber and a sample collection chamber. During the spray drying process, the spray dried dispersion solid is collected in the sample collection chamber. However, the solid may also reside on the surfaces of the drying chamber and cyclone chamber, thus causing a low production yield (a low amount of solid in the sample collection chamber). In some embodiments, the amorphous solid dispersions comprising of an API, a hydrophilic polymer and a surfactant have low production yields. When an adsorbent is incorporated into these amorphous solid dispersions, the production yield can be significantly increased. In some embodiments, the production yield of an amorphous solid dispersion with an adsorbent is increased by at least 10%, in comparison to the solid dispersion without an adsorbent. For clarity, the term of percentage means to be the absolute difference of the yields. For example, if the production yield of an amorphous solid dispersion without an adsorbent is 10% and the production yield of an amorphous solid dispersion with an adsorbent is 20%, the increase of the yield is the difference of these two yields, i.e., 10%. In some embodiments, the production yield of an amorphous solid dispersion with an adsorbent is increased by at least 20%, in comparison to the solid dispersion without an adsorbent. In some embodiments, the production yield of an amorphous solid dispersion with an adsorbent is increased by at least 30%, in comparison to the solid dispersion without an adsorbent. In some embodiments, the production yield of an amorphous solid dispersion with an adsorbent is increased by at least 40%, in comparison to the solid dispersion without an adsorbent. In some embodiments, the production yield of an amorphous solid dispersion with an adsorbent is increased by at least 50%, in comparison to the solid dispersion without an adsorbent. In some embodiments, the production yield of an amorphous solid dispersion with an adsorbent is increased by at least 60%, in comparison to the solid dispersion without an adsorbent. In some embodiments, the production yield of an amorphous solid dispersion with an adsorbent is increased by at least 70%, in comparison to the solid dispersion without an adsorbent. In some embodiments, the production yield of an amorphous solid dispersion with an adsorbent is increased by at least 80%, in comparison to the solid dispersion without an adsorbent. In some embodiments, the production yield of an amorphous solid dispersion with an adsorbent is increased by at least 90%, in comparison to the solid dispersion without an adsorbent.

EXAMPLES

Example 1: Compositions and Preparation Procedures of Amorphous Solid Dispersion Formulations of Lipophilic APIs Produced by Spray Drying Compositions of Spray Dried Amorphous Solid Dispersions of Lipophilic APIs Following tables, Table 3 to Table 13, list the compositions of some of the amorphous solid dispersions that have been prepared by spray drying.

TABLE 3

| | ASD Composition of Formulation 1 | | | ASD Composition of Formulation 2a | | |
|---|---|---|---|---|---|---|
| | Amount in one dose (mg) | % in formulation | Amount during preparation (g) | Amount in one dose (mg) | % in formulation | Amount during preparation (g) |
| API | Nilotinib HCl - 55 mg | 29.41% | 8.25 | Nilotinib HCl - 55 mg | 21.57% | 11.00 |
| Surfactant | — | — | — | Lecithin - 50 mg | 19.61% | 10.00 |
| Polymer | PVP K30 - 50 mg | 26.74% | 7.50 | PVP/VA64 - 50 mg | 19.61% | 10.00 |
| Other additives | Citric acid - 82 mg | 43.85% | 12.30 | Citric acid - 100 mg | 39.22% | 20.00 |
| Total | 187 mg | 100% | 28.05 | 255 mg | 100% | 51.00 |
| Solvent | Removed after spray drying | | Ethanol - 300 ml | Removed after spray drying | | Ethanol - 200 ml |

TABLE 4

| | ASD Composition of Formulation 2b | | | ASD Composition of Formulation 3a | | |
|---|---|---|---|---|---|---|
| | Amount in one dose (mg) | % in formulation | Amount during preparation (g) | Amount in one dose (mg) | % in formulation | Amount during preparation (g) |
| API | Nilotinib HCl - 55 mg | 21.57% | 11.0 | Nilotinib HCl - 55 mg | 21.57% | 8.25 |
| Surfactant | Poloxamer P188 - 50 mg | 19.61% | 10.0 | Lecithin - 100 mg | 39.22% | 15.0 |
| Polymer | PVP/VA64 - 50 mg | 19.61% | 10.0 | PVP K30 - 100 mg | 39.22% | 15.0 |

TABLE 4-continued

|  | ASD Composition of Formulation 2b | | | ASD Composition of Formulation 3a | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| Other additives | Citric acid - 100 mg | 39.22% | 20.0 | — | — | — |
| Total | 255 mg | 100% | 51.0 | 255 mg | 100% | 38.25 |
| Solvent | Removed after spray drying | | Ethanol - 200 ml | Removed after spray drying | | Ethanol - 750 ml |

TABLE 5

|  | ASD Composition of Formulation 3b | | | ASD Composition of Formulation 4 | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| API | Nilotinib HCl - 55 mg | 21.57% | 3.3 | Nilotinib HCl - 110.3 mg | 30.61% | 5.5 |
| Surfactant | Lecithin - 100 mg | 39.22% | 6.0 | Lecithin - 50 mg | 13.88% | 2.5 |
| Polymer | HP-β-CD - 100 mg | 39.22% | 6.0 | PVP K30 - 100 mg | 27.75% | 5.0 |
| Other additives | — | — | — | Silicon dioxide - 100 mg | 27.75% | 5.0 |
| Total | 255 mg | 100% | 15.3 | 360.3 mg | 100% | 18.0 |
| Solvent | Removed after spray drying | | Ethanol - 300 ml | Removed after spray drying | | DCM/MeOH (4:1) - 175 g |

TABLE 6

|  | ASD Composition of Formulation 5 | | | ASD Composition of Formulation 6 | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| API | Nilotinib free base - 100 mg | 28.6% | 12.0 | Nilotinib HCl - 110.3 mg | 30.6% | 5.5 |
| Surfactant | Lecithin - 50 mg | 14.3% | 6.0 | Lecithin - 50 mg | 13.9% | 2.5 |
| Polymer | HPMC - 200 mg | 57.1% | 24.0 | HPMC - 200 mg | 55.5% | 10.0 |
| Other additives | — | — | — | — | — | — |
| Total | 350 mg | 100% | 42.0 | 360.3 mg | 100% | 18.0 |
| Solvent | Removed after spray drying | | DCM/MeOH - (4/1) 420 g | Removed after spray drying | | DCM/MeOH 4/1) 175 g |

TABLE 7

|  | ASD Composition of Formulation 7 | | | ASD Composition of Formulation 8 | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| API | Nilotinib HCl - 110.3 mg | 26.9% | 5.5 | Nilotinib HCl - 110.3 mg | 24.0% | 5.5 |
| Surfactant | Lecithin - 100 mg | 24.4% | 5.0 | Lecithin - 100 mg | 21.7% | 5.0 |

TABLE 7-continued

|  | ASD Composition of Formulation 7 | | | ASD Composition of Formulation 8 | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| Polymer | PVP K30 - 100 mg | 24.4% | 5.0 | PVP K30 - 100 mg | 21.7% | 5.0 |
| Other additives | Silicon dioxide - 100 mg | 24.4% | 5.0 | Silicon dioxide - 150 mg | 32.6% | 7.5 |
| Total | 410.3 mg | 100% | 20.5 | 460.3 mg | 100% | 23.0 |
| Solvent | Removed after spray drying | | DCM/MeOH - (4:1) - 175 g | Removed after spray drying | | DCM/MeOH - (4:1) - 175 g |

TABLE 8

|  | ASD Composition of Formulation 9 | | | ASD Composition of Formulation 10 | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| API | Nilotinib HCl - 110.3 mg | 21.6% | 5.5 | Abiraterone acetate - 100 mg | 20% | 10 |
| Surfactant | Lecithin - 100 mg | 19.6% | 5.0 | Lecithin - 100 mg | 20% | 10 |
| Polymer | PVP K30 - 150 mg | 29.4% | 7.5 | HPMC - 150 mg | 30% | 15 |
| Other additives | Silicon dioxide - 150 mg | 29.4% | 7.5 | Silicon dioxide - 150 mg | −30% | 15 |
| Total | 510.3 mg | 100% | 25.5 | 500 mg | 100% | 50 |
| Solvent | Removed after spray drying | | DCM/MeOH - (4:1) - 175 g | Removed after spray drying | | DCM/MeOH - (5/2) 450 g |

TABLE 9

|  | ASD Composition of Formulation 11 | | | ASD Composition of Formulation 12 | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| API | Nilotinib HCl - 55 mg | 10.8% | 110 | Nilotinib HCl - 55 mg | 10.8% | 8.25 |
| Surfactant | Lecithin - 100 mg | 19.7% | 200 | Lecithin - 100 mg | 19.7% | 15 |
|  | Kolliphor RH40 - 100 mg | 19.7% | 200 | Vitamin E-TPGS - 100 mg | 19.7% | 15 |
| Polymer | PVP K30 - 100 mg | 19.7% | 200 | HPMC E5 - 100 mg | 19.7% | 15 |
| Other additives | Silicon dioxide - 150 mg | 29.6% | 300 | Silicon dioxide - 150 mg | 29.6% | 22.5 |
|  | BHA - 2 mg | 0.4% | 4 | BHA - 2 mg | 0.4% | 0.3 |
|  | BHT - 0.4 mg | 0.1% | 0.8 | BHT - 0.4 mg | 0.1% | 0.06 |
| Total | 507.4 mg | 100% | 1017.8 | 507.4 mg | 100% | 76.11 |
| Solvent | Removed after spray drying | | DCM/MeOH - (4:1) - 7000 g | Removed after spray drying | | DCM/MeOH - (4:1) - 525 g |

TABLE 10

| | ASD Composition of Formulation 13 | | | ASD Composition of Formulation 14 | | |
|---|---|---|---|---|---|---|
| | Amount in one dose (mg) | % in formulation | Amount during preparation (g) | Amount in one dose (mg) | % in formulation | Amount during preparation (g) |
| API | Nilotinib HCl - 83 mg | 15.5% | 8.3 | Nilotinib HCl - 110 mg | 19.6% | 16.5 |
| Surfactant | Lecithin - 100 mg | 18.7% | 10 | Lecithin - 100 mg | 17.8% | 15 |
| | Vitamin E-TPGS - 100 mg | 18.7% | 10 | Vitamin E-TPGS - 100 mg | 17.8% | 15 |
| Polymer | HPMC E5 - 100 mg | 18.7% | 10 | HPMC E5 - 100 mg | 17.8% | 15 |
| Other additives | Silicon dioxide - 150 mg | 28.0% | 15 | Silicon dioxide - 150 mg | 26.7% | 22.5 |
| | BHA - 2 mg | 0.4% | 0.2 | BHA - 2 mg | 0.4% | 0.3 |
| | BHT - 0.4 mg | 0.1% | 0.04 | BHT - 0.4 mg | 0.1% | 0.06 |
| Total | 535.4 mg | 100% | 53.5 | 562.4 mg | 100% | 84.36 |
| Solvent | Removed after spray drying | | DCM/MeOH - (4:1) - 350 g | Removed after spray drying | | DCM/MeOH - (4/1) 525 g |

TABLE 11

| | ASD Composition of Formulation 15 | | | ASD Composition of Formulation 16 | | |
|---|---|---|---|---|---|---|
| | Amount in one dose (mg) | % in formulation | Amount during preparation (g) | Amount in one dose (mg) | % in formulation | Amount during preparation (g) |
| API | Nilotinib HCl - 83 mg | 15.6% | 4.2 | Nilotinib HCl - 83 mg | 15.6% | 4.2 |
| Surfactant | Lecithin - 100 mg | 18.8% | 5 | Lecithin - 100 mg | 18.8% | 5 |
| | Vitamin E-TPGS - 100 mg | 18.8% | 5 | Vitamin E-TPGS - 100 mg | 18.8% | 5 |
| Polymer | HPMC E5 - 50 mg | 9.4% | 2.5 | — | — | — |
| | HPMC E50 - 50 mg | 9.4% | 2.5 | HPMC E50 - 100 mg | 18.8% | 5 |
| Other additives | Silicon dioxide - 150 mg | 28.1% | 7.5 | Silicon dioxide - 150 mg | 28.1% | 7.5 |
| Total | 533 mg | 100% | 26.7 | 533 mg | 100% | 26.7 |
| Solvent | Removed after spray drying | | DCM/MeOH - (4:1) - 227.5 g | Removed after spray drying | | DCM/MeOH - (4/1) 227.5 g |

TABLE 12

| | ASD Composition of Formulation 17 | | | ASD Composition of Formulation 18 | | |
|---|---|---|---|---|---|---|
| | Amount in one dose (mg) | % in formulation | Amount during preparation (g) | Amount in one dose (mg) | % in formulation | Amount during preparation (g) |
| API | Nilotinib HCl - 83 mg | 15.6% | 4.2 | Nilotinib HCl - 83 mg | 15.6% | 4.2 |
| Surfactant | Lecithin - 100 mg | 18.8% | 5 | Lecithin - 100 mg | 18.8% | 5 |
| | Vitamin E-TPGS - 100 mg | 18.8% | 5 | Vitamin E-TPGS - 100 mg | 18.8% | 5 |
| Polymer | HPMC E5 - 90 mg | 16.9% | 4.5 | HPMC E5 - 80 mg | 15.0% | 4 |
| | HPMC E50 - 10 mg | 1.9% | 0.5 | HPMC E50 - 20 mg | 3.8% | 1 |

TABLE 12-continued

|  | ASD Composition of Formulation 17 | | | ASD Composition of Formulation 18 | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| Other additives | Silicon dioxide - 150 mg | 28.1% | 7.5 | Silicon dioxide - 150 mg | 28.1% | 7.5 |
| Total | 533 mg | 100% | 26.7 | 533 mg | 100% | 26.7 |
| Solvent | Removed after spray drying | | DCM/MeOH - (4:1) - 227.5 g | Removed after spray drying | | DCM/MeOH - (4:1) - 227.5 g |

TABLE 13

|  | ASD Composition of Formulation 19 | | | ASD Composition of Formulation 20 | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| API | Nilotinib HCl - 83 mg | 15.6% | 4.2 | Nilotinib HCl - 110 mg | 21.6% | 5.5 |
| Surfactant | Lecithin - 100 mg | 18.8% | 5 | — | — | — |
|  | Vitamin E-TPGS - 100 mg | 18.8% | 5 | — | — | — |
| Polymer | HPMC E5 - 70 mg | 13.1% | 3.5 | HPMC E5 - 400 mg | 78.4% | 20 |
|  | HPMC E50 - 30 mg | 5.6% | 1.5 | — | — | — |
| Other additives | Silicon dioxide - 150 mg | 28.1% | 7.5 | — | — | — |
| Total | 533 mg | 100% | 26.7 | 510 mg | 100% | 25.5 |
| Solvent | Removed after spray drying | | DCM/MeOH - (4:1) - 227.5 g | Removed after spray drying | | DCM/MeOH - (4/1) 175 g |

TABLE 14

|  | ASD Composition of Formulation 21 | | | ASD Composition of Formulation 22 | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| API | Nilotinib HCl - 55 mg | 26.8 | 2.75 | Nilotinib HCl - 55 mg | 21.6 | 2.75 |
| Surfactant | Vitamin E-TPGS - 50 mg | 24.4 | 2.5 | Vitamin E-TPGS - 50 mg | 19.6 | 2.5 |
| Polymer | HPMC E5 - 100 mg | 48.8 | 5.0 | HPMC E5 - 100 mg | 39.2 | 5.0 |
| Other additives | — | — | — | Silicon dioxide - 50 mg | 19.6 | 2.5 |
| Total | 205 mg | 100% | 10.25 | 255 | 100% | 12.75 |
| Solvent | Removed after spray drying | | DCM/MeOH - (4:1) - 175 g | Removed after spray drying | | DCM/MeOH - (4:1) - 175 g |

TABLE 15

ASD Composition of Formulation 23

|   | Amount in one dose (mg) | % in formulation | Amount during preparation (g) |
|---|---|---|---|
| API | Nilotinib HCl—55 mg | 18.0 | 2.75 |
| Surfactant | Vitamin E-TPGS—50 mg | 16.4 | 2.5 |
| Polymer | HPMC E5—100 mg | 32.8 | 5.0 |
| Other additives | Silicon dioxide—100 mg | 32.8 | 5.0 |
| Total | 305 mg | 100% | 15.25 |
| Solvent | Removed after spray drying | | DCM/MeOH-(4:1)—175 g |

General Preparation for the Amorphous Solid Dispersion by Spray Drying

The active pharmaceutical ingredient, polymer, and optionally any surfactants and/or additives were dissolved in a solvent or solvent mixture at a room temperature and up to 80° C. to form a clear solution. The total amount of solids added into the solution is about 5% to 15%. In some cases when an adsorbent was added, a homogenies suspension was formed. A bench top spray dryer was preheated until a steady state was achieved. The solution was then introduced into the spray dryer via flash atomization at a feed rate of about 3-5 rpm, at an inlet drying gas temperature of about 50-150° C., and an outlet temperature of about 40-45° C., and a pressure of about 2-3 bar. After collection, the particles were placed into a convection tray dryer operated at 30° C. or above.

Specifically, the processing parameters of the spray drying process for the formulations in the tables from Table 3-Table 8 are listed in Table 16 and Table 17.

TABLE 16

|   | ASD of Formulation 1 | ASD of Formulation 2a | ASD of Formulation 2b | ASD of Formulation 3a | ASD of Formulation 3b | ASD of Formulation 4 |
|---|---|---|---|---|---|---|
| Spray drying solution temperature (° C.) | Room temperature | 50~60 | 50~60 | Room temperature | 35~45 | Room temperature |
| Feed rate (rpm) | 8 | 9 | 9 | 9 | 10 | 3.0 |
| Inlet temperature (° C.) | 117 | 117 | 115 | 117 | 135 | 55.0 |
| Outlet temperature (° C.) | 71 | 71 | 70 | 71 | 70 | 41.0 |

TABLE 17

|   | ASD of Formulation 5 | ASD of Formulation 6 | ASD of Formulation 7 | ASD of Formulation 8 | ASD of Formulation 9 | ASD of Formulation 10 |
|---|---|---|---|---|---|---|
| Spray drying solution temperature (° C.) | Room temperature | Room temperature | Room temperature | Room temperature | Room temperature | Room temperature |
| Feed rate (rpm) | 3.0 | 3.0 | 3.0 | 3.0 | 3.0 | 3.0 |
| Inlet temperature (° C.) | 55.0 | 55.0 | 55.0 | 55.0 | 55.0 | 55 |
| Outlet temperature (° C.) | 42.0 | 42.0 | 41.0 | 42.0 | 42.0 | 40 |

The particle size distributions of these amorphous solid dispersions were measured by Malvern Particle Size Analyzer 3000 using a dry powder method with a dispersive pressure of 2 bar, and the results are shown in Table 18 and Table 19.

TABLE 18

|  | ASD of Formulation 1 | ASD of Formulation 2a | ASD of Formulation 2b | ASD of Formulation 3a | ASD of Formulation 3b | ASD of Formulation 4 |
| --- | --- | --- | --- | --- | --- | --- |
| $D_{10}$ | 3.57 μm | 8.93 μm | 9.95 μm | 2.03 μm | 1.90 μm | 3.08 μm |
| $D_{50}$ | 16.1 μm | 33.5 μm | 56.1 μm | 5.66 μm | 6.41 μm | 15.6 μm |
| $D_{90}$ | 245 μm | 252 μm | 180 μm | 27.6 μm | 17.7 μm | 55.2 μm |

TABLE 19

|  | ASD of Formulation 5 | ASD of Formulation 6 | ASD of Formulation 7 | ASD of Formulation 8 | ASD of Formulation 9 |
| --- | --- | --- | --- | --- | --- |
| $D_{10}$ | 2.34 μm | 3.03 μm | 3.20 μm | 2.90 μm | 3.10 μm |
| $D_{50}$ | 7.72 μm | 11.3 μm | 9.94 μm | 11.0 μm | 10.2 μm |
| $D_{90}$ | 21.7 μm | 524 μm | 35.6 μm | 38.5 μm | 38.4 μm |

Figure 1B:
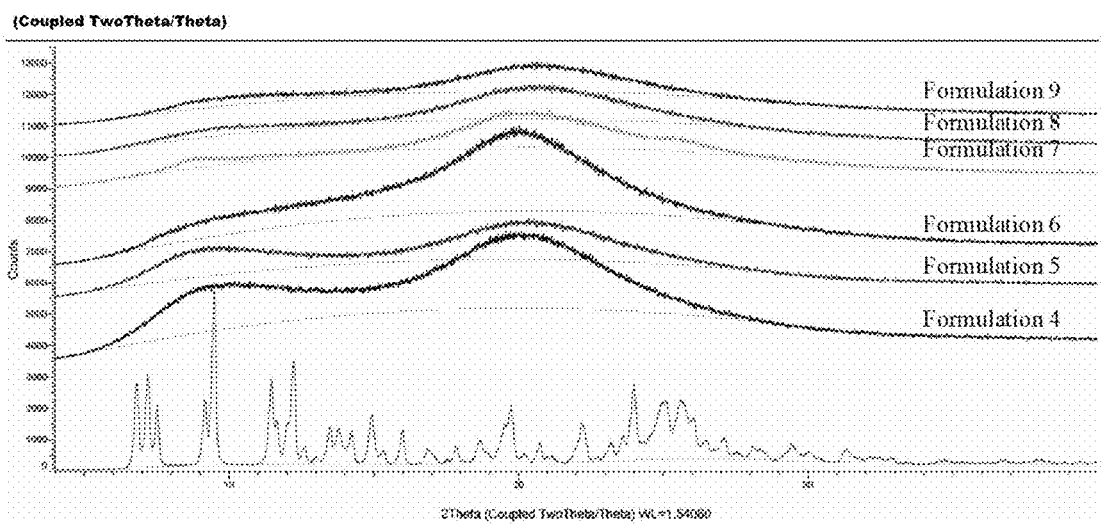

XRPD showed these formulations to be amorphous, with no detectable crystallinity (FIG. 1a and FIG. 1b).

Example 2: The Difference of the Production Yields of Amorphous Solid Dispersions with and without an Adsorbent For the amorphous solid dispersions with and without silicon dioxide (as the adsorbent), the production yields of these ASDs are listed in the following table, Table 20.

TABLE 20

|  | ASD without adsorbent | | | ASD with adsorbent | | |
| --- | --- | --- | --- | --- | --- | --- |
|  | Amount in one dose (mg) | % in formulation | Amount during preparation (g) | Amount in one dose (mg) | % in formulation | Amount during preparation (g) |
| Nilotinib free base | 100 | 28.6% | 5.0 | 100 | 28.6% | 5.0 |
| Lecithin | 50 | 14.3% | 2.5 | 50 | 14.3% | 2.5 |
| PVP K30 | 200 | 57.1% | 10.0 | 100 | 28.6% | 5.0 |
| Silicon dioxide | 0 | 0 | 0 | 100 | 28.6% | 5.0 |
| Total | 350 | 100% | 17.5 | 350 | 100% | 17.5 |
| Solvent |  | Removed after spray drying | DCM/MeOH - (4:1) - 175 g |  | Removed after spray drying | DCM/MeOH - (4:1) - 175 g |
| Production Yield (%) |  | <3% |  |  | 34.6% |  |

Results in Table 20 show that for some amorphous solid dispersions with an adsorbent, the production yield of the spray drying process can be significantly improved.

Example 3: Compositions and Preparation Procedures of Tablets or Capsules of Amorphous Solid Dispersion Formulations of Lipophilic APIs Capsule Formulations For Formulation 1 to Formulation 3b, a single dose amorphous solid dispersion powder was filled into a Size 0 or Size 00 gelatin capsule to be used in further studies, as shown in Table 21.

TABLE 21

|  | Formulation 1 | Formulation 2a | Formulation 2b | Formulation 3a | Formulation 3b |
| --- | --- | --- | --- | --- | --- |
| Weight of ASD (mg) | 187 | 255 | 255 | 255 | 255 |
| Gelatin Capsule | Size 00 | Size 00 | Size 00 | Size 0 | Size 0 |

Formulations 4, 5, and 6 were prepared based on Table 22 and filled into capsules.

TABLE 22

|  | Formulation 4 | Formulation 5 | Formulation 6 |
|---|---|---|---|
| Dry granulation materials | Formulation 4 ASD—360.3 mg PVPP—23.5 mg MCC—77.1 mg Silicon dioxide—4.7 mg MgSt—2.3 mg | Formulation 5 ASD—350 mg PVPP—23 mg MCC—82.4 mg MgSt—2.3 mg | Formulation 6 ASD—360.3 mg PVPP—23.5 mg MCC—72.4 mg Silicon dioxide—9.4 mg MgSt—2.3 mg |
| External granule materials | MgSt—2.4 mg | MgSt—2.3 mg | MgSt—2.4 mg |
| Total weight | 470.3 mg | 460 mg | 470.3 mg |

The formulations were prepared by mixing the relative amounts of amorphous solid dispersions with other excipients for dry granulation. The dry granulation was performed by slugging, milling and screening to form dry granules. Additional excipients were mixed with the dry granules and then filled into Size 0 capsules.

Tablet Formulations

Formulations 8a and 8b were prepared based on the following table and compressed into tablets.

TABLE 23

|  | Formulation 8a | Formulation 8b |
|---|---|---|
| Dry granulation materials | Formulation 8 ASD—460.3 mg PVPP—24 mg MCC KG802—160 mg Silicon dioxide—8 mg MgSt—4 mg | Formulation 8 ASD—460.3 mg PVPP—24 mg MCC KG802—160 mg MgSt—8 mg MgSt—4 mg |
| External granule materials | MCC PH102—115.7 mg PVPP—24 mg — MgSt—4 mg | MCC PH102—115.7 mg PVPP—24 mg 6% Surface modified tartaric acid—100 mg MgSt—4 mg |
| Total weight | 800 mg | 900 mg |

The formulations were prepared by mixing the relative amounts of amorphous solid dispersions with other excipients for dry granulation. The dry granulation was performed by slugging, milling and screening to form dry granules. Additional excipients were mixed with the dry granules and then compressed into tablets.

For Formulation 8b, the surface modified tartaric acid was prepared by spraying of a 300 g of 10% sodium carbonate aqueous solution (30 g of $Na_2CO_3$ in 270 g of the aqueous solution) onto 500 g of tartaric acid in a powder bed and then dried in a fluid bed equipment. About 6% weight of sodium carbonate based on tartaric acid was sprayed onto the tartaric acid surface. The sodium carbonate solution reacts with the tartaric acid powder to form a neutral salt layer and generate the surface modified acid. The surface modified acid differs from an unmodified acid, in that there is a protective neutral layer that at least partially insulates the acid and reduces interaction with other compounds in the formulation, such as the active ingredient.

Formulation 10 was prepared by mixing the ASD for Formulation 10 (shown in Table 8) with additional excipients and then compressed into tablets, based on Table 24.

TABLE 24

|  | Formulation 10 |
|---|---|
| ASD | Formulation 10 ASD—500 mg |
| Additional Excipients | SLS—40 mg MCC—133.5 mg CMS-Na—68 mg Surface modified tartaric acid—100 mg MgSt—8.5 mg |
| Total weight | 850 mg |

The tablet formulations shown in Table 25 to Table 31 were prepared by mixing the ASD compositions for Formulation 11 to Formulation 23 (shown in Table 9 to Table 15) with additional excipients and then compressed into tablets.

TABLE 25

|  | Formulation 11a | Formulation 11b |
|---|---|---|
| Dry granulation materials | Formulation 11 ASD—507.4 mg PVPP—144.4 mg MgSt—4 mg | Formulation 11 ASD—507.4 mg PVPP—144.4 mg MgSt—4 mg |
| External granule materials | MCC PH102—108.2 mg Ac-Di-Sol—32 mg — MgSt—4 mg | MCC PH102—108.2 mg Ac-Di-Sol—32 mg tartaric acid—100 mg MgSt—4 mg |
| Total weight | 800 mg | 900 mg |

TABLE 26

|  | Formulation 12a | Formulation 12b | Formulation 12c |
|---|---|---|---|
| Dry granulation materials | Formulation 12 ASD—507.4 mg PVPP—144.4 mg MgSt—4 mg | Formulation 12 ASD—507.4 mg PVPP—144.4 mg MgSt—4 mg | Formulation 12 ASD—507.4 mg PVPP—144.4 mg MgSt—4 mg |
| External granule materials | MCC PH102—108.2 mg Ac-Di-Sol—32 mg tartaric acid—100 mg MgSt—4 mg | MCC PH102—108.2 mg Ac-Di-Sol—32 mg 2% Surface modified tartaric acid—100 mg MgSt—4 mg | MCC PH102—108.2 mg Ac-Di-Sol—32 mg 6% Surface modified tartaric acid—100 mg MgSt—4 mg |
| Total weight | 900 mg | 900 mg | 900 mg |

TABLE 27

|  | Formulation 13 | Formulation 14 |
| --- | --- | --- |
| Dry granulation materials | Formulation 13<br>ASD—533 mg<br>PVPP—116.4 mg<br>MgSt—4 mg | Formulation 14<br>ASD—562.4 mg<br>PVPP—89.4 mg<br>MgSt—4 mg |
| External granule materials | MCC PH102—108.2 mg<br>Ac-Di-Sol—32 mg<br>2% Surface modified tartaric acid—100 mg<br>MgSt—4 mg | MCC PH102—108.2 mg<br>Ac-Di-Sol—32 mg<br>2% Surface modified tartaric acid—100 mg<br>MgSt—4 mg |
| Total weight | 900 mg | 900 mg |

In Table 26 and Table 27, the 2% surface modified tartaric acid in Formulation 12b, Formulation 13 and Formulation 14 was prepared by spraying of a 400 g of 10% sodium carbonate aqueous solution (40 g of $Na_2CO_3$ in 360 g of the aqueous solution) onto 2000 g of tartar acid powder bed and then dried in a fluid bed equipment. About 2% weight of sodium carbonate was sprayed onto the tartaric acid surface. In Table 26, the 6% surface modified tartaric acid in Formulation 12c was prepared based on Formulation 8b shown in Table 23.

TABLE 28

|  | Formulation 13a | Formulation 13b | Formulation 13c |
| --- | --- | --- | --- |
| Dry granulation materials | Formulation 13<br>ASD—533 mg<br>MCC KG802—150.8 mg<br>MgSt—4 mg | Formulation 13<br>ASD—533 mg<br>MCC KG802—118.8 mg<br>MgSt—4 mg | Formulation 13<br>ASD—533 mg<br>MCC KG802—118.8 mg<br>MgSt—4 mg |
| External granule materials | MCC PH102—108.2 mg<br>—<br>MgSt—4 mg | MCC PH102—108.2 mg<br>Ac-Di-Sol—32 mg<br>MgSt—4 mg | MCC PH102—108.2 mg<br>PVPP—32 mg<br>MgSt—4 mg |
| Total weight | 800 mg | 800 mg | 800 mg |

TABLE 29

|  | Formulation 15 | Formulation 16 | Formulation 17 |
| --- | --- | --- | --- |
| Dry granulation materials | Formulation 15<br>ASD—533 mg<br>PVPP—150.8 mg<br>MgSt—4 mg | Formulation 16<br>ASD—533 mg<br>PVPP—150.8 mg<br>MgSt—4 mg | Formulation 17<br>ASD—533 mg<br>PVPP—150.8 mg<br>MgSt—4 mg |
| External granule materials | MCC PH102—108.2 mg<br>MgSt—4 mg | MCC PH102—108.2 mg<br>MgSt—4 mg | MCC PH102—108.2 mg<br>MgSt—4 mg |
| Total weight | 800 mg | 800 mg | 800 mg |

TABLE 30

|  | Formulation 18 | Formulation 19 |
| --- | --- | --- |
| Dry granulation materials | Formulation 18<br>ASD—533 mg<br>PVPP—150.8 mg<br>MgSt—4 mg | Formulation 19<br>ASD—533 mg<br>PVPP—150.8 mg<br>MgSt—4 mg |
| External granule materials | MCC PH102—108.2 mg<br>MgSt—4 mg | MCC PH102—108.2 mg<br>MgSt—4 mg |
| Total weight | 800 mg | 800 mg |

TABLE 31

|  | Formulation 20a | Formulation 20b |
| --- | --- | --- |
| Dry granulation materials | Formulation 20 ASD—510 mg<br>Silicon dioxide—16 mg<br>PVPP—157.8 mg<br>MgSt—4 mg | Formulation 20 ASD—510 mg<br>Silicon dioxide—16 mg<br>MCC PH102—157.8 mg<br>MgSt—4 mg |
| External granule materials | MCC PH102—108.2 mg<br>MgSt—4 mg<br>2% Surface modified tartaric acid—100 mg | MCC PH102—108.2 mg<br>MgSt—4 mg<br>2% Surface modified tartaric acid—100 mg |
| Total weight | 900 mg | 900 mg |

TABLE 32

|  | Formulation 21 | Formulation 22 | Formulation 23 |
| --- | --- | --- | --- |
| Dry granulation materials | Formulation 21<br>ASD - 205 mg<br>PVPP - 150 mg<br>MgSt - 4.5 mg<br>MCC PH102 - 200 mg | Formulation 22<br>ASD - 255 mg<br>PVPP - 100 mg<br>MgSt - 4.5 mg<br>MCC PH102 - 200 mg | Formulation 23<br>ASD - 305 mg<br>PVPP - 50 mg<br>MgSt - 4.5 mg<br>MCC PH102 - 200 mg |
| External granule materials | Ac-Di-Sol -36 mg<br>MgSt - 4.5 mg<br>2% Surface modified tartaric acid - 300 mg | Ac-Di-Sol -36 mg<br>MgSt - 4.5 mg<br>2% Surface modified tartaric acid - 300 mg | Ac-Di-Sol -36 mg<br>MgSt - 4.5 mg<br>2% Surface modified tartaric acid - 300 mg |
| Total weight | 900 mg | 900 mg | 900 mg |

Similar to Formulation 12b, Formulation 13 and Formulation 14 shown in Table 26 and Table 27, the 2% surface modified tartaric acid used in Formulations 20a, 20b, 21, 22, and 23 shown in Tables 31 and 32 was prepared by spraying about 2% weight of sodium carbonate onto the tartaric acid surface.

While particular embodiments described herein have been shown and described herein, such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope and that methods and structures within the scope of these claims and their equivalents be covered thereby.

Example 4: Oral Bioavailability of ASD Formulations in Dogs

The in vivo pharmacokinetic properties ($T_{max}$, $C_{max}$, AUC) of nilotinib compositions were examined by administering such compositions to beagle dogs, as described below.

Comparison of Bioavailability of ASD Formulations with that of TASIGNA® in Dogs

Beagle dogs, (3 male and 3 female), were fasted for 12 hours before administration. Test formulations were orally administered to each dog with 50 mL of water at the time of the administration. Blood samples were collected at 0.25, 0.5, 1, 1.5, 2, 3, 4, 8, 12, 24 hours after administration and the concentrations of nilotinib in plasma were determined. From these measurements, $C_{max}$, $T_{max}$ and AUC were calculated and are presented in Table 33 to Table 35 below.

Table 33 compares pharmaceutical formulations with various physical states. Formulation 1 is an amorphous solid dispersion (ASD) formulation without surfactant and with an acid. Although the nilotinib HCl is present in a 55 mg dose (equivalent to 50 mg of nilotinib, a ratio of 1.1 between nilotinib HCl and nilotinib), the bioavailability is comparable to a 220 mg dose (equivalent to 200 mg of nilotinib, a ratio of 1.1 between nilotinib HCl and nilotinib) in the listed drug product TASIGNA®. The dog study was performed by a cross-over design for the formulations listed in Table 33. The drug product TASIGNA® is marketed in three dosage forms of nilotinib hydrochloride at equivalent doses of 50 mg, 150 mg, and 200 mg of nilotinib free base. The dosage forms are formulated as hard capsules and include the following excipients: lactose monohydrate, crospovidone, poloxamer, colloidal silica, anhydrous/colloidal silicon dioxide, and magnesium stearate. The nilotinib hydrochloride in the TASIGNA® formulation is not known to be incorporated into an amorphous solid dispersion. The API in the TASIGNA® formulation is in its crystalline state, while the API in Formulation 1 is part of amorphous solid dispersion (ASD).

Table 33 shows the benefits of using an amorphous solid dispersion to carry the API. The $C_{max}$ and $AUC_\infty$ for Formulation 1 is similar to that of TASIGNA®, despite TASIGNA® having four times the amount of API.

TABLE 33

| Formulation | Nilotinib equivalent | $T_{max}$ (hrs) | $C_{max}$ (ng/ml) | $AUC_\infty$ (ng/ml*hr) |
|---|---|---|---|---|
| Formulation 1 | 50 mg | 2.5 | 1,396.2 ± 947.4 | 8,296 ± 4,677 |
| TASIGNA | 200 mg | 4 | 1,555.9 ± 972.0 | 9,946 ± 6,539 |

Table 34 compares formulations with amorphous solid dispersions comprising 55 mg of nilotinib HCl (equivalent to 50 mg of nilotinib free base) and various polymers, surfactants, and acids (Formulations 2a and 2b) with a 220 mg dose (equivalent to 200 mg nilotinib) in the listed drug product TASIGNA®. The dog study was performed in a cross-over design. Table 34 highlights the unexpected advantage of incorporating lecithin or Polaxamer 188 into an amorphous solid dispersion with nilotinib HCl and polymer. Despite using only one quarter of nilotinib HCl, the bioavailability of the API is twice that of the commercialized drug product. Reducing API loading while maintaining bioavailability can lead to a reduction in unwanted side effects.

TABLE 34

| Formulation | Nilotinib equivalent | $T_{max}$ (hrs) | $C_{max}$ (ng/ml) | $AUC_\infty$ (ng/ml*hr) |
|---|---|---|---|---|
| 2a | 50 mg | 2 | 2,023.6 ± 1,431.6 | 13,012 ± 11,227 |
| 2b | 50 mg | 2.5 | 2,113.1 ± 1,287.0 | 12,798 ± 11,234 |
| TASIGNA | 200 mg | 1.25 | 1,278.2 ± 989.0 | 6,517 ± 6,316 |

Table 35 compares acid free amorphous solid dispersions comprising 55 mg of nilotinib HCl (equivalent to 50 mg of nilotinib) and various polymers, surfactants, and acids (Formulations 3a and 3b) with a 220 mg dose (equivalent to 200 mg of nilotinib) in the listed drug product TASIGNA®.

In a cross-over design dog study, Formulations 3a and 3b are particularly noteworthy for two reasons. First, the doses of Formulations 3a and 3b are roughly one quarter the dose of the listed drug product TASIGNA®, yet the bioavailability results are comparable. Second, no unmodified organic acid is used in the Formulation 3a or 3b, thus precluding the formation of a toxic impurity that forms during storage (see Example 5 below). In addition, the $C_{max}$ and AUC results for Formulation 3a are observed to be slightly superior to the results for Formulation 3b.

TABLE 35

| Formulation | Nilotinib equivalent | $T_{max}$ (hrs) | $C_{max}$ (ng/ml) | $AUC_\infty$ (ng/ml*hr) |
|---|---|---|---|---|
| 3a | 50 mg | 1.75 | 1,034.8 ± 607.1 | 4,799 ± 3,104 |
| 3b | 50 mg | 1.5 | 775.5 ± 266.0 | 3,029 ± 1,205 |
| TASIGNA | 200 mg | 2 | 929.0 ± 840.4 | 4,739 ± 5,125 |

Comparison of Bioavailability of ASD Formulations in Fed and Fasted Dogs

Beagle dogs, (3 male and 3 female), were randomly divided into three groups. The three-period cross-over experiment design was adopted. The dogs were fasted for 12 hours before the experiment. Group 1 was administered with Formulation 3a in the fasted condition. Group 2 was administered with Formulation 3a in the fed condition. For the fed condition, dogs were fed with dog food (Shoobree, China) mixed with butter (Anchor, New Zealand) in a ratio of 100 g: 16.4 g with 500 calories. Group 3 was administered TASIGNA® under the fasted conditions. Test formulations were orally administered to each dog with 50 mL of water at the time of the administration. Blood samples were collected at 0.25, 0.5, 1, 1.5, 2, 3, 4, 8, 12, 24 hours after administration and the concentrations of nilotinib in plasma were determined. From these measurements, the parameters of $C_{max}$, $T_{max}$ and AUC were calculated and are presented in Table 36 below.

One limitation of the commercialized drug product TASIGNA® is the requirement to be administered under fasted conditions. Groups 1 and 2 show a similar $C_{max}$ and AUC in both the fed and fasted states. Formulation 3a shows an improvement over the current technology by eliminating the requirement of administration in the fasted state only. The bioavailability is higher that the commercialized product administered to Group 3, despite the dose of Formulation 3a being one quarter of the commercialized drug product.

TABLE 36

| Group | Nilotinib equivalent | Formulation and Test Condition | $T_{max}$ (hrs) | $C_{max}$ (ng/ml) | $AUC_\infty$ (ng/ml*hr) |
|---|---|---|---|---|---|
| 1 | 50 mg | Formulation 3a with fasted condition | 1.75 | 1,115.7 ± 540.6 | 4,453 ± 2,581 |
| 2 | 50 mg | Formulation 3a with fed condition | 1 | 1,034.4 ± 402.0 | 3,929 ± 2,458 |
| 3 | 200 mg | TASIGNA with fasted condition | 1.5 | 994.0 ± 573.6 | 4,654 ± 3,637 |

Oral absorption of Formulation 4 in dogs was investigated in fasted/fed conditions. Beagle dogs, (3 male and 3 female), were randomly divided into three groups. The three-period cross-over experiment design was adopted, the same as the study performed for Formulation 3a above. The pharmacokinetic parameters of $C_{max}$, $T_{max}$ and AUC were calculated and are presented in Table 37 below.

TABLE 37

| Group | Nilotinib equivalent | Formulation and Test Condition | $T_{max}$ (hrs) | $C_{max}$ (ng/ml) | $AUC_\infty$ (ng/ml*hr) |
|---|---|---|---|---|---|
| 1 | 100 mg | Formulation 4 with fasted condition | 2 | 864.0 ± 279.8 | 2,874 ± 869 |
| 2 | 100 mg | Formulation 4 with fed condition | 1.75 | 915.6 ± 425.2 | 3,360 ± 1379 |
| 3 | 200 mg | TASIGNA with fasted condition | 2 | 553.5 ± 229.1 | 1,897 ± 814 |

Formulation 4 is shown to be effective in both fed and fasted states in Table 37 above. This constitutes an improvement over the current technology by eliminating the requirement of administration in the fasted state only. Groups 1 and 2 show a similar Cmax and AUC in both the fed and fasted states. The bioavailability is higher that the commercialized product administered to Group 3, despite the lower dose of Formulation 4. Oral absorptions of tablet formulations of ASD in dogs were also evaluated with a similar study design as described for Table 36 and Table 37, with the only difference being a different food was used for the fed condition. For these studies, the dogs were fed by oral gavage of food composed of 25 grams of dog food, 150 mL of full fat milk and 60 grams of bacon.

Table 38 shows the in vivo exposures in dogs of TASIGNA® tablets under three different administration conditions. In this experiment, the dogs administered under the fasted condition are also given 6 μg/kg IM injection of pentagastrin. The exposure has three-fold increase in Cmax and four-fold increase in AUC when the product is administered after a high fat food. In addition, co-administration with an anti-acid medication (50 mg of Ranitidine per dog by IM injection) will significantly decrease the exposure.

TABLE 38

| Group | Nilotinib equivalent | Formulation and Test Condition | $T_{max}$ (hrs) | $C_{max}$ (ng/ml) | $AUC_\infty$ (ng/ml*hr) |
|---|---|---|---|---|---|
| 1 | 200 mg | TASIGNA with fasted condition | 2.0 | 888.0 ± 424.9 | 4933 ± 2488 |
| 2 | 200 mg | TASIGNA with fed condition | 6.0 | 2792 ± 841.0 | 20592 ± 9681 |
| 3 | 200 mg | TASIGNA with anti-acid medication | 3.0 | 309.7 ± 209.6 | 1941 ± 1926 |

Table 39 and Table 40 show the in vivo exposures in dogs of tablet formulations of Formulation 11a and Formulation 11b (see Table 25 for composition). Formulations 11a and 11b differ in that 11b additionally includes 100 mg of tartaric acid in the external granule materials. The results in Table 39 and Table 40 show two results. Firstly, the results suggest that the food effect has been significantly decreased and the dose could be reduced by four-fold, i.e., the in vivo exposure of the 50 mg dose of Formulation 11a and Formulation 11b is almost equivalent to 200 mg dose of TASIGNA®. Secondly, the results show that the inclusion of an additional acid in the external granulation materials increases $C_{max}$ and AUC.

TABLE 39

| Group | Nilotinib equivalent | Formulation and Test Condition | $T_{max}$ (hrs) | $C_{max}$ (ng/ml) | $AUC_\infty$ (ng/ml*hr) |
|---|---|---|---|---|---|
| 1 | 50 mg | Formulation 11a with fasted condition | 1.25 | 501.4 ± 424.7 | 1959 ± 1516 |
| 2 | 50 mg | Formulation 11a with fed condition | 4.0 | 756.2 ± 248.4 | 2980 ± 1470 |
| 3 | 200 mg | TASIGNA with fasted condition | 2.0 | 394.3 ± 423.3 | 1584 ± 1592 |

TABLE 40

| Group | Nilotinib equivalent | Formulation and Test Condition | $T_{max}$ (hrs) | $C_{max}$ (ng/ml) | $AUC_\infty$ (ng/ml*hr) |
|---|---|---|---|---|---|
| 1 | 50 mg | Formulation 11b with fasted condition | 3.0 | 960.2 ± 466.5 | 5637 ± 3102 |
| 2 | 50 mg | Formulation 11b with fed condition | 4.0 | 938.3 ± 379.6 | 6422 ± 3016 |
| 3 | 200 mg | TASIGNA with fasted condition | 3.0 | 888.3 ± 535.7 | 6530 ± 3614 |

Table 41 to Table 43 show the in vivo exposures in dogs of tablet formulations of Formulation 12 to Formulation 14 administered with and without food. The food effect is somewhat increasing as the ratio of API and surfactant components increases, but is still significantly lower than the food effect of TASIGNA®, indicating the amorphous solid dispersion formulation decreases food effect across a range of dosages.

TABLE 41

| Group | Nilotinib equivalent | Formulation and Test Condition | $T_{max}$ (hrs) | $C_{max}$ (ng/ml) | $AUC_\infty$ (ng/ml*hr) |
|---|---|---|---|---|---|
| 1 | 50 mg | Formulation 12a with fasted condition | 1.75 | 1035 ± 216.4 | 4818 ± 1619 |
| 2 | 50 mg | Formulation 12a with fed condition | 3.0 | 1026 ± 289.7 | 5948 ± 2136 |

TABLE 42

| Group | Nilotinib equivalent | Formulation and Test Condition | $T_{max}$ (hrs) | $C_{max}$ (ng/ml) | $AUC_\infty$ (ng/ml*hr) |
|---|---|---|---|---|---|
| 1 | 75 mg | Formulation 13 with fasted condition | 1.75 | 1199 ± 579.3 | 5072 ± 2799 |
| 2 | 75 mg | Formulation 13 with fed condition | 3.5 | 1359 ± 249.8 | 7851 ± 2522 |

TABLE 43

| Group | Nilotinib equivalent | Formulation and Test Condition | $T_{max}$ (hrs) | $C_{max}$ (ng/ml) | $AUC_\infty$ (ng/ml*hr) |
|---|---|---|---|---|---|
| 1 | 100 mg | Formulation 14 with fasted condition | 1.75 | 1233 ± 644.0 | 5080 ± 3594 |
| 2 | 100 mg | Formulation 14 with fed condition | 3.0 | 2801 ± 606.4 | 14800 ± 6096 |

Oral absorptions of tablet formulations of ASD in dogs were also evaluated with the similar study design as described for Table 36 and Table 37, with the only difference is that a different food was used for the fed condition. For these studies, the dogs were fed by oral gavage of the food composed of 25 grams of dog food, 150 mL of full fat milk and 60 grams of bacon.

Comparison of Bioavailability of an ASD Formulation in Fasted Dogs with Modulated Stomach pH Beagle dogs, (3 male and 3 female), were randomly divided into three groups. The three-period cross-over experiment design was adopted. The dogs were fasted for 12 hours before the experiment. All three groups were administered with Formulation 3a in the fasted condition. The test formulation was orally administered to each dog with 50 mL of water at the time of the administration. Group 1 was injected with 6 µg/kg pentapeptide gastrin into each dog's muscles 45 mins prior to oral administration. Group 2 was intravenously injected with 50 mg ranitidine 1 hour before oral administration. Group 3 was the control group. Blood samples were collected at 0.25, 0.5, 1, 1.5, 2, 3, 4, 8, 12, 24 hours after administration and the concentrations of nilotinib in plasma were determined. From these measurements, the pharmacokinetic parameters of $C_{max}$, $T_{max}$ and AUC were calculated and are presented in Table 44 below.

The study measures the efficacy of Formulation 3a in dogs with high and low stomach pH. Pentapeptide gastrin could stimulate the acid release in stomach and ranitidine could inhibit acid release in stomach. The model simulates the stomach of patients under the effect of acid reducing drugs. The commercialized product TASIGNA® is known to have reduced in-vivo absorption for patients taking anti-acid medication such as proton pump inhibitors (PPI).

Table 40). However, nilotinib HCl often yields a genotoxic impurity in the amorphous solid dispersion with acidic excipients. Under acidic conditions, nilotinib hydrolyzes to form 3-(4-methyl-TH-imidazol-1-yl)-5-(trifluoromethyl) aniline (herein after termed "impurity A") as show below.

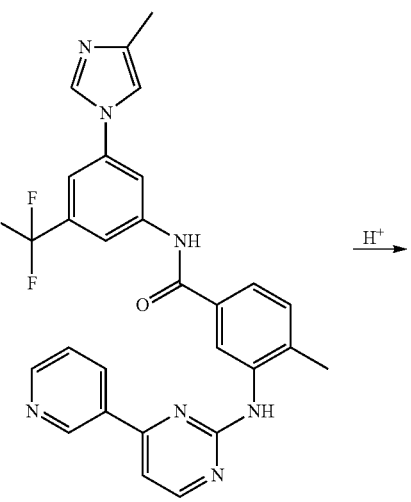

TABLE 44

| Group | Nilotinib equivalent | Formulation and Test Condition | $T_{max}$ | $C_{max}$ | $AUC_\infty$ |
|---|---|---|---|---|---|
| 1 | 50 mg | Formulation 3a with fasted condition, acidified stimulation | 1.25 | 969.1 ± 464.9 | 3,727 ± 2,989 |
| 2 | 50 mg | Formulation 3a with fasted condition, anti-acid | 2 | 592.8 ± 550.9 | 2,794 ± 3,916 |
| 3 | 50 mg | Formulation 3a with fasted condition, control | 1.5 | 708.3 ± 455.1 | 2,903 ± 3,177 |

As seen in Table 44, the pharmacokinetic parameters of $C_{max}$ and AUC between Groups 1 and 2 are only about 30% difference and the parameters have minimal difference between Groups 2 and 3, while TASIGNA® has a significant reduction of in vivo exposure after co-administration of an anti-acid medication (50 mg of Ranitidine per dog by IM injection), as shown in Table 38. These data suggest that the formulations described herein may be administered to patients taking anti-acid medication.

Example 5: Formation of Genotoxic Impurities in Amorphous Solid Dispersions of Nilotinib and Acid Formulations 2a and 2b in Example 4 show that amorphous solid dispersions of nilotinib and acidic excipient can result in vastly superior bioavailability (see Table 39 and -continued

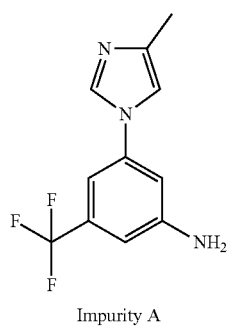

Impurity A

A degradation study was performed with amorphous solid dispersion formulations, Formulation A, Formulation B, and Formulation C, to compare the stability of different compositions. Formulation A was formulated as an amorphous solid dispersion of 55 mg nilotinib HCl, 100 mg citric acid, 100 mg lecithin, and 100 mg PVP K30. Formulation B was formulated as an amorphous solid dispersion of 55 mg nilotinib HCl, 100 mg lecithin, and 100 mg PVP K30. Formulation C was formulated as an amorphous solid dispersion of 55 mg nilotinib HCl, 75 mg citric acid, and 100 mg PVP K30. The Formulation powders were placed at 40° C./RH 75%, and 75° C./RH 75% condition for two weeks. Formulation C was formulated as an amorphous solid dispersion of 55 mg nilotinib HCl, 75 mg citric acid, and 100 mg PVP K30. The Formulation powders were placed at 40° C./RH 75%, and 75° C./RH 75% condition for two weeks. Genotoxicity impurity A was measured by a HPLC-MS method and the results are shown below in Table 45. The concentrations of genotoxic impurity A were found high for Formulation A and C, but low for Formulation B. The parameters of the degradation study were according to European Pharmacopeia 9.8; 07/2019:2993, which provides detailed parameters for evaluating the purity of a sample of nilotinib hydrochloride monohydrate.

TABLE 45

| Formulation | Compositions of ASD formulations | | | | Level of Impurity A after Storage (ppm) | | | |
|---|---|---|---|---|---|---|---|---|
| | Nilotinib HCl | PVP K30 | Lecithin | Citric acid | 40° C./RH 75%, 1 w | 40° C./RH 75%, 2 w | 75° C./RH 75%, 2 w | 75° C./RH 75%, 2 w |
| A | 55 mg | 100 mg | 100 mg | 100 mg | 16.8 | 26.8 | 275.3 | 296.6 |
| B | 55 mg | 100 mg | 100 mg | — | 1.7 | 1.2 | 4.9 | 3.0 |
| C | 55 mg | 100 mg | — | 75 mg | 31.3 | 45.7 | 171.9 | 392.2 |

In addition, tablets of Formulation 12a and Formulation 12c were packaged in HDPE bottles with 2 grams of desiccant and then stored at 40° C./75% RH for up to six months. The ASD powder of Formulation 12 (shown in Table 9) was packaged and sealed in an aluminum pouch and then also stored at the same storage condition (40° C./75% RH)

The level of Impurity A was measured by a HPLC-MS method and the results are shown below in Table 46. Note

TABLE 46

| | Level of Impurity A (ppm) during different storage time (month) | | | | |
|---|---|---|---|---|---|
| Formulation # | 0 | 1 | 2 | 3 | 6 |
| Formulation 12a | 2.9 | 3.0 | 3.3 | 4.3 | 8.0 |
| Formulation 12c | 3.3 | 3.0 | 3.8 | 3.4 | 4.1 |
| ASD of Formulation 12 | 2.1 | 2.5 | 2.8 | 3.0 | 4.0 |

Example 6: In Vivo Exposure of ASD Tablet Formulation in Humans

A tablet formulation (Formulation 11a) was tested for its in vivo exposure in humans. This study was performed by a three-way cross-over design and with 18 healthy volunteers. Formulation 11a was administered under the overnight fasting condition and after consumption of a high-fat, high-calorie food (approximately 800 to 1000 calories with 150, 250, and 500 to 600 calories from protein, carbohydrate and fat, respectively) within 30 minutes. In addition, TASIGNA® tablet formulation administered under the overnight fasting condition was also tested for comparison. Blood samples were collected at 0, 0.5, 1, 1.5, 2, 3, 4, 6, 8, 12 and 24 hours after administration and the concentrations of nilotinib in plasma were determined by a HPLC method. From these measurements, the parameters of $C_{max}$, $T_{max}$ and AUC were calculated Winnonlin 8.3.1 and are presented Table 47 below.

TABLE 47

| Group | Nilotinib equivalent | Formulation and Test Condition | $T_{max}$ (hrs) | $C_{max}$ (ng/ml) | $AUC_\infty$ (ng/ml*hr) |
|---|---|---|---|---|---|
| 1 | 50 mg | Formulation 11a with fasted condition | 1.5 | 360.6 ± 104.2 | 4060 ± 1486 |
| 2 | 50 mg | Formulation 11a with fed condition | 4.0 | 418.0 ± 64.5 | 5584 ± 1406 |
| 3 | 200 mg | TASIGNA with fasted condition | 3.5 | 427.6 ± 105.3 | 7370 ± 1928 | that the ASD of Formulation 12 has no acid component and has the lowest level of impurity A. Formulation 12c, which has the ASD of Formulation 12 and 6% surface-modified tartaric acid, has a similar level of impurity A. However, Formulation 12a, which has the component of ASD of Formulation 12 and tartaric acid without surface modification, has a significantly increased level of impurity A. This results suggest that the surface modification can reduce the formation of impurity and improve the stability of API during storage.

The results suggest that the amorphous solid dispersion technology applied in this tablet formulation has significantly reduced the food effect, in comparison to the results in Table 39. The in vivo exposure of the formulation at 50 mg strength is slightly lower than that of TASIGNA® (at 200 mg strength. However, given the results from the animal studies, Formulation 1 Ta is expected to be higher that TASIGNA® if compared at the same dose strength (200 mg). In vivo exposure in humans is also expected to increase upon the addition of acid in the external granule materials.

A tablet formulation with acid in the external granule materials (such as, for example Formulations 11b, 12a, 12b, 12c, 13, 14, 20a, 20b, 21, 22, and 23) will be tested for in vivo exposure in dogs and humans. This study will be performed by a three-way cross-over design and with healthy volunteers. The formulation will be administered under the overnight fasting condition and after consumption of a high-fat, high-calorie food (approximately 800 to 1000 calories with 150, 250, and 500 to 600 calories from protein, carbohydrate and fat, respectively) within 30 minutes. In addition, TASIGNA® tablet formulation will be administered under the overnight fasting condition for comparison. Blood samples will be collected at 0, 0.5, 1, 1.5, 2, 3, 4, 6, 8, 12 and 24 hours after administration and the concentrations of nilotinib in plasma will be determined by a HPLC method. From these measurements, the parameters of $C_{max}$, $T_{max}$ and AUC will be calculated Winnonlin 8.3.1.

Example 7: Additional Compositions

Pharmaceutical compositions comprising amorphous solid dispersions with the APIs disclosed in Table 1 are prepared and evaluated according to the procedures in Examples 1-6 by substituting the APIs used in Examples 1-6. Pharmaceutical compositions comprising an amorphous solid dispersion comprising Chlordiazepoxide are prepared and evaluated according to the procedures in Examples 1-6 by substituting the APIs used in Examples 1-6. Pharmaceutical compositions comprising an amorphous solid dispersion comprising Naringenin are prepared and evaluated according to the procedures in Examples 1-6 by substituting the APIs used in Examples 1-6. Pharmaceutical compositions comprising an amorphous solid dispersion comprising Clibric acid are prepared and evaluated according to the procedures in Examples 1-6 by substituting the APIs used in Examples 1-6. Pharmaceutical compositions comprising an amorphous solid dispersion comprising Hesperetin are prepared and evaluated according to the procedures in Examples 1-6 by substituting the APIs used in Examples 1-6. Pharmaceutical compositions comprising an amorphous solid dispersion comprising Cinchonidine are prepared and evaluated according to the procedures in Examples 1-6 by substituting the APIs used in Examples 1-6. Pharmaceutical compositions comprising an amorphous solid dispersion comprising Quinine are prepared and evaluated according to the procedures in Examples 1-6 by substituting the APIs used in Examples 1-6. Pharmaceutical compositions comprising an amorphous solid dispersion comprising Tramadol are prepared and evaluated according to the procedures in Examples 1-6 by substituting the APIs used in Examples 1-6. Pharmaceutical compositions comprising an amorphous solid dispersion comprising Lormetazepam are prepared and evaluated according to the procedures in Examples 1-6 by substituting the APIs used in Examples 1-6. Pharmaceutical compositions comprising an amorphous solid dispersion comprising Trazodone are prepared and evaluated according to the procedures in Examples 1-6 by substituting the APIs used in Examples 1-6. Pharmaceutical compositions comprising an amorphous solid dispersion comprising Diltiazem are prepared and evaluated according to the procedures in Examples 1-6 by substituting the APIs used in Examples 1-6. Pharmaceutical compositions comprising an amorphous solid dispersion comprising Brompheniramine are prepared and evaluated according to the procedures in Examples 1-6 by substituting the APIs used in Examples 1-6. Pharmaceutical compositions comprising an amorphous solid dispersion comprising Alprenolol are prepared and evaluated according to the procedures in Examples 1-6 by substituting the APIs used in Examples 1-6. Pharmaceutical compositions comprising an amorphous solid dispersion comprising Propranolol are prepared and evaluated according to the procedures in Examples 1-6 by substituting the APIs used in Examples 1-6. Pharmaceutical compositions comprising an amorphous solid dispersion comprising Diazepam are prepared and evaluated according to the procedures in Examples 1-6 by substituting the APIs used in Examples 1-6. Pharmaceutical compositions comprising an amorphous solid dispersion comprising Apigenin are prepared and evaluated according to the procedures in Examples 1-6 by substituting the APIs used in Examples 1-6. Pharmaceutical compositions comprising an amorphous solid dispersion comprising Venlafaxine are prepared and evaluated according to the procedures in Examples 1-6 by substituting the APIs used in Examples 1-6. Pharmaceutical compositions comprising an amorphous solid dispersion comprising Rosiglitazone are prepared and evaluated according to the procedures in Examples 1-6 by substituting the APIs used in Examples 1-6. Pharmaceutical compositions comprising an amorphous solid dispersion comprising Pyrilamine are prepared and evaluated according to the procedures in Examples 1-6 by substituting the APIs used in Examples 1-6. Pharmaceutical compositions comprising an amorphous solid dispersion comprising Quetiapine are prepared and evaluated according to the procedures in Examples 1-6 by substituting the APIs used in Examples 1-6. Pharmaceutical compositions comprising an amorphous solid dispersion comprising Ketopren are prepared and evaluated according to the procedures in Examples 1-6 by substituting the APIs used in Examples 1-6. Pharmaceutical compositions comprising an amorphous solid dispersion comprising Chlorphenamine are prepared and evaluated according to the procedures in Examples 1-6 by substituting the APIs used in Examples 1-6. Pharmaceutical compositions comprising an amorphous solid dispersion comprising Fenbufen are prepared and evaluated according to the procedures in Examples 1-6 by substituting the APIs used in Examples 1-6. Pharmaceutical compositions comprising an amorphous solid dispersion comprising Naproxen are prepared and evaluated according to the procedures in Examples 1-6 by substituting the APIs used in Examples 1-6. Pharmaceutical compositions comprising an amorphous solid dispersion comprising Warfarin are prepared and evaluated according to the procedures in Examples 1-6 by substituting the APIs used in Examples 1-6. Pharmaceutical compositions comprising an amorphous solid dispersion comprising Diphenhydramine are prepared and evaluated according to the procedures in Examples 1-6 by substituting the APIs used in Examples 1-6. Pharmaceutical compositions comprising an amorphous solid dispersion comprising Bupivacaine are prepared and evaluated according to the procedures in Examples 1-6 by substituting the APIs used in Examples 1-6. Pharmaceutical compositions comprising an amorphous solid dispersion comprising Clotiazepam are prepared and evaluated according to the procedures in Examples 1-6 by substituting the APIs used in Examples 1-6. Pharmaceutical compositions comprising an amorphous solid dispersion comprising Chrysin are prepared and evaluated according to the procedures in Examples 1-6 by substituting the APIs used in Examples 1-6. Pharmaceutical compositions comprising an amorphous solid dispersion comprising Valsartan are prepared and evaluated according to the procedures in Examples 1-6 by substituting the APIs used in Examples 1-6. Pharmaceutical compositions comprising an amorphous solid dispersion comprising Haloperidol are prepared and evaluated according to the procedures in Examples 1-6 by substituting the APIs used in Examples 1-6. Pharmaceutical compositions comprising an amorphous solid dispersion comprising Flurbipren are prepared and evaluated according to the procedures in Examples 1-6 by substituting the APIs used in Examples 1-6. Pharmaceutical compositions comprising an amorphous solid dispersion comprising Progesterone are prepared and evaluated according to the procedures in Examples 1-6 by substituting the APIs used in Examples 1-6. Pharmaceutical compositions comprising an amorphous solid dispersion comprising Celecoxib are prepared and evaluated according to the procedures in Examples 1-6 by substituting the APIs used in Examples 1-6. Pharmaceutical compositions comprising an amorphous solid dispersion comprising Flurazepam are prepared and evaluated according to the procedures in Examples 1-6 by substituting the APIs used in Examples 1-6. Pharmaceutical compositions comprising an amorphous solid dispersion comprising Glimepiride are prepared and evaluated according to the procedures in Examples 1-6 by substituting the APIs used in Examples 1-6. Pharmaceutical compositions comprising an amorphous solid dispersion comprising Ibupren are prepared and evaluated according to the procedures in Examples 1-6 by substituting the APIs used in Examples 1-6. Pharmaceutical compositions comprising an amorphous solid dispersion comprising Atorvastatin are prepared and evaluated according to the procedures in Examples 1-6 by substituting the APIs used in Examples 1-6. Pharmaceutical compositions comprising an amorphous solid dispersion comprising Indometacin are prepared and evaluated according to the procedures in Examples 1-6 by substituting the APIs used in Examples 1-6. Pharmaceutical compositions comprising an amorphous solid dispersion comprising Nortriptyline are prepared and evaluated according to the procedures in Examples 1-6 by substituting the APIs used in Examples 1-6. Pharmaceutical compositions comprising an amorphous solid dispersion comprising Loratadine are prepared and evaluated according to the procedures in Examples 1-6 by substituting the APIs used in Examples 1-6. Pharmaceutical compositions comprising an amorphous solid dispersion comprising Fluoxetine are prepared and evaluated according to the procedures in Examples 1-6 by substituting the APIs used in Examples 1-6. Pharmaceutical compositions comprising an amorphous solid dispersion comprising Diclenac are prepared and evaluated according to the procedures in Examples 1-6 by substituting the APIs used in Examples 1-6. Pharmaceutical compositions comprising an amorphous solid dispersion comprising Clopidogrel are prepared and evaluated according to the procedures in Examples 1-6 by substituting the APIs used in Examples 1-6. Pharmaceutical compositions comprising an amorphous solid dispersion comprising Duloxetine are prepared and evaluated according to the procedures in Examples 1-6 by substituting the APIs used in Examples 1-6. Pharmaceutical compositions comprising an amorphous solid dispersion comprising Penbutolol are prepared and evaluated according to the procedures in Examples 1-6 by substituting the APIs used in Examples 1-6. Pharmaceutical compositions comprising an amorphous solid dispersion comprising Maprotiline are prepared and evaluated according to the procedures in Examples 1-6 by substituting the APIs used in Examples 1-6. Pharmaceutical compositions comprising an amorphous solid dispersion comprising Imipramine are prepared and evaluated according to the procedures in Examples 1-6 by substituting the APIs used in Examples 1-6. Pharmaceutical compositions comprising an amorphous solid dispersion comprising Amitriptyline are prepared and evaluated according to the procedures in Examples 1-6 by substituting the APIs used in Examples 1-6. Pharmaceutical compositions comprising an amorphous solid dispersion comprising Cyproheptadine are prepared and evaluated according to the procedures in Examples 1-6 by substituting the APIs used in Examples 1-6. Pharmaceutical compositions comprising an amorphous solid dispersion comprising Sertraline are prepared and evaluated according to the procedures in Examples 1-6 by substituting the APIs used in Examples 1-6. Pharmaceutical compositions comprising an amorphous solid dispersion comprising Flufenamic acid are prepared and evaluated according to the procedures in Examples 1-6 by substituting the APIs used in Examples 1-6. Pharmaceutical compositions comprising an amorphous solid dispersion comprising Chlorpromazine are prepared and evaluated according to the procedures in Examples 1-6 by substituting the APIs used in Examples 1-6. Pharmaceutical compositions comprising an amorphous solid dispersion comprising Miconazole are prepared and evaluated according to the procedures in Examples 1-6 by substituting the APIs used in Examples 1-6. Pharmaceutical compositions comprising an amorphous solid dispersion comprising Rimonabant are prepared and evaluated according to the procedures in Examples 1-6 by substituting the APIs used in Examples 1-6. Pharmaceutical compositions comprising an amorphous solid dispersion comprising Clofazimine are prepared and evaluated according to the procedures in Examples 1-6 by substituting the APIs used in Examples 1-6. Pharmaceutical compositions comprising an amorphous solid dispersion comprising Enzalutamide are prepared and evaluated according to the procedures in Examples 1-6 by substituting the APIs used in Examples 1-6. Pharmaceutical compositions comprising an amorphous solid dispersion comprising lapatinib are prepared and evaluated according to the procedures in Examples 1-6 by substituting the APIs used in Examples 1-6. Pharmaceutical compositions comprising an amorphous solid dispersion comprising pazopanib are prepared and evaluated according to the procedures in Examples 1-6 by substituting the APIs used in Examples 1-6. Pharmaceutical compositions comprising an amorphous solid dispersion comprising erlotinib are prepared and evaluated according to the procedures in Examples 1-6 by substituting the APIs used in Examples 1-6. Pharmaceutical compositions comprising an amorphous solid dispersion comprising dasatinib are prepared and evaluated according to the procedures in Examples 1-6 by substituting the APIs used in Examples 1-6. Pharmaceutical compositions comprising an amorphous solid dispersion comprising gefitinib are prepared and evaluated according to the procedures in Examples 1-6 by substituting the APIs used in Examples 1-6. Pharmaceutical compositions comprising an amorphous solid dispersion comprising sorafenib are prepared and evaluated according to the procedures in Examples 1-6 by substituting the APIs used in Examples 1-6. Pharmaceutical compositions comprising an amorphous solid dispersion comprising axitinib are prepared and evaluated according to the procedures in Examples 1-6 by substituting the APIs used in Examples 1-6. Pharmaceutical compositions comprising an amorphous solid dispersion comprising crizotinib are prepared and evaluated according to the procedures in Examples 1-6 by substituting the APIs used in Examples 1-6. Pharmaceutical compositions comprising an amorphous solid dispersion comprising vemurafenib are prepared and evaluated according to the procedures in Examples 1-6 by substituting the APIs used in Examples 1-6. Pharmaceutical compositions comprising an amorphous solid dispersion comprising telotristat ethyl are prepared and evaluated according to the procedures in Examples 1-6 by substituting the APIs used in Examples 1-6. Pharmaceutical compositions comprising an amorphous solid dispersion comprising ivacaftor are prepared and evaluated according to the procedures in Examples 1-6 by substituting the APIs used in Examples 1-6. Pharmaceutical compositions comprising an amorphous solid dispersion comprising nintedanib are prepared and evaluated according to the procedures in Examples 1-6 by substituting the APIs used in Examples 1-6. Pharmaceutical compositions comprising an amorphous solid dispersion comprising Ibrutinib are prepared and evaluated according to the procedures in Examples 1-6 by substituting the APIs used in Examples 1-6. Pharmaceutical compositions comprising an amorphous solid dispersion comprising alectinib are prepared and evaluated according to the procedures in Examples 1-6 by substituting the APIs used in Examples 1-6. Pharmaceutical compositions comprising an amorphous solid dispersion comprising bosutinib are prepared and evaluated according to the procedures in Examples 1-6 by substituting the APIs used in Examples 1-6. Pharmaceutical compositions comprising an amorphous solid dispersion comprising lenvatinib are prepared and evaluated according to the procedures in Examples 1-6 by substituting the APIs used in Examples 1-6. Pharmaceutical compositions comprising an amorphous solid dispersion comprising midostaurin are prepared and evaluated according to the procedures in Examples 1-6 by substituting the APIs used in Examples 1-6. Pharmaceutical compositions comprising an amorphous solid dispersion comprising ribociclib are prepared and evaluated according to the procedures in Examples 1-6 by substituting the APIs used in Examples 1-6. Pharmaceutical compositions comprising an amorphous solid dispersion comprising avapritinib are prepared and evaluated according to the procedures in Examples 1-6 by substituting the APIs used in Examples 1-6. Pharmaceutical compositions comprising an amorphous solid dispersion comprising pexidartinib are prepared and evaluated according to the procedures in Examples 1-6 by substituting the APIs used in Examples 1-6. Pharmaceutical compositions comprising an amorphous solid dispersion comprising neratinib are prepared and evaluated according to the procedures in Examples 1-6 by substituting the APIs used in Examples 1-6. Pharmaceutical compositions comprising an amorphous solid dispersion comprising enzalutamide are prepared and evaluated according to the procedures in Examples 1-6 by substituting the APIs used in Examples 1-6. Pharmaceutical compositions comprising an amorphous solid dispersion comprising lurasidone are prepared and evaluated according to the procedures in Examples 1-6 by substituting the APIs used in Examples 1-6. Pharmaceutical compositions comprising an amorphous solid dispersion comprising vilazodone are prepared and evaluated according to the procedures in Examples 1-6 by substituting the APIs used in Examples 1-6. Pharmaceutical compositions comprising an amorphous solid dispersion comprising entrectinib are prepared and evaluated according to the procedures in Examples 1-6 by substituting the APIs used in Examples 1-6.

It should be appreciated that there is considerable overlap between the above listed components in common usage, since a given component is often classified differently by different practitioners in the field, or is commonly used for any of several different functions, or may have differing functions depending on the levels in the composition. Thus, the above-listed components should be taken as merely exemplary, and not limiting, of the types of components that can be included in compositions of the present invention.

Additional Embodiments

Disclosed herein is an amorphous solid dispersion, wherein the amorphous solid dispersion comprises: a) a lipophilic active pharmaceutical ingredient or a pharmaceutically acceptable salt thereof, wherein the active pharmaceutical ingredient has a log P in octanol-water equal or greater than 2.0; b) a surfactant, wherein the surfactant is selected from polymeric non-ionic surfactants and phospholipids; c) a non-ionic hydrophilic polymer; and d) optionally an adsorbent. In some embodiments, the active pharmaceutical ingredient or a pharmaceutically acceptable salt thereof is selected from nilotinib, abiraterone acetate, celecoxib, flurazepam, atorvastatin, indometacin, nortriptyline, loratadine, fluoxetine, diclofenac, clopidogrel, duloxetine, maprotiline, imipramine, amitriptyline, cyproheptadine, sertraline, flufenamic acid, chlorpromazine, miconazole, rimonabant, clofazimine, enzalutamide, lapatinib, pazopanib, erlotinib, dasatinib, gefitinib, sorafenib, axitinib, crizotinib, vemurafenib, telotristat ethyl, ivacaftor, nintedanib, ibrutinib, alectinib, bosutinib, lenvatinib, midostaurin, avapritinib, pexidartinib, alectinib, neratinib, enzalutamide, the corresponding free base thereof and pharmaceutically acceptable salts thereof. In some embodiments, the active pharmaceutical ingredient or a pharmaceutically acceptable salt thereof is present in the amorphous solid dispersion in an amount of about 5 wt % to about 70 wt % based on solids. In some embodiments, the surfactant is a polymeric non-ionic surfactant. In some embodiments, the polymeric non-ionic surfactant comprises a block copolymer of polyethylene glycol and polypropylene glycol. In some embodiments, the polymeric non-ionic surfactant is Poloxamer 188. In some embodiments, the surfactant comprises one or more phospholipids. In some embodiments, the surfactant comprises one or more of phosphatidylcholine, phosphatidylethanolamine, phosphatidylinositol, phosphatidylserine, plasmalogen, sphingomyelin, and phosphatidic acid. In some embodiments, the surfactant comprises lecithin. In some embodiments, the surfactant is present in the amorphous solid dispersion in an amount of about 5 wt % to about 70 wt % based on solids. In some embodiments, a weight ratio of the active pharmaceutical ingredient or a pharmaceutically acceptable salt thereof to the surfactant is from about 10:1 to about 1:10. In some embodiments, the non-ionic hydrophilic polymer comprises polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-n-CD), hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof. In some embodiments, the non-ionic hydrophilic polymer is HPMC, PVP, HP-3-CD, PVA, HPMCAS, or PCL-PVAc-PEG. In some embodiments, the non-ionic hydrophilic polymer is present in the amorphous solid dispersion in an amount of about 5 wt % to about 70 wt % based on solids. In some embodiments, a weight ratio of the active pharmaceutical ingredient or a pharmaceutically acceptable salt thereof to the non-ionic hydrophilic polymer is from about 10:1 to about 1:10. In some embodiments, the adsorbent is selected from silicon dioxide, active carbon, magnesium aluminum silicate, diatomite, microcrystalline cellulose (MCC), silicified microcrystalline cellulose (SMCC), talc, crosslinked povidone, sodium carboxymethylcellulose, sodium carboxymethyl starch, and also sugars or sugar alcohols such as sorbitol, mannitol, lactose, cyclodextrin, and maltodextrin. In some embodiments, the adsorbent is silicon dioxide. In some embodiments, the adsorbent is present in the amorphous solid dispersion in an amount of about 10 to about 35% wt. In some embodiments, the average particle diameter of the amorphous solid dispersion is from 1 µm to 1000 µm. In some embodiments, an average particle size of the amorphous solid dispersion, in terms of particle diameter, is from about 10 µm to about 150 µm. In some embodiments, the amorphous solid dispersion additionally comprises an inorganic acid or organic acid. In some embodiments, the organic acid is selected from the group consisting of tartaric acid, fumaric acid, succinic acid, citric acid, lactic acid, malic acid, methanesulfonic acid, ethanesulfonic acid, isethionic acid, benzenesulfonic acid, p-toluenesulfonic acid, In some embodiments, the inorganic acid is selected from the group consisting of hydrochloric acid, sulfuric acid, and phosphoric acid. In some embodiments, the API is an API of Table 1 or a pharmaceutically acceptable salt thereof.

Disclosed herein is a pharmaceutical composition, wherein the pharmaceutical composition comprises: a) an amorphous solid dispersion that comprises: i. an active pharmaceutical ingredient or a pharmaceutically acceptable salt thereof, wherein the active pharmaceutical ingredient has a log P in octanol-water equal or greater than 2.0; ii. a surfactant, wherein the surfactant is selected from polymeric non-ionic surfactants and phospholipids; iii. a non-ionic hydrophilic polymer; and iv. optionally adsorbent, b) a pharmaceutically acceptable carrier or excipient. In some embodiments, the pharmaceutical composition is in a form of a tablet or capsule. In some embodiments, the active pharmaceutical ingredient or a pharmaceutically acceptable salt thereof is selected from nilotinib, abiraterone acetate, celecoxib, flurazepam, atorvastatin, indometacin, nortriptyline, loratadine, fluoxetine, diclofenac, clopidogrel, duloxetine, maprotiline, imipramine, amitriptyline, cyproheptadine, sertraline, flufenamic acid, chlorpromazine, miconazole, rimonabant, clofazimine, enzalutamide, lapatinib, pazopanib, erlotinib, dasatinib, gefitinib, sorafenib, axitinib, crizotinib, vemurafenib, telotristat ethyl, ivacaftor, nintedanib, ibrutinib, alectinib, bosutinib, lenvatinib, midostaurin, avapritinib, pexidartinib, alectinib, neratinib, enzalutamide, the corresponding free base thereof and pharmaceutically acceptable salts thereof. In some embodiments, the active pharmaceutical ingredient has a log P in octanol-water equal or greater than 3.0. In some embodiments, the active pharmaceutical ingredient or a pharmaceutically acceptable salt thereof is present in the pharmaceutical composition of a unit dosage form in an amount of about 10 mg to about 500 mg. In some embodiments, the surfactant is present in the pharmaceutical composition of a unit dosage form in an amount of about 10 mg to about 500 mg. In some embodiments, the non-ionic hydrophilic polymer is polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-Q-CD), hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof. In some embodiments, the non-ionic hydrophilic polymer is present in the pharmaceutical composition in an amount of about 10 mg to about 500 mg. In some embodiments, the silicon dioxide is present in the amorphous solid dispersion in an amount of about 10 to about 35% wt. In some embodiments, the average diameter of the amorphous solid dispersion is from 1 µm to 1000 µm. In some embodiments, the pharmaceutical composition exhibits a bioavailability that is at least 2-fold higher than a bioavailability of a corresponding formulation comprising the active pharmaceutical ingredient or a pharmaceutically acceptable salt thereof in a crystalline form, when measured as the total area under the curve (AUC) after oral administration or when measured as Cmax after oral administration. In some embodiments, the pharmaceutical composition exhibits a bioavailability that is at least 2-fold higher than a bioavailability of a reference pharmaceutical composition that comprises the active pharmaceutical ingredient or a pharmaceutically acceptable salt thereof, when measured as the total area under the curve (AUC) after oral administration or when measured as Cmax after oral administration, wherein the reference pharmaceutical composition does not comprise an amorphous solid dispersion. In some embodiments, the bioavailability is measured in a dog model in a fasted state or in a fed state. In some embodiments, a bioavailability of the pharmaceutical composition does not vary for more than 50% when orally administered in a fed state compared to a bioavailability administered in a fasted state, when measured as the total area under the curve (AUC) after oral administration or when measured as Cmax after oral administration. In some embodiments, the amorphous solid dispersion additionally comprises an inorganic acid or organic acid. In some embodiments, the organic acid is selected from the group consisting of tartaric acid, fumaric acid, succinic acid, citric acid, lactic acid, malic acid, methanesulfonic acid, ethanesulfonic acid, isethionic acid, benzenesulfonic acid, p-toluenesulfonic acid, In some embodiments, the inorganic acid is selected from the group consisting of hydrochloric acid, sulfuric acid, and phosphoric acid. In some embodiments, the adsorbent is selected from silicon dioxide, active carbon, magnesium aluminum silicate, diatomite, microcrystalline cellulose (MCC), silicified microcrystalline cellulose (SMCC), talc, crosslinked povidone, sodium carboxymethylcellulose, sodium carboxymethyl starch, and also sugars or sugar alcohols such as sorbitol, mannitol, lactose, cyclodextrin, and maltodextrin. In some embodiments, the adsorbent is silicon dioxide.

Disclosed herein is an amorphous solid dispersion, wherein the amorphous solid dispersion comprises:
i. a compound of Formula (I), or a N-oxide or a pharmaceutically acceptable salt thereof,

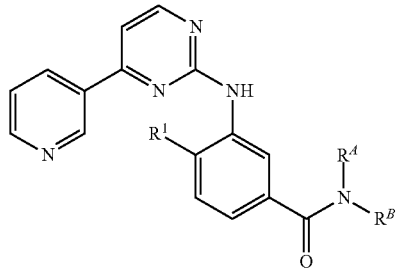

Formula (I)

wherein
R$^1$ is hydrogen, C$_1$-C$_6$ alkyl, or halogen;
R$^A$ is hydrogen, C$_1$-C$_6$ alkyl, C$_{1-6}$ alkoxy-C$_{1-6}$ alkyl, acyloxy-C$_{1-6}$ alkyl, carboxy-C$_{1-6}$ alkyl, C$_{1-6}$ alkoxycarbonyl-C$_{1-6}$ alkyl, or phenyl-C$_{1-6}$ alkyl,
R$^B$ is hydrogen, C$_1$-C$_6$ alkyl, optionally and independently substituted by one or more R$^{10}$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or poly-substituted, wherein
R$^{10}$ represents hydroxy, C$_1$-C$_6$ alkoxy, acyloxy, carboxy, C$_{1-6}$ alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted; or
R$^A$ and R$^B$ taken together form a C$_4$-C$_6$ alkylene optionally mono- or disubstituted by C$_1$-C$_6$ alkyl, cycloalkyl, heterocyclyl, phenyl, hydroxy, C$_1$-C$_6$ alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by C$_1$-C$_6$ alkyl, phenyl-C$_1$-C$_6$ alkyl, C$_{1-6}$ alkoxycarbonyl-C$_{1-6}$ alkyl, carboxy-C$_{1-6}$ alkyl, carbamoyl-C$_{1-6}$ alkyl, N-mono- or N,N-disubstituted carbamoyl-C$_{1-6}$ alkyl, cycloalkyl, C$_{1-6}$ alkoxycarbonyl, carboxy, phenyl, substituted phenyl, pyridinyl, pyrimidinyl, or pyrazinyl;
ii. a surfactant, wherein the surfactant is selected from polymeric non-ionic surfactants and phospholipids; and
iii. a non-ionic hydrophilic polymer; and
iv. optionally an adsorbent.

In some embodiments, the amorphous solid dispersion comprises:
a compound of Formula (I), or a N-oxide or a pharmaceutically acceptable salt thereof, wherein:
R$^1$ is hydrogen, C$_1$-C$_6$ alkyl, or halogen;
R$^A$ is hydrogen, C$_1$-C$_6$ alkyl, C$_{1-6}$ alkoxy-C$_{1-6}$ alkyl, or benzyl;

R$^B$ is phenyl substituted by one or two substituents selected from the group consisting of C$_1$-C$_6$ alkyl, trifluoro-C$_{1-6}$ alkyl, hydroxy-C$_{1-6}$ alkyl, amino-C$_{1-6}$ alkyl, C$_{1-6}$ alkylamino-C$_{1-6}$ alkyl, di-C$_{1-6}$ alkylamino-C$_{1-6}$ alkyl, N-cyclohexyl-N-$_1$-6 alkylamino-C$_{1-6}$ alkyl, C$_{1-6}$ alkoxycarbonylpiperidino-C$_{1-6}$ alkyl, N—C$_{1-6}$ alkylpiperazino-C$_{1-6}$ alkyl, C$_{1-6}$ alkoxycarbonyl-C$_{1-6}$ alkyl, hydroxy, C$_1$-C$_6$ alkoxy, trifluoro-C$_{1-6}$ alkoxy, 1H-imidazolyl-C$_{1-6}$ alkoxy, C$_{1-6}$ alkanoyloxy, benzoyloxy, carboxy, C$_{1-6}$ alkoxycarbonyl, carbamoyl, C$_{1-6}$ alkylcarbamoyl, amino, C$_{1-6}$ alkanoylamino, benzoylamino, amino mono- or disubstituted by C$_1$-C$_6$ alkyl, by hydroxy-C$_{1-6}$ alkyl or by C$_{1-6}$ alkoxy-C$_{1-6}$ alkyl, 1H-imidazolyl, C$_{1-6}$ alkyl-1H-imidazolyl, carboxy-1H-imidazolyl, C$_{1-6}$ alkylestercarboxy-1H-imidazolyl, pyrrolidino, piperidino, piperazino, N—C$_{1-6}$ alkylpiperazino, morpholino, sulfamoyl, C$_{1-6}$ alkylsulfonyl, phenyl, pyridyl, halogenyl, or benzoyl.

In some embodiments, the amorphous solid dispersion comprises:
a compound of Formula (I), or a N-oxide or a pharmaceutically acceptable salt thereof, wherein:
R$^1$ is methyl;
R$^A$ is hydrogen;
R$^B$ is phenyl substituted by trifluoremethyl and optionally a further substituent selected from the group consisting of hydroxy-C$_{1-6}$ alkyl, C$_{1-6}$ alkylamino, hydroxy-C$_{1-6}$ alkylamino, di-C$_{1-6}$ alkylamino, 1H-imidazolyl, C$_{1-6}$ alkyl-1H-imidazolyl, carbamoyl, C$_{1-6}$ alkylcarbamoyl, pyrrolidino, piperidino, piperazino, C$_{1-6}$ alkylpiperazino, morpholino, C$_1$-C$_6$ alkoxy, trifluoro-C$_{1-6}$ alkoxy, phenyl, pyridyl, and halogenyl.

In some embodiments, the amorphous solid dispersion comprises: a compound of Formula (I), or a N-oxide or a pharmaceutically acceptable salt thereof, wherein:
R$^1$ is methyl;
R$^A$ is hydrogen;
R$^B$ is phenyl substituted by 5-trifluoromethyl and optionally a further substituent selected from the group consisting of 2-methyl-1H-imidazolyl, 4-methyl-1H-imidazolyl, 2,4-dimethyl-1H-imidazolyl, 5-methyl-1H imidazolyl, 2-methoxymethylamino, propoxy, ethoxy, methylaminocarbonyl, benzoyl, 4-methoxy-2-methyl, acetylamino 2,4-dimethyl-1H-imidazolyl, acetic acid ethyl ester, piperidine carboxylic acid ethyl ester.

In some embodiments, compound of Formula (I), or a N-oxide or a pharmaceutically acceptable salt thereof is present in the pharmaceutical composition in an amount of about 10 mg to about 500 mg. In some embodiments, the surfactant is Poloxamer 188 or lecithin. In some embodiments, the surfactant is present in the pharmaceutical composition in an amount of about 10 mg to about 500 mg. In some embodiments, the non-ionic hydrophilic polymer is polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-n-CD), hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof. In some embodiments, the non-ionic hydrophilic polymer is present in the pharmaceutical composition in an amount of about 10 mg to about 500 mg. In some embodiments, the amorphous solid dispersion comprises silicon dioxide powder in an amount of about 10 to about 35% wt. In some embodiments, the compound of Formula (I), or a N-oxide or a pharmaceutically acceptable salt thereof is nilotinib, or a pharmaceutical acceptable salt thereof. In some embodiments, the compound of Formula (I), or a N-oxide or a pharmaceutically acceptable salt thereof is nilotinib hydrochloride.

In some embodiments, the pharmaceutical composition comprises:
  b) an amorphous solid dispersion that comprises:
    i. a compound of Formula (I), or a N-oxide or a pharmaceutically acceptable salt thereof,

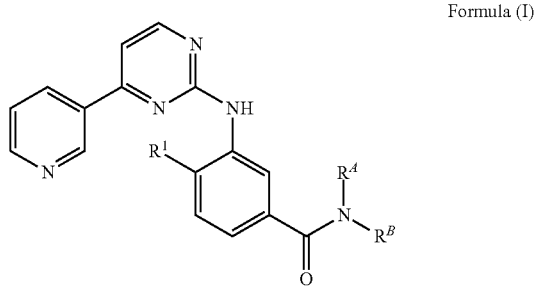

Formula (I)

wherein
  $R^1$ is hydrogen, $C_1$-$C_6$ alkyl, or halogen;
  $R^A$ is hydrogen, $C_1$-$C_6$ alkyl, $C_{1-6}$ alkoxy-$C_{1-6}$ alkyl, acyloxy-$C_{1-6}$ alkyl, carboxy-$C_{1-6}$ alkyl, $C_{1-6}$ alkoxycarbonyl-$C_{1-6}$ alkyl, or phenyl-$C_{1-6}$ alkyl,
  $R^B$ is hydrogen, $C_1$-$C_6$ alkyl, optionally and independently substituted by one or more $R^{10}$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or poly-substituted, wherein
    $R^{10}$ represents hydroxy, $C_1$-$C_6$ alkoxy, acyloxy, carboxy, $C_{1-6}$ alkoxycarbonyl, carbamoyl, N-mono- or N,N-disubstituted carbamoyl, amino, mono- or dis-ubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted; or
  $R^A$ and $R^B$ taken together form a $C_4$-$C_6$ alkylene optionally mono- or disubstituted by $C_1$-$C_6$ alkyl, cycloalkyl, heterocyclyl, phenyl, hydroxy, $C_1$-$C_6$ alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by $C_1$-$C_6$ alkyl, phenyl-$C_1$-$C_6$ alkyl, $C_{1-6}$ alkoxycarbonyl-$C_{1-6}$ alkyl, carboxy-$C_{1-6}$ alkyl, carbamoyl-$C_{1-6}$ alkyl, N-mono- or N,N-disubstituted carbamoyl-$C_{1-6}$ alkyl, cycloalkyl, $C_{1-6}$ alkoxycarbonyl, carboxy, phenyl, substituted phenyl, pyridinyl, pyrimidinyl, or pyrazinyl;
    ii. a surfactant, wherein the surfactant is selected from polymeric non-ionic surfactants and phospholipids;
    iii. a non-ionic hydrophilic polymer; and
    iv. optionally an adsorbent, and
  c) a pharmaceutically acceptable carrier or excipient.

In some embodiments, the pharmaceutical composition comprises an amorphous solid dispersion that comprises:
  $R^1$ is hydrogen, $C_1$-$C_6$ alkyl, or halogen;
  $R^A$ is hydrogen, $C_1$-$C_6$ alkyl, $C_{1-6}$ alkoxy-$C_{1-6}$ alkyl, or benzyl;
  $R^B$ is phenyl substituted by one or two substituents selected from the group consisting of $C_1$-$C_6$ alkyl, trifluoro-$C_{1-6}$ alkyl, hydroxy-$C_{1-6}$ alkyl, amino-$C_{1-6}$ alkyl, $C_{1-6}$ alkylamino-$C_{1-6}$ alkyl, di-$C_{1-6}$ alkylamino-$C_{1-6}$ alkyl, N-cyclohexyl-N-$_1$-6 alkylamino-$C_{1-6}$ alkyl, $C_{1-6}$ alkoxycarbonylpiperidino-$C_{1-6}$ alkyl, N—$C_{1-6}$ alkylpiperazino-$C_{1-6}$ alkyl, $C_{1-6}$ alkoxycarbonyl-$C_{1-6}$ alkyl, hydroxy, $C_1$-$C_6$ alkoxy, trifluoro-$C_{1-6}$ alkoxy, 1H-imidazolyl-$C_{1-6}$ alkoxy, $C_{1-6}$ alkanoyloxy, benzoyloxy, carboxy, $C_{1-6}$ alkoxycarbonyl, carbamoyl, $C_{1-6}$ alkylcarbamoyl, amino, $C_{1-6}$ alkanoylamino, benzoylamino, amino mono- or di-substituted by $C_1$-$C_6$ alkyl, by hydroxy-$C_{1-6}$ alkyl or by $C_{1-6}$ alkoxy-$C_{1-6}$ alkyl, 1H-imidazolyl, $C_{1-6}$ alkyl-TH-imidazolyl, carboxy-1H-imidazolyl, $C_{1-6}$ alkyl-estercarboxy-1H-imidazolyl, pyrrolidino, piperidino, piperazino, N—$C_{1-6}$ alkylpiperazino, morpholino, sulfamoyl, $C_{1-6}$ alkylsulfonyl, phenyl, pyridyl, halogenyl, or benzoyl.

In some embodiments, the pharmaceutical composition comprises an amorphous solid dispersion that comprises:
  $R^1$ is methyl;
  $R^A$ is hydrogen;
  $R^B$ is phenyl substituted by trifluoromethyl and optionally a further substituent selected from the group consisting of hydroxy-$C_{1-6}$ alkyl, $C_{1-6}$ alkylamino, hydroxy-$C_{1-6}$ alkylamino, di-$C_{1-6}$ alkylamino, 1H-imidazolyl, $C_{1-6}$ alkyl-1H-imidazolyl, carbamoyl, $C_{1-6}$ alkylcarbamoyl, pyrrolidino, piperidino, piperazino, $C_{1-6}$ alkylpiperazino, morpholino, $C_1$-$C_6$ alkoxy, trifluoro-$C_{1-6}$ alkoxy, phenyl, pyridyl, and halogenyl.

In some embodiments, the pharmaceutical composition comprises an amorphous solid dispersion that comprises:
  $R^1$ is methyl;
  $R^A$ is hydrogen;
  $R^B$ is phenyl substituted by 5-trifluoromethyl and optionally a further substituent selected from the group consisting of 2-methyl-1H-imidazolyl, 4-methyl-TH-imidazolyl, 2,4-dimethyl-1H-imidazolyl, 5-methyl-1H imidazolyl, 2-methoxymethylamino, propoxy, ethoxy, methylaminocarbonyl, benzoyl, 4-methoxy-2-methyl, acetylamino 2,4-dimethyl-1H-imidazolyl, acetic acid ethyl ester, piperidine carboxylic acid ethyl ester.

In some embodiments, the compound of Formula (I), or a N-oxide or a pharmaceutically acceptable salt thereof is present in the pharmaceutical composition in an amount of about 10 mg to about 500 mg. In some embodiments, the surfactant is Poloxamer 188 or lecithin. In some embodiments, the surfactant is present in the pharmaceutical composition in an amount of about 10 mg to about 500 mg. In some embodiments, the non-ionic hydrophilic polymer is polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-β-CD), hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL- PVAc-PEG), or a combination thereof. In some embodiments, the non-ionic hydrophilic polymer is present in the pharmaceutical composition in an amount of about 10 mg to about 500 mg. In some embodiments, the amorphous solid dispersion comprises silicon dioxide powder in an amount of about 10 to about 35% wt. In some embodiments, the compound of Formula (I), or a N-oxide or a pharmaceutically acceptable salt thereof is nilotinib hydrochloride. In some embodiments, the pharmaceutical composition exhibits a bioavailability that is at least 2-fold higher than a bioavailability of a corresponding formulation comprising crystalline nilotinib hydrochloride, when measured as the total area under the curve (AUC) after oral administration or when measured as Cmax after oral administration. In some embodiments, the pharmaceutical composition exhibits a bioavailability that is at least 2-fold higher than a bioavailability of a reference pharmaceutical composition that comprises nilotinib hydrochloride, when measured as the total area under the curve (AUC) after oral administration or when measured as Cmax after oral administration, wherein the reference pharmaceutical composition does not comprise an amorphous solid dispersion. In some embodiments, the bioavailability is measured in a dog model in a fasted state or in a fed state.

Disclosed herein is an amorphous solid dispersion, wherein the amorphous solid dispersion comprises: a) nilotinib free base or a pharmaceutically acceptable salt thereof; b) a surfactant that is lecithin; c) a non-ionic hydrophilic polymer; and d) optionally an adsorbent. In some embodiments, the nilotinib free base or a pharmaceutically acceptable salt thereof is a salt of nilotinib. In some embodiments, the salt of nilotinib is selected from nilotinib hydrochloride, nilotinib sulfate, nilotinib fumarate, nilotinib 2-chloromandelate, nilotinib succinate, nilotinib adipate, nilotinib 1-tartrate, nilotinib glutarate, nilotinib p-toluenesulfonate, nilotinib camphorsulfonate, nilotinib glutamate, nilotinib palmitate, nilotinib quinate, nilotinib citrate, nilotinib maleate, nilotinib acetate, nilotinib 1-malate, nilotinib 1-aspartate, nilotinib formate, nilotinib hydrobromide, nilotinib oxalate and nilotinib malonate. In some embodiments, the nilotinib free base or a pharmaceutically acceptable salt thereof is present in the amorphous solid dispersion in an amount of about 5 wt % to about 70 wt % based on solids. In some embodiments, the surfactant is present in the amorphous solid dispersion in an amount of about 5 wt % to about 70 wt % based on solids. In some embodiments, a weight ratio of the nilotinib free base or a pharmaceutically acceptable salt thereof to the surfactant is from about 10:1 to about 1:10. In some embodiments, the non-ionic hydrophilic polymer comprises polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-β-CD), hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof. In some embodiments, the non-ionic hydrophilic polymer is HPMC, PVP, HP-β-CD, or PVA, PCL-PVAc-PEG, or PCL-PVAc-PEG. In some embodiments, the non-ionic hydrophilic polymer is present in the amorphous solid dispersion in an amount of about 5 wt % to about 70 wt % based on solids. In some embodiments, a weight ratio of the nilotinib free base or a pharmaceutically acceptable salt thereof to the non-ionic hydrophilic polymer is from about 10:1 to about 1:10. In some embodiments, an average particle size of the amorphous solid dispersion, in terms of particle diameter, is from about 1 μm to about 150 μm.

Disclosed herein a pharmaceutical composition, wherein the pharmaceutical composition comprises: a) an amorphous solid dispersion that comprises: i. nilotinib free base or a pharmaceutically acceptable salt thereof; ii. a surfactant that is lecithin; iii. a non-ionic hydrophilic polymer; and iv. optionally silicon dioxide, and b) a pharmaceutically acceptable carrier or excipient. In some embodiments, the pharmaceutical composition is in a form of a tablet or capsule. In some embodiments, the nilotinib free base or a pharmaceutically acceptable salt thereof is a salt of nilotinib. In some embodiments, the salt of nilotinib is selected from nilotinib hydrochloride, nilotinib sulfate, nilotinib fumarate, nilotinib 2-chloromandelate, nilotinib succinate, nilotinib adipate, nilotinib 1-tartrate, nilotinib glutarate, nilotinib p-toluenesulfonate, nilotinib camphorsulfonate, nilotinib glutamate, nilotinib palmitate, nilotinib quinate, nilotinib citrate, nilotinib maleate, nilotinib acetate, nilotinib 1-malate, nilotinib 1-aspartate, nilotinib formate, nilotinib hydrobromide, nilotinib oxalate and nilotinib malonate. In some embodiments, the nilotinib free base or a pharmaceutically acceptable salt thereof is present in the pharmaceutical composition in an amount of about 10 mg to about 500 mg. In some embodiments, the surfactant is present in the pharmaceutical composition in an amount of about 10 mg to about 500 mg. In some embodiments, the non-ionic hydrophilic polymer is polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-β-CD), hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof. In some embodiments, the non-ionic hydrophilic polymer is present in the pharmaceutical composition in an amount of about 10 mg to about 500 mg. In some embodiments, the amorphous solid dispersion comprises silicon dioxide powder in an amount of about 10 to about 35% wt. In some embodiments, the pharmaceutical composition is free of organic acid. In some embodiments, the pharmaceutical composition is storage stable for at least 2 weeks at 75° C./75% RH, wherein a storage stable pharmaceutical composition has less than 100 ppm of Impurity A at the end of the storage period. In some embodiments, the pharmaceutical composition exhibits a bioavailability that is at least 2-fold higher than a bioavailability of a corresponding formulation comprising nilotinib free base or a pharmaceutically acceptable salt thereof in a crystalline form, when measured as the total area under the curve (AUC) after oral administration or when measured as Cmax after oral administration. In some embodiments, the pharmaceutical composition exhibits a bioavailability that is at least 2-fold higher than a bioavailability of a reference pharmaceutical composition that comprises nilotinib HCl, when measured as the total area under the curve (AUC) after oral administration or when measured as Cmax after oral administration, wherein the reference pharmaceutical composition does not comprise an amorphous solid dispersion. In some embodiments, the bioavailability is measured in a dog model in a fasted state or in a fed state. In some embodiments, a bioavailability of the pharmaceutical composition does not vary for more than 50% when orally administered in a fed state compared to a bioavailability administered in a fasted state, when measured as the total area under the curve (AUC) after oral administration or when measured as Cmax after oral administration. In some embodiments, the pharmaceutical composition comprises: a) an amorphous solid dispersion that comprises: i. nilotinib free base or nilotinib HCl in an amount of about 20 mg to about 200 mg; ii. a surfactant in an amount of about 10 mg to about 500 mg, wherein the surfactant comprises lecithin or a block copolymer of polyethylene glycol and polypropylene glycol; iii. a non-ionic hydrophilic polymer in an amount of about 10 mg to about 500 mg, wherein the non-ionic hydrophilic polymer comprises polyvinyl alcohol (PVA), polyvinylpyrrolidone (PVP), hydroxypropyl methylcellulose (HPMC), or hydroxypropyl beta cyclodextrin (HP-β-CD); and iv. optionally silicone dioxide in an amount of about 10 mg to 300 mg, and b) a pharmaceutically acceptable carrier or excipient. In some embodiments, the amorphous solid dispersion comprises: a) nilotinib free base; b) a surfactant, wherein the surfactant is selected from polymeric non-ionic surfactants and phospholipids; c) a non-ionic hydrophilic polymer; and d) optionally silicone dioxide. In some embodiments, the nilotinib free base is present in the amorphous solid dispersion in an amount of about 5 wt % to about 70 wt % based on solids. In some embodiments, the surfactant is a polymeric non-ionic surfactant. In some embodiments, the polymeric non-ionic surfactant comprises a block copolymer of polyethylene glycol and polypropylene glycol. In some embodiments, the polymeric non-ionic surfactant is Poloxamer 188. In some embodiments, the surfactant comprises one or more phospholipids. In some embodiments, the one or more phospholipids comprise phosphatidylcholine, phosphatidylethanolamine, phosphatidylinositol, phosphatidylserine, plasmalogen, sphingomyelin, and phosphatidic acid. In some embodiments, the surfactant comprises lecithin or Poloxamer 188. In some embodiments, the surfactant is present in the amorphous solid dispersion in an amount of about 5 wt % to about 70 wt % based on solids. In some embodiments, a weight ratio of the nilotinib free base to the surfactant is from about 10:1 to about 1:10. In some embodiments, the non-ionic hydrophilic polymer comprises polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-β-CD), hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL-PVAc-PEG) or a combination thereof. In some embodiments, the non-ionic hydrophilic polymer is HPMC, PVP, HP-β-CD, PVA, or PCL-PVAc-PEG. In some embodiments, the non-ionic hydrophilic polymer is present in the amorphous solid dispersion in an amount of about 5 wt % to about 70 wt % based on solids. In some embodiments, wherein a weight ratio of the nilotinib free base to the non-ionic hydrophilic polymer is from about 10:1 to about 1:10. In some embodiments, an average particle size of the amorphous solid dispersion, in terms of particle diameter, is from about 1 μm to about 150 μm. In some embodiments, an average particle size of the amorphous solid dispersion, in terms of particle diameter, is from about 1 μm to about 1000 μm.

Disclosed herein is a pharmaceutical composition, wherein the pharmaceutical composition comprises: a) an amorphous solid dispersion that comprises: i. nilotinib free base; ii. a surfactant, wherein the surfactant is selected from polymeric non-ionic surfactants and phospholipids; iii. a non-ionic hydrophilic polymer; and iv. optionally silicon dioxide, and b) a pharmaceutically acceptable carrier or excipient. In some embodiments, the pharmaceutical composition is in a form of a tablet or capsule. In some embodiments, the nilotinib free base is present in the pharmaceutical composition in an amount of about 10 mg to about 500 mg. In some embodiments, the surfactant is Poloxamer 188 or lecithin. In some embodiments, the surfactant is present in the pharmaceutical composition in an amount of about 10 mg to about 500 mg. In some embodiments, the non-ionic hydrophilic polymer is polyvinyl alcohol (PVA), oligosaccharide, polysaccharide, polyvinylpyrrolidone (PVP), hydroxypropyl methylcellulose (HPMC, or hypromellose), hydroxyethyl cellulose (HEC), hydroxypropyl cellulose (HPC), polyethylene oxide, hydroxypropyl beta cyclodextrin (HP-β-CD), hydropropylmethylcellulose acetate succinate (HPMCAS), polyethylene glycol (PEG), polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof. In some embodiments, the non-ionic hydrophilic polymer is present in the pharmaceutical composition in an amount of about 10 mg to about 500 mg. In some embodiments, the amorphous solid dispersion comprises silicon dioxide powder in an amount of about 10 to about 35% wt. In some embodiments, the pharmaceutical composition is free of organic acid. In some embodiments, the pharmaceutical composition is storage stable for at least 2 weeks at 75° C./75% RH, wherein a storage stable pharmaceutical composition has less than 100 ppm of Impurity A at the end of the storage period. In some embodiments, the pharmaceutical composition exhibits a bioavailability that is at least 2-fold higher than a bioavailability of a corresponding formulation comprising crystalline nilotinib, when measured as the total area under the curve (AUC) after oral administration or when measured as Cmax after oral administration. In some embodiments, the pharmaceutical composition exhibits a bioavailability that is at least 2-fold higher than a bioavailability of a reference pharmaceutical composition that comprises nilotinib HCl, when measured as the total area under the curve (AUC) after oral administration or when measured as Cmax after oral administration, wherein the reference pharmaceutical composition does not comprise an amorphous solid dispersion. In some embodiments, the bioavailability is measured in a dog model in a fasted state or in a fed state. In some embodiments, a bioavailability of the pharmaceutical composition does not vary for more than 50% when orally administered in a fed state compared to a bioavailability administered in a fasted state, when measured as the total area under the curve (AUC) after oral administration or when measured as Cmax after oral administration.

Disclosed herein is a method for preparing an amorphous solid dispersion, comprising the steps: a) combining (i) an active pharmaceutical ingredient or a pharmaceutically acceptable salt thereof, (ii) a surfactant, wherein the surfactant is selected from polymeric non-ionic surfactants and phospholipids, (iii) a non-ionic hydrophilic polymer, (iv) optionally an additive and (v) a solvent, thereby producing a liquid mixture or solution, and b) removing the solvent from said mixture, thereby producing an amorphous solid dispersion. In some embodiments, the solvent is an organic solvent or a mixture of organic solvents. In some embodiments, the solvent is alcohol or contains alcohol. In some embodiments, the combining comprises dissolving the active pharmaceutical ingredient or a pharmaceutically acceptable salt thereof, the surfactant, and the non-ionic hydrophilic polymer in the solvent. In some embodiments, the removing comprises spray-drying or rotor evaporation. In some embodiments, the removing comprises spraying of the solution onto an adsorbent and drying in a fluid bed equipment.

Disclosed herein is a method of treating cancer, comprising administering to a subject in need thereof the amorphous solid dispersion or the pharmaceutical composition of any one of the embodiments disclosed herein. In some embodiments, the cancer is a blood cancer. In some embodiments, the blood cancer is chronic myelogenous leukemia (CML). In some embodiments, the cancer is a solid tumor.

Disclosed herein is a method of inhibiting BCR-ABL tyrosine-kinase, comprising administering to a subject in need thereof the amorphous solid dispersion or the pharmaceutical composition of any one of the embodiments disclosed herein. In some embodiments, the subject is resistant to or intolerant to imatinib. In some embodiments, the method further comprising administering a chemotherapeutic agent. In some embodiments, the method further comprising administering a hematopoietic growth factor such as erythropoietin or G-CSF.

The invention claimed is:

1. A pharmaceutical composition, wherein the pharmaceutical composition comprises:
   a) an amorphous solid dispersion that comprises:
      i) nilotinib free base or a hydrochloride salt thereof, wherein the nilotinib free base or a hydrochloride salt thereof is present in the amorphous solid dispersion in an amount of about 10% to about 30% by weight;
      ii) a surfactant, wherein the surfactant comprises a phospholipid, and wherein the surfactant is present in the amorphous solid dispersion in an amount of about 5% to about 50% by weight;
      iii) a hydrophilic polymer, wherein the hydrophilic polymer is present in the amorphous solid dispersion in an amount of about 20% to about 80% by weight; and
      iv) silicon dioxide, wherein the silicon dioxide is present in the amorphous solid dispersion in an amount of about 0.1% to about 40% by weight; wherein i, ii, iii, and iv are combined and present together prior to removing all or partial solvent to form the amorphous solid dispersion; and
   b) a pharmaceutically acceptable carrier or excipient.

2. The pharmaceutical composition of claim 1, wherein the pharmaceutical composition is free of organic acid.

3. The pharmaceutical composition of claim 1, wherein the amorphous solid dispersion comprises nilotinib free base.

4. The pharmaceutical composition of claim 1, wherein the pharmaceutical composition is in a form of a tablet or capsule.

5. The pharmaceutical composition of claim 1, wherein the nilotinib free base or a hydrochloride salt thereof is present in the pharmaceutical composition in an amount of about 10 mg to about 200 mg.

6. The pharmaceutical composition of claim 1, wherein the nilotinib free base or a hydrochloride salt thereof is present in the pharmaceutical composition in an amount of about 15% to about 25% by weight.

7. The pharmaceutical composition of claim 3, wherein the nilotinib free base is present in the pharmaceutical composition in an amount of about 15% to about 25% by weight.

8. The pharmaceutical composition of claim 3, wherein the nilotinib free base is present in the pharmaceutical composition in an amount of about 25 mg to about 125 mg.

9. The pharmaceutical composition of claim 1, wherein the surfactant is present in the amorphous solid dispersion in an amount of about 25 mg to about 125 mg.

10. The pharmaceutical composition of claim 1, wherein the phospholipid is present in the pharmaceutical composition in an amount of 5% to 17% by weight.

11. The pharmaceutical composition of claim 1, wherein the pharmaceutical composition is stable for at least 2 weeks when stored at 40° C./75% RH.

12. The pharmaceutical composition of claim 1, wherein the phospholipid comprises lecithin.

13. The pharmaceutical composition of claim 1, wherein the hydrophilic polymer comprises polyvinylpyrrolidone (PVP), polyvinylpyrrolidone VA64, hydroxypropyl methylcellulose (HPMC, or hypromellose), hydroxyethyl cellulose (HEC), hydroxypropyl cellulose (HPC), hydroxypropyl beta cyclodextrin (HP-β-CD), hydropropylmethylcellulose acetate succinate (HPMCAS), polyvinyl acetate and polyvinylcaprolactame-based graft copolymer (PVAc-PVCap-PEG), polyvinyl caprolactam-polyvinyl acetate-polyethylene glycol (PCL-PVAc-PEG), or a combination thereof.

14. The pharmaceutical composition of claim 1, wherein the hydrophilic polymer is present in the amorphous solid dispersion in an amount of about 45% to about 70% by weight.

15. The pharmaceutical composition of claim 14, wherein the hydrophilic polymer comprises hydroxypropyl cellulose (HPC) and hydropropylmethylcellulose acetate succinate (HPMCAS).

16. The pharmaceutical composition of claim 1, wherein the amorphous solid dispersion comprises:
   i) nilotinib free base in an amount of about 15% to about 25% by weight of the amorphous solid dispersion;
   ii) the surfactant in an amount of about 5% to about 20% by weight of the amorphous solid dispersion, wherein the surfactant is lecithin;
   iii) the hydrophilic polymer in an amount of about 45% to about 70% by weight of the amorphous solid dispersion, wherein the hydrophilic polymer comprises hydroxypropyl cellulose (HPC) and hydropropylmethylcellulose acetate succinate (HPMCAS); and
   iv) silicon dioxide in an amount of about 0.1% to about 10% by weight of the amorphous solid dispersion.

17. The pharmaceutical composition of claim 1, wherein the pharmaceutically acceptable carrier or excipient comprises croscarmellose sodium, microcrystalline cellulose, magnesium stearate, or silicon dioxide, or any combinations thereof.

18. The pharmaceutical composition of claim 1, wherein the pharmaceutical composition exhibits a bioavailability that is at least 1.5-fold higher than a bioavailability of a corresponding formulation comprising nilotinib free base or a pharmaceutically acceptable salt thereof in a crystalline form, when measured as the total area under the curve (AUC) after oral administration or when measured as $C_{max}$ after oral administration.

19. The pharmaceutical composition of claim 1, wherein the pharmaceutical composition is in a form of a capsule.

20. The pharmaceutical composition of claim 19, wherein the capsule contains less than 1000 mg of the pharmaceutical composition.

21. The pharmaceutical composition of claim 3, wherein the nilotinib free base is present in the pharmaceutical composition in an amount of about 75 mg.

22. The pharmaceutical composition of claim 3, wherein the nilotinib free base is present in the pharmaceutical composition in an amount of about 100 mg.

23. The pharmaceutical composition of claim 1, wherein the surfactant is lecithin.

24. The pharmaceutical composition of claim 1, wherein the surfactant is soybean lecithin.

25. The pharmaceutical composition of claim 1, wherein the amorphous solid dispersion comprises:
   i) nilotinib free base in an amount of about 50 mg to about 125 mg;
   ii) the surfactant in an amount of about 25 mg to about 75 mg, wherein the surfactant is lecithin;
   iii) the hydrophilic polymer in an amount of about 200 mg to about 400 mg, wherein the hydrophilic polymer comprises hydroxypropyl cellulose (HPC) and hydropropylmethylcellulose acetate succinate (HPMCAS); and
   iv) silicon dioxide in an amount of 10 mg to 50 mg.

26. The pharmaceutical composition of claim 1, the pharmaceutically acceptable carrier or excipient comprises an anti-adherent, a cellulosic-based polymer, a disintegrant, or any combinations thereof.

27. The pharmaceutical composition of claim 1, the pharmaceutically acceptable carrier or excipient comprises polyvinylpolypyrrolidone (PVPP), microcrystalline cellulose, magnesium stearate, or silicon dioxide, or any combinations thereof.

28. The pharmaceutical composition of claim 1, comprising
   a) the amorphous solid dispersion that comprises:
      i) nilotinib free base in an amount of about 75 mg;
      ii) the surfactant in an amount of about 25 mg to about 50 mg, wherein the surfactant is lecithin;
      iii) the hydrophilic polymer in an amount of about 250 mg, wherein the hydrophilic polymer comprises hydroxypropyl cellulose (HPC) and hydropropylmethylcellulose acetate succinate (HPMCAS); and
      iv) silicon dioxide in an amount of 10 mg to 50 mg; and
   b) the pharmaceutically acceptable carrier or excipient that comprises polyvinylpolypyrrolidone (PVPP), microcrystalline cellulose, magnesium stearate, and silicon dioxide.

29. The pharmaceutical composition of claim 1, comprising
   a) the amorphous solid dispersion that comprises:
      i) nilotinib free base in an amount of about 100 mg;
      ii) the surfactant in an amount of about 50 mg, wherein the surfactant is lecithin;
      iii) the hydrophilic polymer in an amount of about 200 mg to about 400 mg, wherein the hydrophilic polymer comprises hydroxypropyl cellulose (HPC) and hydropropylmethylcellulose acetate succinate (HPMCAS); and
      iv) silicon dioxide in an amount of 10 mg to 50 mg; and
   b) the pharmaceutically acceptable carrier or excipient that comprises croscarmellose sodium, microcrystalline cellulose, magnesium stearate, and silicon dioxide.

30. The pharmaceutical composition of claim 1, wherein the silicon dioxide is present in the amorphous solid dispersion in an amount of about 0.1% to about 10% by weight.

* * * * *